United States Patent
Dilligan et al.

(10) Patent No.: US 11,622,881 B2
(45) Date of Patent: Apr. 11, 2023

(54) COOLING CAP ASSEMBLY AND COOLING UNIT

(71) Applicant: Cooler Heads Care, Inc., San Diego, CA (US)

(72) Inventors: Kathleen Dilligan, San Diego, CA (US); Jeffrey Weintraub, San Carlos, CA (US); Todd Pelman, Moss Beach, CA (US); Robert H J Miros, Sausalito, CA (US); Samuel Michael Lopez, San Francisco, CA (US); Ian Edward Hughes, Santa Rosa, CA (US); Ricardo Salinas, San Francisco, CA (US)

(73) Assignee: Cooler Heads Care, Inc., San Diego, CA (US)

(*) Notice: Subject to any disclaimer, the term of this patent is extended or adjusted under 35 U.S.C. 154(b) by 0 days.

(21) Appl. No.: 17/495,370

(22) Filed: Oct. 6, 2021

(65) Prior Publication Data

US 2022/0023094 A1  Jan. 27, 2022

Related U.S. Application Data

(63) Continuation of application No. 16/892,198, filed on Jun. 3, 2020, now Pat. No. 11,141,309.
(Continued)

(51) Int. Cl.
*A61F 7/00* (2006.01)

(52) U.S. Cl.
CPC .... *A61F 7/0085* (2013.01); *A61F 2007/0008* (2013.01); *A61F 2007/0056* (2013.01); *A61F 2007/0095* (2013.01)

(58) Field of Classification Search
CPC ............ A61F 7/0085; A61F 2007/0008; A61F 2007/0056; A61F 2007/0095
See application file for complete search history.

(56) References Cited

U.S. PATENT DOCUMENTS

| 1,809,038 A | 6/1931 | Hogrebe |
| 3,645,275 A | 2/1972 | Nolen |
| (Continued) | | |

FOREIGN PATENT DOCUMENTS

| EP | 0 050 948 A2 | 5/1982 |
| EP | 0 070 986 B1 | 2/1983 |
| (Continued) | | |

OTHER PUBLICATIONS

International Search Report and Written Opinion dated Oct. 8, 2020, for International Application No. PCT/US2020/035971, 14 pages.
(Continued)

*Primary Examiner* — Joseph A Stoklosa
*Assistant Examiner* — Adam J Avigan
(74) *Attorney, Agent, or Firm* — Cooley LLP

(57) ABSTRACT

Devices, systems, and methods herein relate to cooling a head of a patient. These systems and methods may comprise a cooling cap assembly comprising a heat exchanger configured to be wrapped around a head of a patient and a compression assembly releasably coupled to the heat exchanger. The compression assembly may comprise an enclosure and an inflatable member coupled to an internal surface of the enclosure. When coupled, the inflatable member may be positioned between the enclosure and the heat exchanger. The heat exchanger may be separate from and moveable relative to the inflatable member.

22 Claims, 36 Drawing Sheets

Related U.S. Application Data

(60) Provisional application No. 62/882,429, filed on Aug. 2, 2019, provisional application No. 62/856,691, filed on Jun. 3, 2019.

(56) References Cited

U.S. PATENT DOCUMENTS

| | | | |
|---|---|---|---|
| 4,138,743 A | 2/1979 | Elkins et al. | |
| 4,382,446 A | 5/1983 | Truelock et al. | |
| 4,425,916 A | 1/1984 | Bowen | |
| 4,552,149 A | 11/1985 | Tatsuki | |
| 4,566,455 A | 1/1986 | Kramer | |
| 4,750,493 A | 6/1988 | Brader | |
| 4,753,242 A | 6/1988 | Saggers | |
| 4,765,338 A | 8/1988 | Turner et al. | |
| 4,920,963 A | 5/1990 | Brader | |
| 5,163,425 A | 11/1992 | Nambu et al. | |
| 5,342,411 A | 8/1994 | Maxted et al. | |
| 5,603,728 A | 2/1997 | Pachys | |
| 5,658,324 A | 8/1997 | Bailey, Sr. et al. | |
| 5,698,536 A | 12/1997 | Segall et al. | |
| 5,871,526 A | 2/1999 | Gibbs et al. | |
| 5,897,581 A | 4/1999 | Fronda et al. | |
| 5,950,234 A | 9/1999 | Leong et al. | |
| 5,956,759 A | 9/1999 | Benedict | |
| 5,979,775 A | 11/1999 | Raya | |
| 6,030,412 A | 2/2000 | Klatz et al. | |
| 6,156,059 A | 12/2000 | Olofsson | |
| 6,312,453 B1 | 11/2001 | Stefanile et al. | |
| 6,341,500 B1 | 1/2002 | Paxman | |
| 6,357,250 B1 | 3/2002 | Paxman | |
| 6,367,084 B1 | 4/2002 | Keast | |
| 6,595,985 B1 | 7/2003 | Tobinick | |
| 6,645,230 B2 | 11/2003 | Whitehurst | |
| 6,865,825 B2 | 3/2005 | Bailey, Sr. et al. | |
| 6,994,863 B2 | 2/2006 | Eini et al. | |
| 6,997,923 B2 | 2/2006 | Anderson et al. | |
| 7,850,683 B2 | 12/2010 | Elkins et al. | |
| 7,862,558 B2 | 1/2011 | Elkins et al. | |
| 8,109,865 B2 | 2/2012 | Jackson | |
| 8,402,772 B1 | 3/2013 | Duval et al. | |
| 8,449,590 B2 | 5/2013 | Brader | |
| 8,454,671 B2 | 6/2013 | Lennox et al. | |
| 8,461,108 B2 | 6/2013 | Hsu et al. | |
| 9,061,880 B2 | 6/2015 | Paxman | |
| 9,072,498 B2 | 7/2015 | Elkins et al. | |
| 9,101,463 B2 | 8/2015 | Stormby | |
| 9,345,614 B2 | 5/2016 | Schaefer et al. | |
| 9,380,967 B2 | 7/2016 | Esenaliev et al. | |
| 9,421,125 B2 | 8/2016 | Stormby | |
| 9,452,129 B1 | 9/2016 | Samuel et al. | |
| 9,492,681 B2 | 11/2016 | Aydt et al. | |
| 9,532,901 B2 | 1/2017 | Nasser | |
| 9,630,021 B2 | 4/2017 | Jackson | |
| 9,681,980 B2 | 6/2017 | Swyer et al. | |
| 9,737,103 B2 | 8/2017 | Preston-Powers | |
| 9,867,965 B1 | 1/2018 | Kantor et al. | |
| 9,937,117 B2 | 4/2018 | Andres | |
| 10,080,717 B2 | 9/2018 | Samuel et al. | |
| 10,112,058 B2 | 10/2018 | Hamid | |
| 10,201,581 B2 | 2/2019 | Woo | |
| 10,231,656 B2 | 3/2019 | Esenaliev et al. | |
| 10,231,908 B2 | 3/2019 | Andres | |
| 10,271,987 B2 | 4/2019 | Rajguru et al. | |
| 10,307,088 B2 | 6/2019 | Esenaliev et al. | |
| 10,357,466 B2 | 7/2019 | Petti et al. | |
| 10,363,432 B2 | 7/2019 | Hamid | |
| 10,426,655 B2 | 10/2019 | Schaefer et al. | |
| 10,470,922 B1 | 11/2019 | Venturi | |
| 10,478,637 B2 | 11/2019 | Banker | |
| 10,512,587 B2 | 12/2019 | Quisenberry et al. | |
| 10,525,278 B2 | 1/2020 | Wasserbauer et al. | |
| 10,765,166 B2 | 9/2020 | Krishnan | |
| 10,773,097 B2 | 9/2020 | Wasserbauer et al. | |
| 11,141,309 B2 | 10/2021 | Dilligan et al. | |
| 2002/0019654 A1* | 2/2002 | Ellis | A61F 7/007 607/98 |
| 2002/0058976 A1 | 5/2002 | Lee | |
| 2002/0091377 A1 | 7/2002 | Anderson et al. | |
| 2002/0143375 A1 | 10/2002 | Mitomi | |
| 2002/0173780 A1 | 11/2002 | Altshuler et al. | |
| 2003/0088300 A1 | 5/2003 | Vester | |
| 2004/0127961 A1 | 7/2004 | Whitehurst | |
| 2004/0162596 A1 | 8/2004 | Altshuler et al. | |
| 2004/0243202 A1* | 12/2004 | Lennox | A61F 7/0085 607/104 |
| 2005/0171457 A1 | 8/2005 | Yang | |
| 2005/0215988 A1 | 9/2005 | Altshuler et al. | |
| 2006/0005291 A1 | 1/2006 | Bedford | |
| 2006/0009750 A1 | 1/2006 | Altshuler et al. | |
| 2006/0122668 A1 | 6/2006 | Anderson et al. | |
| 2006/0142823 A1 | 6/2006 | Whang | |
| 2007/0016117 A1 | 1/2007 | Sliwa et al. | |
| 2007/0073308 A1 | 3/2007 | Anderson et al. | |
| 2007/0233209 A1 | 10/2007 | Whitehurst | |
| 2007/0255355 A1 | 11/2007 | Altshuler et al. | |
| 2008/0009842 A1 | 1/2008 | Manstein et al. | |
| 2008/0033516 A1 | 2/2008 | Altshuler et al. | |
| 2008/0097560 A1 | 4/2008 | Radziunas et al. | |
| 2008/0171093 A1 | 7/2008 | Roth et al. | |
| 2009/0254159 A1 | 10/2009 | Stormby | |
| 2010/0137951 A1* | 6/2010 | Lennox | A61F 7/02 607/104 |
| 2010/0179469 A1 | 7/2010 | Hammond et al. | |
| 2010/0186436 A1* | 7/2010 | Stormby | A61F 7/10 62/259.3 |
| 2010/0319110 A1 | 12/2010 | Preston-Powers | |
| 2011/0020279 A1 | 1/2011 | Shantha | |
| 2011/0137230 A1 | 6/2011 | Altshuler et al. | |
| 2012/0035583 A1 | 2/2012 | Sepkuty | |
| 2012/0089211 A1 | 4/2012 | Curtis et al. | |
| 2013/0085556 A1 | 4/2013 | Gillespie et al. | |
| 2013/0138185 A1 | 5/2013 | Paxman et al. | |
| 2013/0211484 A1 | 8/2013 | Rozental | |
| 2013/0315924 A1 | 11/2013 | Hsu et al. | |
| 2014/0046410 A1 | 2/2014 | Wyatt | |
| 2014/0074198 A1 | 3/2014 | Bledsoe | |
| 2014/0128946 A1 | 5/2014 | Nasser | |
| 2014/0236271 A1 | 8/2014 | Fronda et al. | |
| 2014/0350643 A1 | 11/2014 | Pepitone et al. | |
| 2015/0040937 A1 | 2/2015 | Yang | |
| 2015/0164165 A1 | 6/2015 | Goubron | |
| 2015/0351957 A1 | 12/2015 | Wilder-Smith et al. | |
| 2016/0022478 A1 | 1/2016 | Schaefer et al. | |
| 2016/0206470 A1 | 7/2016 | Vic et al. | |
| 2016/0302964 A1 | 10/2016 | Wijngaarden-Smit et al. | |
| 2016/0338997 A1 | 11/2016 | Ryan | |
| 2016/0354234 A1* | 12/2016 | Dabrowiak | A61F 7/007 |
| 2016/0374411 A1* | 12/2016 | Brooks | A61F 7/007 165/104.21 |
| 2017/0020721 A1 | 1/2017 | Kobilca | |
| 2017/0049616 A1 | 2/2017 | Schaefer et al. | |
| 2017/0087006 A1 | 3/2017 | Endo | |
| 2017/0119788 A1 | 5/2017 | Vanangamudi et al. | |
| 2017/0119791 A1 | 5/2017 | Vanangamudi et al. | |
| 2017/0164675 A1 | 6/2017 | Buchert | |
| 2017/0209304 A1 | 7/2017 | Zumbrunnen et al. | |
| 2017/0224528 A1 | 8/2017 | Berg et al. | |
| 2017/0224529 A1 | 8/2017 | Berg et al. | |
| 2017/0224935 A1 | 8/2017 | Hoffmann et al. | |
| 2017/0239082 A1 | 8/2017 | Unver et al. | |
| 2017/0239083 A1 | 8/2017 | Unver et al. | |
| 2017/0281402 A1 | 10/2017 | Swyer et al. | |
| 2017/0296379 A1 | 10/2017 | Paxman et al. | |
| 2017/0333248 A1 | 11/2017 | Nakamatsu | |
| 2018/0015299 A1 | 1/2018 | Kawa | |
| 2018/0103712 A1 | 4/2018 | Krishnan | |
| 2018/0199879 A1 | 7/2018 | Kanistros | |
| 2018/0303662 A1 | 10/2018 | Berg | |
| 2018/0311070 A1 | 11/2018 | Berg | |
| 2020/0330263 A1* | 10/2020 | Dabrowiak | F25B 27/00 |

(56) References Cited

U.S. PATENT DOCUMENTS

FOREIGN PATENT DOCUMENTS

| | | |
|---|---|---|
| EP | 0 076 080 A2 | 4/1983 |
| EP | 0 101 068 B1 | 2/1984 |
| EP | 0 158 470 A1 | 10/1985 |
| EP | 0 208 113 B1 | 1/1987 |
| EP | 0 410 986 B1 | 2/1991 |
| EP | 0 778 756 B1 | 6/1997 |
| EP | 0 864 309 A2 | 9/1998 |
| EP | 0 874 666 B1 | 11/1998 |
| EP | 0 949 892 B1 | 10/1999 |
| EP | 1 048 609 A1 | 11/2000 |
| EP | 1 084 989 A1 | 3/2001 |
| EP | 1 104 272 B1 | 6/2001 |
| EP | 1 138 349 B1 | 10/2001 |
| EP | 1 347 711 B1 | 10/2003 |
| EP | 1 457 234 B1 | 9/2004 |
| EP | 1 665 996 A2 | 6/2006 |
| EP | 1 700 573 A2 | 9/2006 |
| EP | 2 117 484 B1 | 2/2007 |
| EP | 1 959 885 B1 | 8/2008 |
| EP | 2 249 672 B1 | 11/2010 |
| EP | 2 280 675 B1 | 2/2011 |
| EP | 2 289 598 A1 | 3/2011 |
| EP | 2 311 399 A2 | 4/2011 |
| EP | 2 316 372 A1 | 5/2011 |
| EP | 2 363 022 A2 | 9/2011 |
| EP | 2 600 810 B1 | 6/2013 |
| EP | 2 603 183 B1 | 6/2013 |
| EP | 2 623 146 B1 | 8/2013 |
| EP | 2 675 524 B1 | 12/2013 |
| EP | 2 809 381 B1 | 12/2014 |
| EP | 2 878 287 A1 | 6/2015 |
| EP | 3 046 441 B1 | 7/2016 |
| EP | 3 153 138 A1 | 4/2017 |
| JP | H08131473 | 5/1996 |
| WO | WO 86/05767 | 10/1986 |
| WO | WO 88/07972 | 10/1988 |
| WO | WO 89/09583 | 10/1989 |
| WO | WO 95/10251 | 4/1995 |
| WO | WO 96/06580 | 3/1996 |
| WO | WO 98/16176 | 4/1998 |
| WO | WO 2009/019457 | 2/1999 |
| WO | WO 99/44454 | 9/1999 |
| WO | WO 00/03666 | 1/2000 |
| WO | WO 00/09052 | 2/2000 |
| WO | WO 01/54606 | 8/2001 |
| WO | WO 02/32381 | 4/2002 |
| WO | WO 02/053050 | 7/2002 |
| WO | WO 02/069825 | 9/2002 |
| WO | WO 03/047479 | 6/2003 |
| WO | WO 03/077783 | 9/2003 |
| WO | WO 2004/033040 | 4/2004 |
| WO | WO 2004/039191 | 5/2004 |
| WO | WO 2004/075978 | 9/2004 |
| WO | WO 2005/041655 | 5/2005 |
| WO | WO 2006/126059 | 11/2006 |
| WO | WO 2007/067129 | 6/2007 |
| WO | WO 2008/035910 | 3/2008 |
| WO | WO 2008/099017 | 8/2008 |
| WO | WO 2009/095690 | 8/2009 |
| WO | WO 2009/111793 | 9/2009 |
| WO | WO 2009/131420 | 10/2009 |
| WO | WO 2009/135054 | 11/2009 |
| WO | WO 2009/147413 | 12/2009 |
| WO | WO 2010/078581 | 7/2010 |
| WO | WO 2011/015821 | 2/2011 |
| WO | WO 2011/098761 | 8/2011 |
| WO | WO 2012/017394 | 2/2012 |
| WO | WO 2012/020267 | 2/2012 |
| WO | WO 2012/028730 | 3/2012 |
| WO | WO 2012/060584 | 5/2012 |
| WO | WO 2012/110178 | 8/2012 |
| WO | WO 2013/007964 | 1/2013 |
| WO | WO 2013/048904 | 4/2013 |
| WO | WO 2013/191426 | 12/2013 |
| WO | WO 2014/025082 | 2/2014 |
| WO | WO 2014/120090 | 8/2014 |
| WO | WO 2014/131115 | 9/2014 |
| WO | WO 2015/039990 | 3/2015 |
| WO | WO 2015/082455 | 6/2015 |
| WO | WO 2015/100348 | 7/2015 |
| WO | WO 2015/127066 | 8/2015 |
| WO | WO 2015/178960 | 11/2015 |
| WO | WO 2015/180804 | 12/2015 |
| WO | WO 2016/007678 | 1/2016 |
| WO | WO 2016/014748 | 1/2016 |
| WO | WO 2016/022865 | 2/2016 |
| WO | WO 2016/029105 | 2/2016 |
| WO | WO 2016/046534 | 3/2016 |
| WO | WO 2016/046535 | 3/2016 |
| WO | WO 2016/046536 | 3/2016 |
| WO | WO 2016/059167 | 4/2016 |
| WO | WO 2016/059173 | 4/2016 |
| WO | WO 2016/126806 | 8/2016 |
| WO | WO 2017/007910 | 1/2017 |
| WO | WO 2017/023833 | 2/2017 |
| WO | WO 2017/062108 | 4/2017 |
| WO | WO 2017/069509 | 4/2017 |
| WO | WO 2017/085272 | 5/2017 |
| WO | WO 2017/085273 | 5/2017 |
| WO | WO 2017/172836 | 10/2017 |
| WO | WO 2017/205266 | 11/2017 |
| WO | WO 2017/220998 | 12/2017 |
| WO | WO 2018/064428 | 4/2018 |
| WO | WO 2018/169131 | 9/2018 |
| WO | WO 2019/016616 | 1/2019 |
| WO | WO 2019/033186 | 2/2019 |
| WO | WO 2019/035895 | 2/2019 |
| WO | WO 2020/247532 | 12/2020 |

OTHER PUBLICATIONS

The International Bureau of WIPO, International Preliminary Report on Patentability, dated Dec. 7, 2021, for International Application No. PCT/US2020/035971, 7 pages.

* cited by examiner

FIG. 7A  FIG. 7B  FIG. 7C
FIG. 7D  FIG. 7E  FIG. 7F

Step 1: Open Outer Shell 800

Step 2: Place hard shell inside 802

Step 3: Place Air Pillow Inside

Step 4: Attach Pump

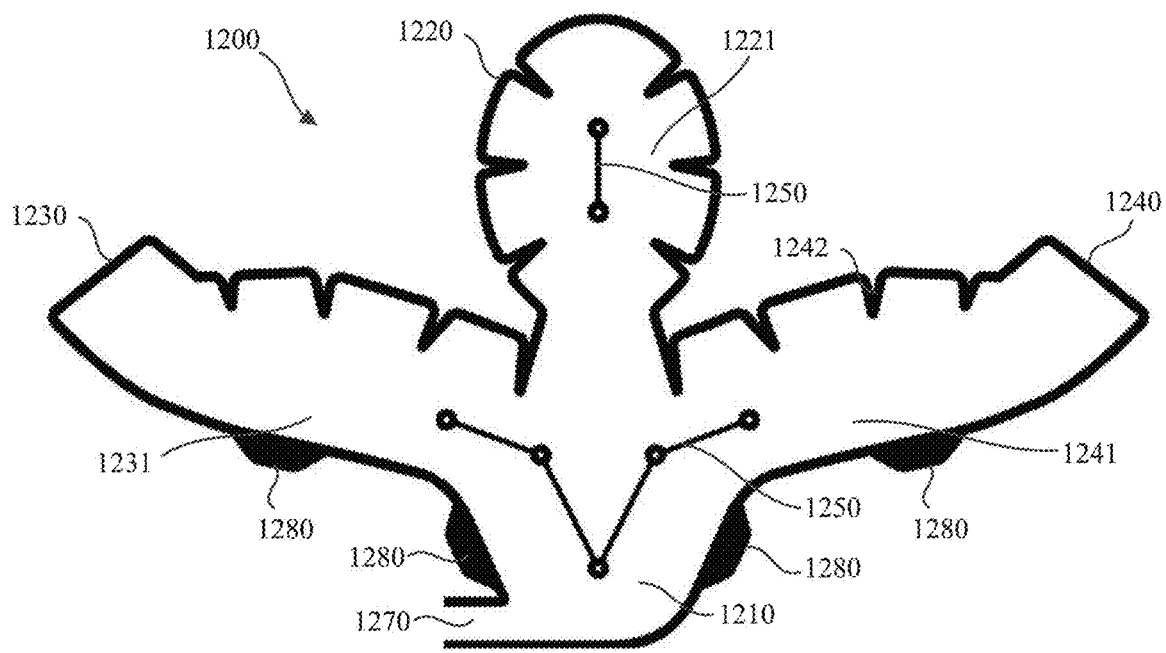
FIG. 12A
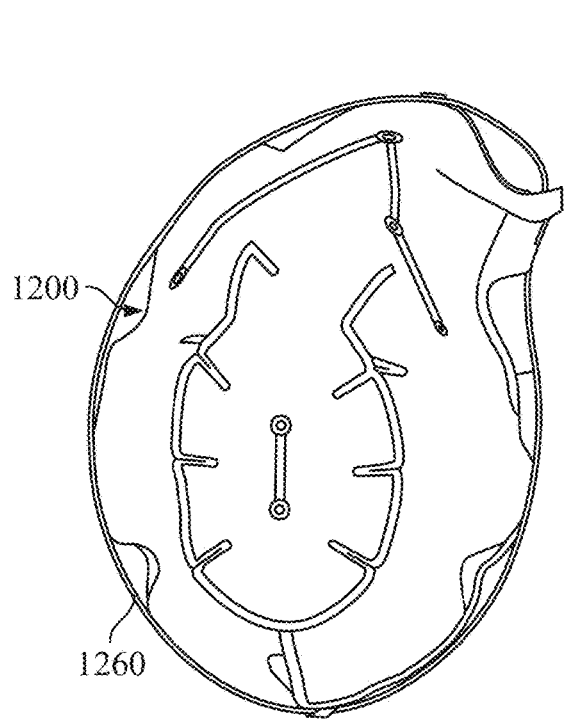 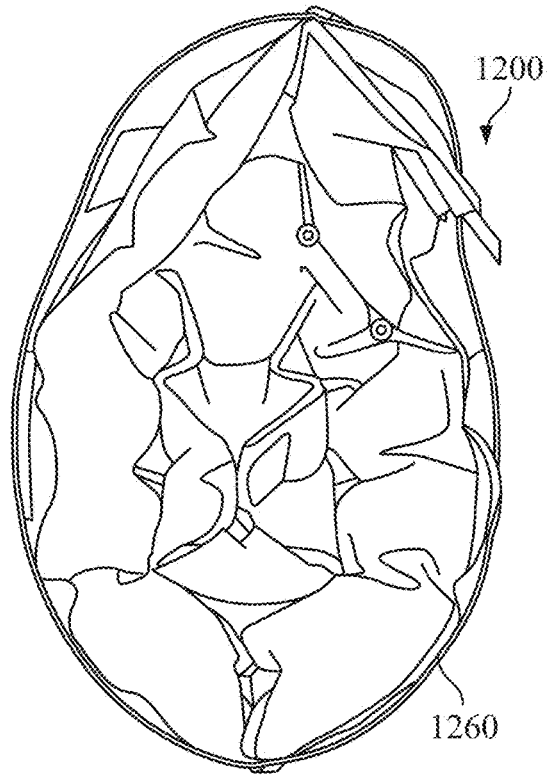
FIG. 12B    FIG. 12C

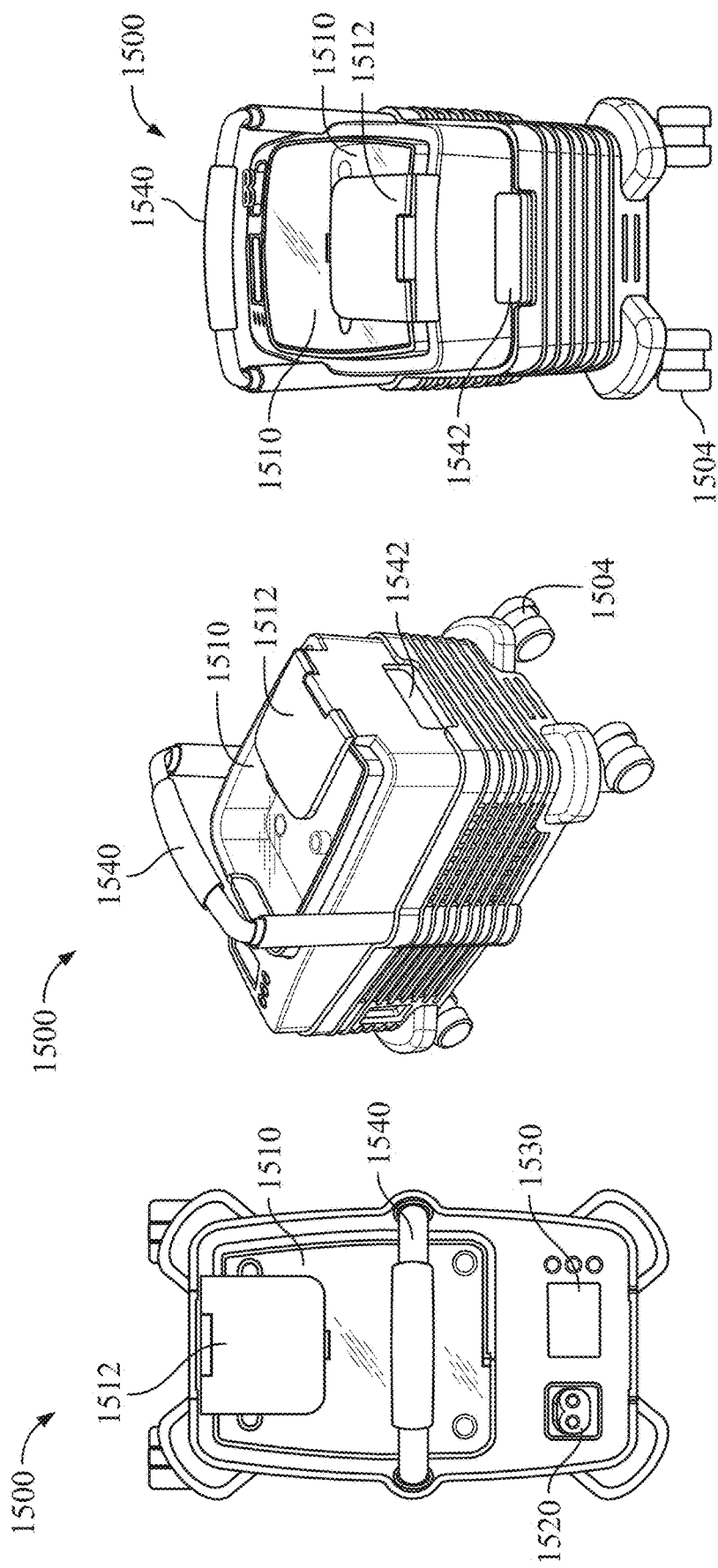

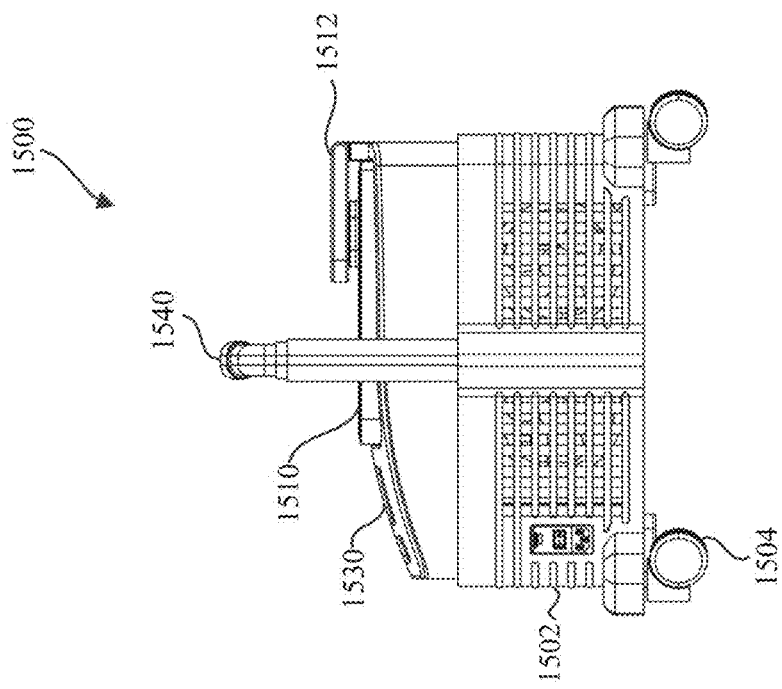
FIG. 15K
FIG. 15J
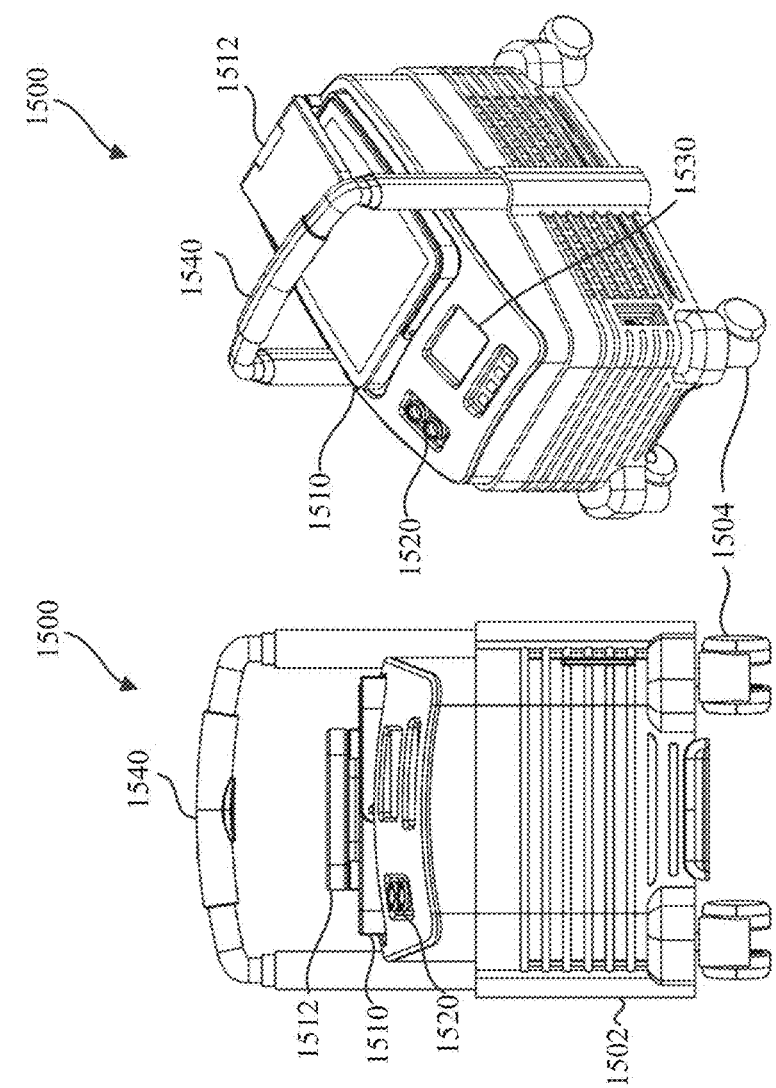
FIG. 15I

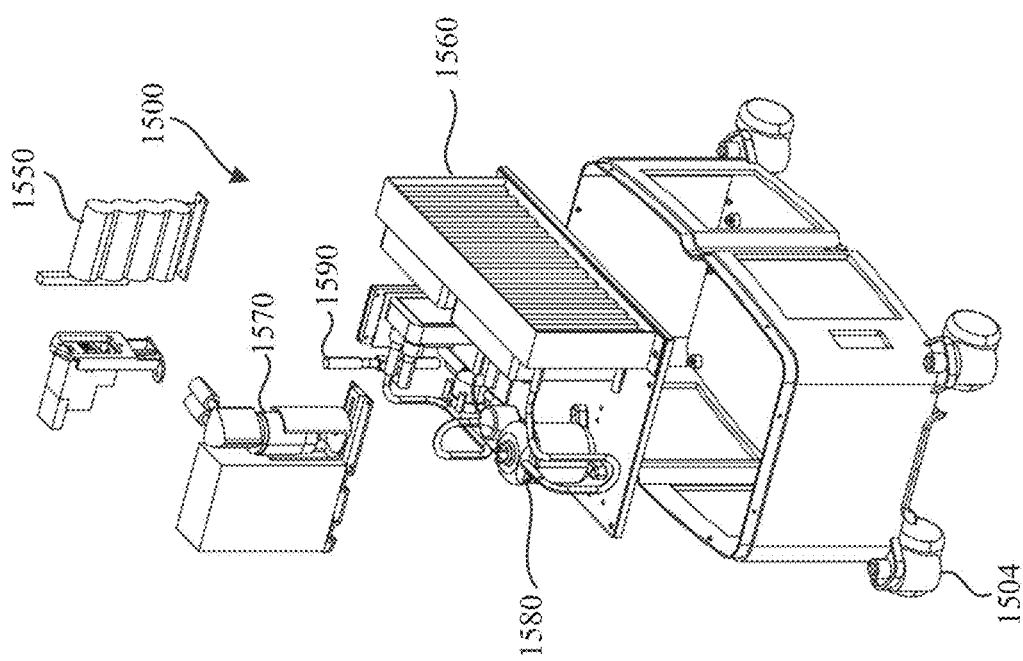
FIG. 15N
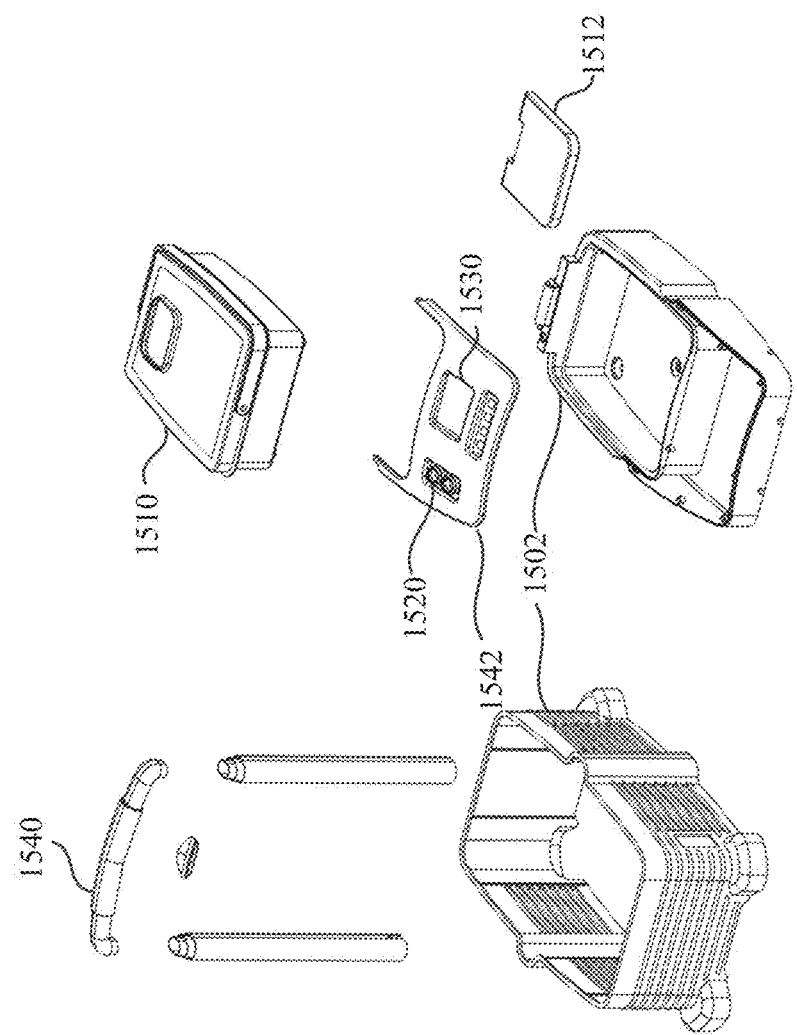
FIG. 15M
FIG. 15L

COOLING CAP ASSEMBLY AND COOLING UNIT

CROSS-REFERENCE TO RELATED APPLICATIONS

This application is a continuation of U.S. patent application Ser. No. 16/892,198, filed on Jun. 3, 2020, now issued as U.S. Pat. No. 11,141,309, which claims priority to U.S. Provisional Application Ser. No. 62/856,691, filed on Jun. 3, 2019, and U.S. Provisional Application Ser. No. 62/882,429, filed on Aug. 2, 2019, the contents of each of which is hereby incorporated by reference in its entirety.

FIELD

Devices, systems, and methods herein relate to reducing a temperature of a scalp of a patient.

BACKGROUND

Alopecia is a common side effect of chemotherapy and may cause distress for some patients due to the visible change in appearance and loss of a physical attribute. For some patients, alopecia due to chemotherapy may lead to depression and therefore impede patient recovery. In response, some patients undergoing chemotherapy receive scalp cooling treatments. However, conventional techniques are not optimized for patient comfort and are typically performed at a treatment center where a technician ensures that a cooling device is properly fitted and used correctly. As such, additional devices, systems, and methods for cooling a scalp may be desirable.

SUMMARY

Described here are devices, systems, and methods for providing cooling to reduce or prevent alopecia associated with chemotherapy. These systems and methods may, for example, increase a contact area between a cooling element (e.g., heat exchanger) and a scalp of a patient. This may, for example, increase cooling treatment efficiency. Furthermore, the devices and system described herein may be compact and portable such that a patient may perform cooling treatment by themselves at their convenience (e.g., in their home).

In some variations, a cooling cap assembly may comprise a heat exchanger configured to be wrapped around a head of a patient, and a compression assembly releasably coupled to the heat exchanger. The compression assembly may comprise an enclosure and an inflatable member coupled to an internal surface of the enclosure. When coupled, the inflatable member may be positioned between the enclosure and the heat exchanger. The heat exchanger may be separate from and moveable relative to the inflatable member.

In some variations, the inflatable member may comprise a deflated configuration and an inflated configuration. Transitioning the inflatable member from the deflated to the inflated configuration may increase a pressure applied to the head of the patient. In some variations, a fluid pump may be coupled to the inflatable member. In some variations, the enclosure may be configured to generate a counter pressure when the inflatable member is in the inflated configuration. In some variations, the compression assembly may be configured to generate from about 0.1 lb/in$^2$ to about 10 lb/in$^2$ of compression to the head when the inflatable member is in the inflated configuration.

In some variations, the inflatable member may comprise a plurality of chambers. In some of these variations, each of the plurality of chambers may be independently inflatable. In some variations, the inflatable member may comprise a top inflatable portion, a first inflatable side portion, and a second inflatable side portion. Each portion may comprise a chamber. In some of these variations, a length of the first inflatable side portion and a length of the second inflatable side portion may be each more than a length of the top inflatable portion. In some variations, a length of the first inflatable side portion and a length of the second inflatable side portion may be less than a length of the top inflatable portion. In some variations, the side inflatable portions of the inflatable member may be configured to adjustably overlap so as to surround at least a portion of the head. In some variations, the inflatable member may comprise a fluid barrier. In some variations, the inflatable member may comprise one or more slits. In some variations, the inflatable member may comprise at least three chambers. In some variations, the inflatable member may comprise one or more fasteners.

In some variations, the heat exchanger may comprise a base portion, a top portion, a first side portion, and a second side portion. In some variations, the heat exchanger may comprise a set of fluid barriers where each fluid barrier of the set of fluid barriers is about 5 mm to about 15 mm from an adjacent fluid barrier in the set of fluid barriers. In some barriers, each fluid barrier in the set of fluid barriers may comprise a diameter of from about 5 mm to about 10 mm. In some variations, a temperature sensor may be positioned within an opening of at least one fluid barrier of the set of fluid barriers. In some variations, at least one fluid barrier of the set of fluid barriers comprises a torus shape. In some variations, the first side portion may comprise a first arm and the second side portion may comprise a second arm.

In some of these variations, the top portion, first side portion, and the second side portion each comprise a first lobe and a second lobe. In some of these variations, a length of the first lobes of the first portion and the second portion may be more than a length of the second lobes of the first portion and the second portion.

In some variations, each portion of the heat exchanger may comprise at least a portion of a fluid channel. In some variations, a length of the first side portion and the second side portion may be less than a length of the top portion. In some variations, an area of either the first side portion or the second side portion to an area of the top portion may be from about 2:1 to about 0.5:1. In some variations, the top portion may define a longitudinal axis. The first side portion and the second side portion may extend from the base portion at an acute angle with respect to the longitudinal axis. In some variations, one or more end portions of the heat exchanger may be configured to adjustably overlap so as to surround at least a portion of the head. In some variations, the heat exchanger may comprise a flexible material. In some variations, the heat exchanger may comprise a non-woven fabric. In some variations, the heat exchanger may comprise one or more fluid channels each comprising a cross-sectional area of from about 9 mm$^2$ to about 100 mm$^2$.

In some variations, one or more sensors may be coupled to the heat exchanger and configured to measure one or more characteristics of the compression assembly. In some of these variations, the one or more sensors may comprise a temperature sensor and a pressure sensor. In some of these variations, the heat exchanger may comprise at least one sensor in each of the portions of the heat exchanger. In some variations, the heat exchanger may comprise a fastener.

In some variations, the enclosure may comprise a rigid or a semi-rigid material. In some variations, the enclosure may be configured to surround at least a portion of the inflatable member. In some variations, the enclosure may define a cavity configured to surround at least a portion of the inflatable member. In some variations, the enclosure may comprise a hemispherical shell. In some variations, the enclosure may comprise a helmet. In some of these variations, the enclosure may further comprises a flexible cover. In some variations, the enclosure may comprise a fastener configured to couple to the inflatable member. In some of these variations, the flexible cover may comprise a fastener. In some variations, the enclosure may define a cavity configured to receive the head of a patient.

In some variations, a liner may be configured to be disposed between the heat exchanger and a scalp of the patient. A fastener may be releasably coupled to the compression assembly and the patient. In some of these variations, the liner may comprise a flexible material.

In some variations, a cooling unit fluidly may be coupled to the compression assembly. The cooling unit may comprise a fluid connector releasably coupled to the heat exchanger, a compressor, a reservoir, and a pump. In some of these variations, the cooling unit may comprise a housing, a battery, and a fluid reservoir releasably coupled to the housing. In some of these variations, the cooling unit may be configured to circulate a fluid through the heat exchanger. In some of these variations, the fluid may comprise one or more of water (e.g., liquid water and ice) and salt, water and glycol, and water and alcohol, which may lower a freezing point of the fluid. In some variations, a ratio of water to alcohol may be from about 20:1 to about 5:1.

In some variations, a cooling cap assembly may comprise a heat exchanger configured to be wrapped around a head of a patient. A compression assembly may be releasably coupled to the heat exchanger. The compression assembly may comprise an enclosure and an inflatable member coupled to an internal surface of the enclosure. When coupled, the inflatable member may be positioned between the enclosure and the heat exchanger. The heat exchanger may be separate from and moveable relative to the inflatable member. Transitioning the inflatable member from a deflated configuration to an inflated configuration may increase a contact area between the heat exchanger and to the head of the patient.

Also described here are methods. In some variations, a method of cooling a scalp of a head to reduce hair loss resultant from chemotherapy may comprise wrapping a heat exchanger around a portion of the scalp, and placing a compression assembly on the head and over the wrapped heat exchanger. The compression assembly may comprise a semi-rigid outer member and an inflatable inner member coupled to the outer member. The inflatable member may be inflated to compress the heat exchanger between the inflatable member and the scalp.

In some variations, the heat exchanger may be separate from and moveable relative to the inflatable member. In some variations, the inflatable member may transition from a deflated to an inflated configuration to increase a pressure applied to the head. In some variations, a counter pressure may be generated using the outer member when the inflatable member is in an inflated configuration. In some variations, from about 0.1 lb/in$^2$ to about 10 lb/in$^2$ of compression may be generated to the head when the inflatable member is in an inflated configuration. In some variations, the inflatable member may comprise a plurality of independently inflatable chambers. In some variations, a liner may be placed around the portion of the scalp such that the heat exchanger may be positioned between the liner and the inflatable member.

In some variations, the heat exchanger may comprise a base portion, a top portion, a first side portion, and a second side portion. Ends of the first side portion and the second side portion may be placed over one another. An end of the top portion may be placed over the ends of the first side portion and the second side portion so as to surround at least the portion of the scalp.

In some variations, the inflatable member may be inflated with a gas or a liquid. In some variations, the inflatable member may be inflated using a hand pump. In some variations, a fluid may be circulated through the heat exchanger. The fluid may comprise a temperature of from about −10° C. to about 5° C. In some variations, the heat exchanger may be removed from the scalp using the compression assembly. In some of these variations, the heat exchanger may be placed back onto the scalp using the compression assembly. In some variations, a fastener may releasably attach the compression assembly to the scalp.

Also described here are devices. In some variations, a cooling cap assembly may comprise a flexible heat exchanger configured to remove heat from a scalp of a patient. The heat exchanger may comprise a temperature sensor. An inflatable member may comprise a pouch having a top surface and a bottom surface wherein the bottom surface is releasably coupled to the heat exchanger. A pump may be configured inflate the pouch. An outer shell may be coupled to the top surface of the pouch of the inflatable member. A cooling unit may be fluidly coupled to the heat exchanger. A memory may comprise instructions to receive a temperature from the temperature sensor and adjust an output of the pump based on the temperature.

In some variations, the output of the pump may be an inflation pressure. In some variations, the temperature may be a scalp temperature. In some variations, the temperature sensor may be disposed on an external surface of the heat exchanger, within the heat exchanger, or within a fluid channel of the heat exchanger. In some variations, the heat exchanger may comprise one or more fluid channels comprising circulating fluid. In some of these variations, the temperature may be a fluid temperature.

In some variations, the temperature sensor may comprise a set of temperature sensors, the temperature may comprise a set of temperatures, and the pouch may comprise a set of chambers. The memory may comprise instructions to independently adjust an inflation pressure of each chamber of the pouch based on the set of temperatures.

In some variations, the cooling unit may be portable. In some variations, the cooling unit may comprise a releasable fluid reservoir. In some variations, the fluid reservoir may comprise a handle. In some variations, the cooling unit may comprise an adjustable handle. In some variations, the cooling unit may comprise a battery.

Also described here methods. In some variations, a method of controlling cooling of a scalp of a head of a chemotherapy patient comprising applying a cooling cap to the head. The cooling cap may comprise a flexible heat exchanger comprising a temperature sensor. An inflatable member may be releasably coupled to the heat exchanger. A shell may be coupled to the inflatable member. The inflatable member may comprise a pouch and a pump in fluid communication with the pouch to increase an inflation pressure of the pouch. A temperature may be measured using the temperature sensor. The inflation pressure of the pouch may be adjusted using the pump based on the measured temperature.

In some variations, the temperature may be a scalp temperature. In some variations, the temperature sensor may be on an external surface of the heat exchanger, within the heat exchanger, or within a fluid channel of the heat exchanger. In some variations, the heat exchanger may comprise one or more fluid channels comprising circulating fluid. In some of these variations, the temperature may be a fluid temperature. In some variations, the temperature sensor may comprise a set of temperature sensors, the temperature may comprise a set of temperatures, and the pouch may comprise a set of chambers, and the method comprises independently adjusting an inflation pressure of each chamber of the pouch based on the set of temperatures.

In some variations, the heat exchanger may be separate from and moveable relative to the inflatable member. In some variations, transitioning the inflatable member from a deflated to an inflated configuration may increase a pressure applied to the head. In some variations, a counter pressure may be generated using the shell when the inflatable member is in an inflated configuration. In some variations, from about 0.1 lb/in$^2$ to about 10 lb/in$^2$ of compression to the head may be generated when the inflatable member is in an inflated configuration. In some variations, the inflatable member may comprise a plurality of independently inflatable chambers.

In some variations, a liner may be placed around the portion of the scalp such that the heat exchanger is between the liner and the inflatable member. In some variations, the heat exchanger may comprise a base portion, a top portion, a first side portion, and a second side portion. The first side portion and the second side portion may be placed over each other. The top portion may be placed over the first side portion and the second side portion so as to surround at least the portion of the scalp.

In some variations, the pouch may comprise a fluid comprising a gas or a liquid. In some variations, a fluid may be circulated through the heat exchanger. The fluid may comprise a temperature of from about −10° C. to about 5° C. In some variations, the compression assembly may be attached to the scalp using a fastener.

In some variations, a cooling cap assembly may comprise a flexible heat exchanger configured to remove heat from a scalp of a patient, an inflatable member releasably coupled to the heat exchanger, an outer shell coupled to the inflatable member, a cooling unit fluidly coupled to the heat exchanger, the cooling unit configured to determine a power source and to circulate fluid through the heat exchanger, and a memory comprising instructions to adjust a fluid flow rate of the cooling unit based on the determined power source. In some variations, the power source may comprise one or more of an AC power source and DC power source.

In some variations, a method of controlling cooling of a scalp of a head of a chemotherapy patient may comprise applying a cooling cap to the head. The cooling cap may comprise a flexible heat exchanger, an inflatable member releasably coupled to the heat exchanger, and a shell coupled to the inflatable member. The method may include the steps of circulating temperature-controlled fluid through the heat exchanger using a cooling unit comprising a plurality of operation states, identifying a power source of the cooling unit, and selecting the operation state of the cooling unit based on the identified power source.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A-7F are perspective views of an illustrative variation of a cooling cap assembly process.

FIG. 12A is a schematic view of an illustrative variation of an inflatable member. FIG. 12B is a bottom view of an illustrative variation of an inflatable member in a first configuration held in an enclosure. FIG. 12C is a bottom view of an illustrative variation of an inflatable member in a second configuration held in an enclosure.

FIGS. 15A-15K are external views of an illustrative variation of a cooling unit. FIGS. 15L-15N are exploded perspective views of an illustrative variation of a cooling unit.

DETAILED DESCRIPTION

Figure 1A:
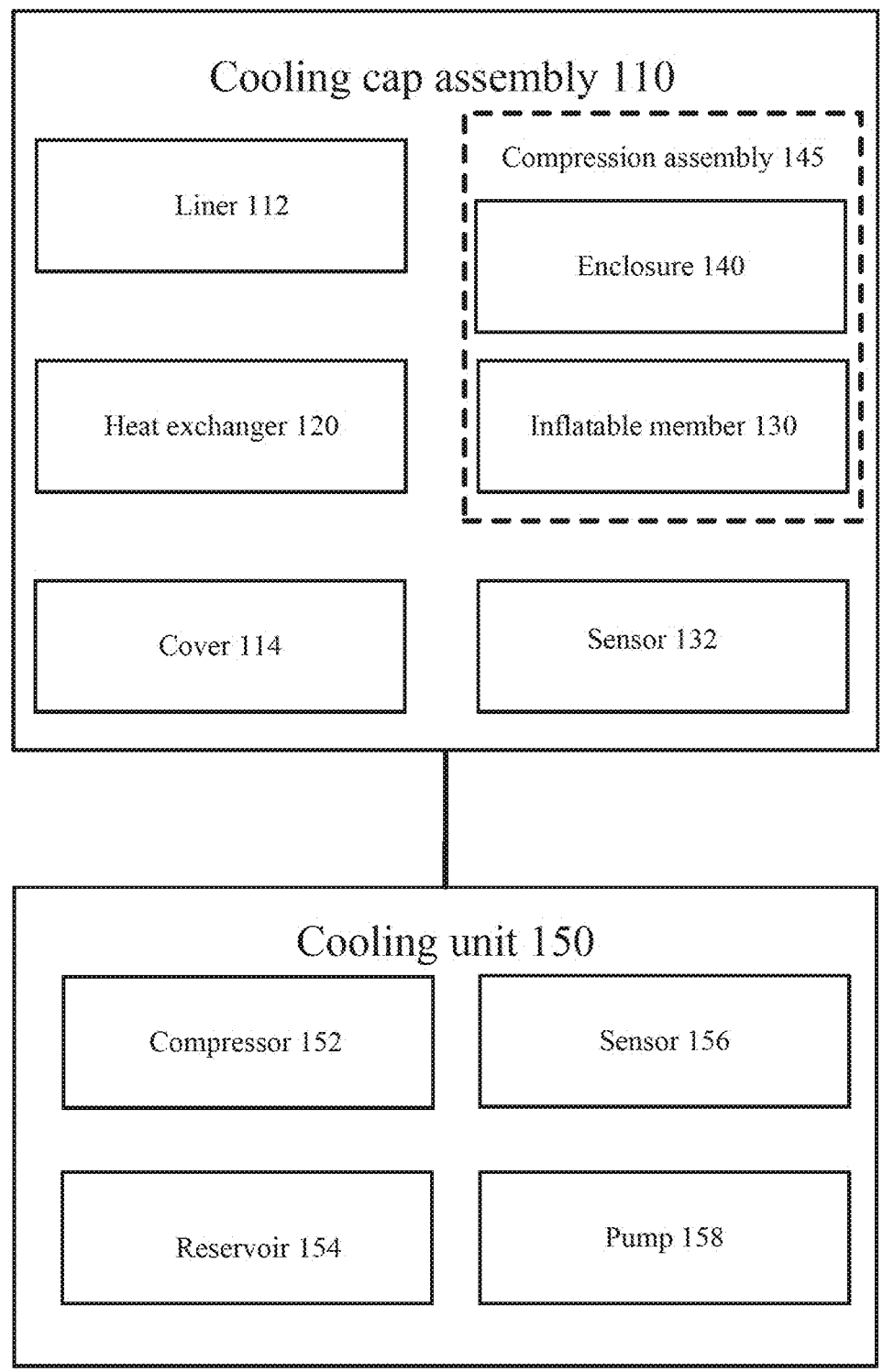
FIGS. 1A and 1C are block diagrams of an illustrative variation of a cooling cap assembly.

Described here are systems and devices for reducing a temperature of a patient's head, and in particular, cooling a scalp of a patient using a cooling cap assembly. A cooling cap assembly may comprise, for example, a heat exchanger configured to remove heat from a scalp of a patient, and a compression assembly separate from and releasably coupled to the heat exchanger. For example, the compression assembly may comprise an inflatable member coupled to a rigid outer shell where the inflatable member may inflate to apply pressure to the heat exchanger and increase a contact area between the heat exchanger and scalp. These systems and devices may generate sensor data to control one or more of a temperature of a cooling fluid and the force applied by the compression assembly placed over the heat exchanger.

Also described here are methods of assembling a cooling cap assembly and using the cooling cap assembly to cool a patient's scalp. Methods of assembling a cooling cap assembly may include wrapping a heat exchanger around a portion of a head and placing a compression assembly over the heat exchanger. The cooling cap assembly may be adjusted to each patient to improve one or more of fit, comfort, and cooling effectiveness or heat transfer. In some variations, the assembled cooling cap assembly may form a friction fit with the compression assembly such that the cooling cap assembly may be removed from a patient's head as a single unit once a treatment session has been completed and optionally reapplied as a single unit for one or more subsequent treatment sessions. Generally, methods of using a cooling cap assembly may comprise circulating fluid through a heat exchanger coupled to a scalp of a patient and controlling an inflation pressure of an inflatable member coupled to the heat exchanger based on one or more temperature and/or force (e.g., pressure) measurements.

Cooling Cap Assembly

The cooling cap assemblies described here may be configured to be placed on a patient's head to remove heat from a patient's scalp. The patient may be able to adjust each portion of the cooling cap assembly to personalize the fit and comfort of the cooling cap assembly. Furthermore, the compression provided by the cooling cap assembly to the head may be adjusted for one or more of cooling effectiveness and patient comfort. Some patients may begin a cooling treatment session within a clinical setting (e.g., infusion center) using the cooling cap assemblies described herein. Moreover, the cooling cap assembly may be portable such that the patient may perform a cooling treatment session outside of a clinical setting (e.g., at home) and/or may begin, continue, or finish a cooling treatment session when traveling to or from a clinical setting (e.g., when traveling from home to a clinical setting or vice versa). The cooling cap assemblies may generally comprise a liner, a flexible heat exchanger, a compression assembly, and a cover. The compression assembly may comprise an inflatable member and an enclosure. For example, the heat exchanger may be separate from and moveable relative to the inflatable member. In some variations, the cooling cap assemblies may comprise and one or more sensors, which may be communicatively coupled (e.g., wired or wirelessly) to a controller.

FIG. 1A is a block diagram of a variation of a cooling system (100) comprising a cooling cap assembly (110) and a cooling unit (150). The cooling cap assembly (110) may be configured to be removeably placed on a scalp of a patient and to decrease the surface temperature of a scalp during, for example, a chemotherapy treatment. As shown there, the cooling cap assembly (110) may comprise a liner (112), a flexible heat exchanger (120), and a compression assembly (145), a cover (114), and one or more sensors (132). The compression assembly (145) may comprise an inflatable member (130) and an enclosure (140). The heat exchanger (120) may generally comprise fluid channels through which fluid may circulate to remove heat from a patient's scalp. The compression assembly (145) may be configured to apply a predetermined force to the heat exchanger to, for example, increase the contact area between the heat exchanger and a patient's scalp, which may increase the heat transfer between the scalp and the fluid circulating in the heat exchanger. For example, the enclosure may provide a counter force to the inflatable member when the inflatable member is in the inflated configuration.

The cooling units described here may be fluidly coupled to the cooling cap assemblies described here to cool the cooling fluid and circulate the cooled fluid through the heat exchanger. For example, the cooling unit may comprise components to cool, store, and pump fluid (e.g., water, alcohol, glycol, a combination thereof) into and out of a cooling cap assembly. Turning back to FIG. 1A, as shown there, the cooling unit (150) may comprise a compressor (152), a reservoir (154), one or more sensors (156), and a pump (158). The compressor (152) may be configured to decrease the temperature of the cooling fluid and the pump (158) may be configured to circulate the cooling fluid through the cooling cap assembly (110) (i.e., through the heat exchanger). The one or more sensors (156) may be communicatively coupled (e.g., wired or wirelessly) to a controller. As will be discussed in more detail herein, the cooling unit (150) may be fluidly coupled to the cooling cap assembly (110) by, for example, a fluid conduit or tubing assembly.

Figure 1B:
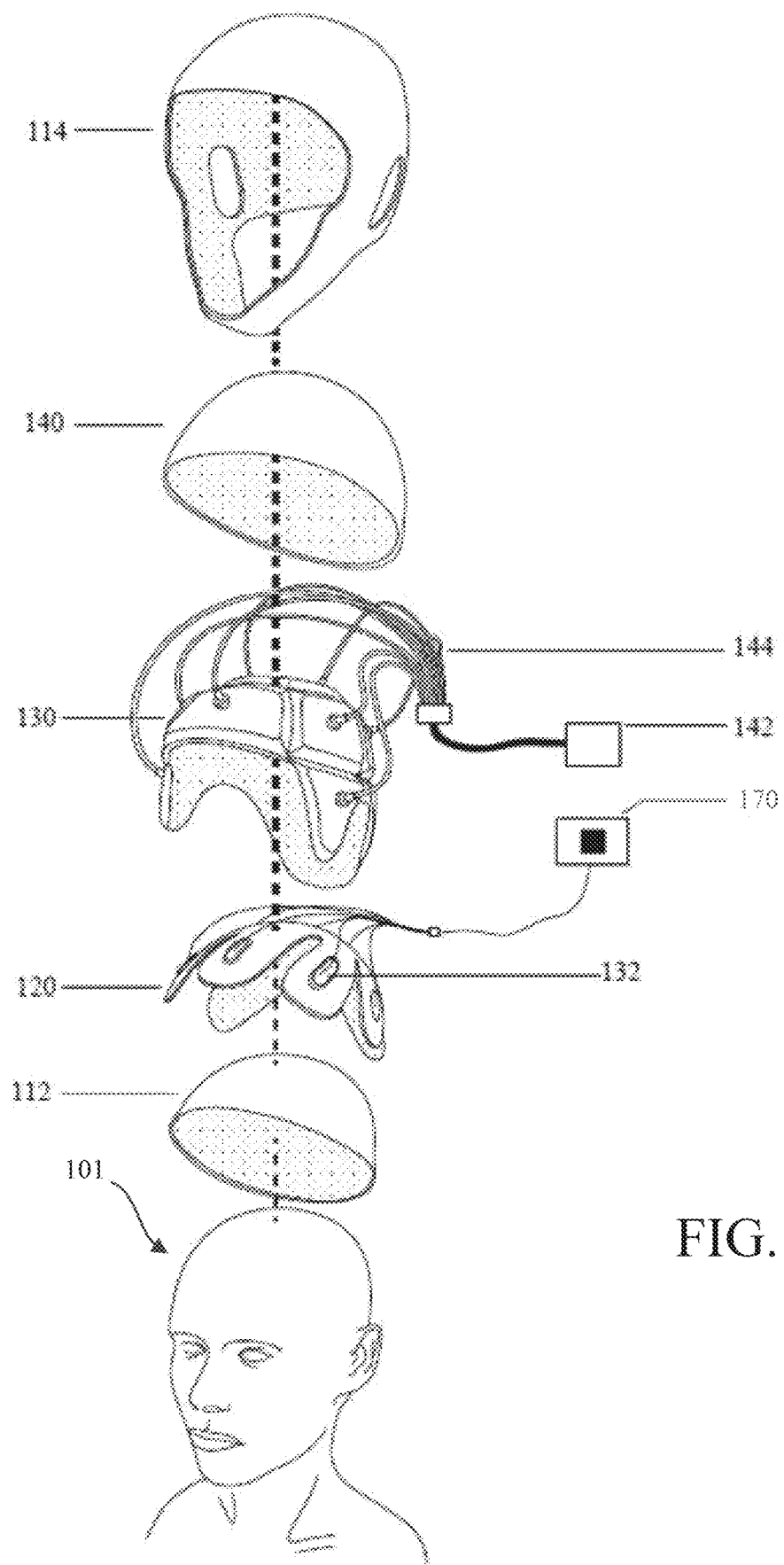
FIG. 1B is an exploded perspective view of an illustrative variation of a cooling cap assembly.

Turning back to the cooling cap assembly (110), FIG. 1B is an exploded perspective view of a variation of the cooling cap assembly (110) configured to be placed on the scalp of a patient (101). The liner (112) may be placed on the scalp and the heat exchanger (120) may be placed over the liner (112) such that a bottom or inner surface of the heat exchanger (120) may be removeably coupled to the scalp through the liner (112). In some variations, the cooling cap assembly (110) may not include the liner (112), and the heat exchanger (120) may be placed directly on the scalp. The compression assembly (145) may be placed over the heat exchanger (120). More specifically, the inflatable member (130), which may be separate from, and moveable relative to, the heat exchanger (120), may be placed over the heat exchanger (120) (e.g., on top of the heat exchanger) such that a bottom or inner surface of the inflatable member (130) contacts a top or outer surface of the heat exchanger (120). As mentioned above, the enclosure (140) may be coupled to a top or outer surface of the inflatable member (130), and thus the enclosure (140) and the inflatable member (130) may be placed on the user's head simultaneously.

In some variations, a cover (114) may be coupled to the enclosure (140) (e.g., to an outer surface of the enclosure (140)) and may be placed on the user's head with the enclosure (140) and the inflatable member (130). In other variations, the cover (114) may be distinct from the enclosure (140) and may be placed over the enclosure (140) and the user's head separately. The cover (114) may comprise a fastener, which may releasably attach the cooling cap assembly to the head of the patient (101). In some variations, the cooling cap assembly may not include a cover (114), and the enclosure (130) may comprise a releasable fastener to couple to cooling cap assembly to the head of the patient (101).

When coupled, the inflatable member (130) may be positioned between the enclosure (140), which may comprise or otherwise serve as an outer shell, and the heat exchanger (120). The heat exchanger (120) may be separate from and moveable relative to the inflatable member (130). In some variations, the inflatable member (130) may comprise a pouch having a top surface and a bottom surface, and the bottom surface may be releasably coupled to the heat exchanger (120). The inflatable member may be coupled to a pump (not shown), and the pump may be configured inflate the pouch. In some variations, the inflatable member (130) may comprise a plurality of chambers, as described in more detail herein, which may be coupled to a pump that may individually or simultaneously inflate the chambers. The inflatable member (130) may comprise a set of fluid conduits (144) (e.g., fluid pressure lines) coupled to one or more valves (142). For example, in variations comprising a plurality of fluid conduits, each fluid conduit may comprise or otherwise be fluidly coupled to a valve. The one or more valves (142) may be coupled to the pump (not shown).

In some variations, transitioning the inflatable member (130) from a deflated configuration to an inflated configuration may increase a pressure applied to the head of patient by the cooling cap assembly and the contact area between the heat exchanger (120) and the head of the patient (101). In some variations, the compression assembly (145) may be configured to generate from about 0.1 lb/in to about 10 lb/in of compression to the head when the inflatable member (130) is in the inflated configuration. In some variations, the compression assembly (145) may be configured to generate from about 0.1 $lb/in^2$ to about 8.0 $lb/in^2$, from about 0.1 $lb/in^2$ to about 5.0 $lb/in^2$, from about 0.1 $lb/in^2$ to about 3.0 $lb/in^2$, from about 0.1 $lb/in^2$ to about 2.0 $lb/in^2$, from about 0.1 $lb/in^2$ to about 1.0 $lb/in^2$, from about 0.5 $lb/in^2$ to about 8.0 $lb/in^2$, from about 0.5 $lb/in^2$ to about 5.0 $lb/in^2$, from about 0.5 $lb/in^2$ to about 3.0 $lb/in^2$, from about 0.5 $lb/in^2$ to about 2.0 $lb/in^2$, or from about 0.5 $lb/in^2$ to about 1.0 $lb/in^2$ of compression to the head when the inflatable member (130) is in the inflated configuration.

In some variations, the cooling system may be a closed-loop system such that one or more parameters of one or more components of the cooling system (e.g., a pump coupled to the inflatable member, a pump circulating the cooling fluid, a compressor of a cooling unit) may be modified based on information received from one or more sensors. For example, in some variations, the heat exchanger (120) may comprise a plurality of temperature sensors (132). The plurality of temperature sensors (132) may be coupled (e.g., via wired or wireless connection) to a controller (170) (e.g., processor, memory). The controller (170) may comprise instructions and/or execute instructions to receive a temperature from a temperature sensor and adjust an output of one or both of the pumps and/or the compressor based on the temperature. In some variations, the controller (170) may be configured to adjust or otherwise control a fluid pressure of the inflatable member (130) using the pump fluidly coupled thereto.

Heat Exchanger

Generally, the heat exchangers described here may be configured to remove heat from a scalp of a patient via a cooling fluid circulating in one or more passages therein. Due to the shape of a patient's head and the geometry of a heat exchanger, a contact area between the patient's scalp and the heat exchanger may be inconsistent and/or suboptimal. For example, the weight and coverage area of the heat exchanger having circulating fluid may not be sufficient to provide the compression forces to evenly cool a patient's scalp, such as when a patient moves their head. In some variations, the contact area between the heat exchanger and the scalp may be increased using a compression assembly as described herein, which may improve the effectiveness of a cooling treatment. In some variations, the shape and dimensions of the heat exchanger may be configured to be adjustable such that the heat exchanger may properly fit patients having varying head shapes and sizes, which may also provide an increased contact area between the heat exchanger and the patient's head to increase effectiveness of a cooling treatment. In some variations, the heat exchanger may comprise a surface that may be comfortably placed directly on a scalp of a patient. For example, the interior surface of the heat exchanger may comprise a terry cloth surface.

Figure 2A:
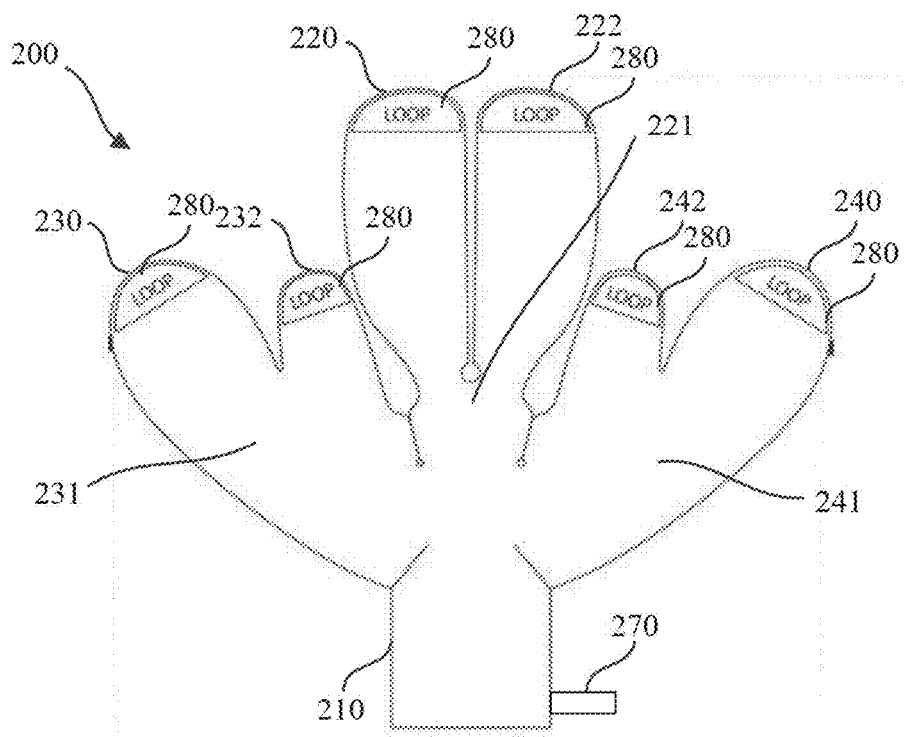
FIGS. 2A, 2B, 2E, 2F, and 2G are schematic views of an illustrative variation of a heat exchanger.
Figure 2B:
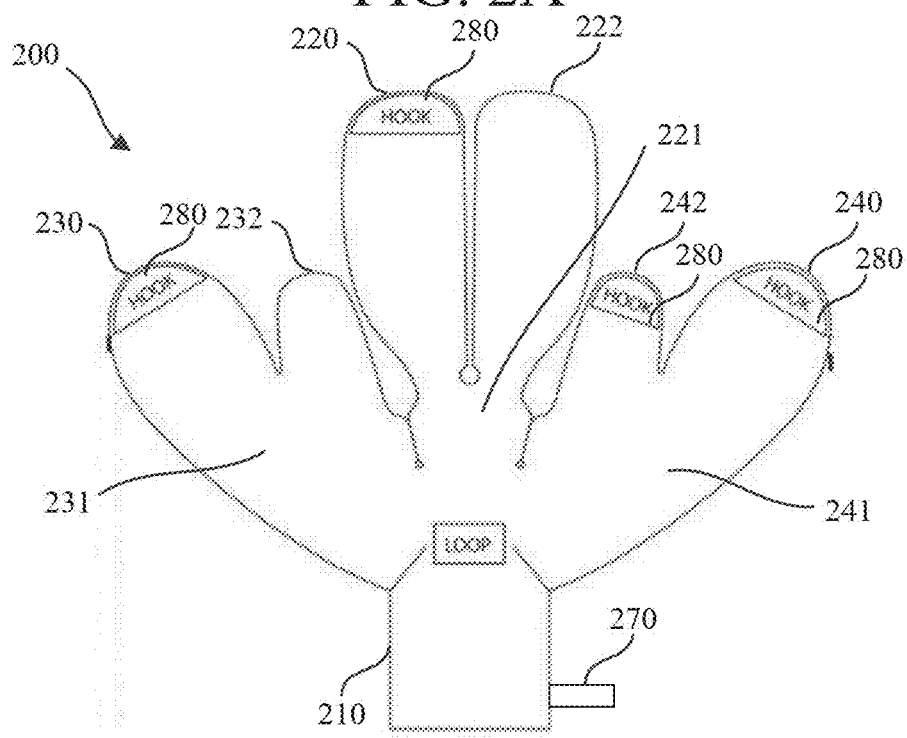

FIGS. 2A and 2B are schematic top and bottom (e.g., exterior and interior) views respectively of a variation of a heat exchanger (200). As shown there, the heat exchanger (200) may comprise a base portion (210), a top portion (221), a first side portion (231), a second side portion (241), and a fluid connector (270). The fluid connector (270) may be used to couple the heat exchanger (200) to a cooling unit and may be coupled to any suitable portion of the heat exchanger (200), for example, any of the base portion (210), the top portion (221), or either side portion (241). The fluid connector (270) may comprise a fluid conduit such as tubing configured to couple to an inlet and an outlet of a cooling unit. The top portion (221) may be configured to cover the top ridge and/or forefront of the head, the base portion (210) may be configured to cover the back of the head and/or the neck, and the first and second side portions (231, 241) may be configured to be cover the left and right hemispheres of the head. The base portion (210) may have a generally rectangular shape and may extend away from the top portion (221).

In some variations, the top portion (221), the first side portion (231) and/or the second side portion (241) may comprise one or more arms or lobes, for example, two, three, four, or more. In some variations, the first side portion (231), the second side portion (241), and the top portion (221) may comprise only two lobes, and the heat exchanger (200) may only comprise a total of six lobes (i.e., the base portion (210) does not have any lobes). The lobes of each portion of the heat exchanger may be sized and shaped to adjustably cover different portions of a patient's head. For example, the lobes may generally be elongate (e.g., have a larger length than width) and may each have a curved or rounded distal end. One or more of the distal ends may comprise a fastener (e.g., hook, loop) used to fasten the lobes to each other. Each lobe may extend from the base (210) and may be flexible so as to allow conformance to a patient's head and for patient adjustment. In variations in which the top portion (221), first side portion (231), and second side portion (241) comprise a plurality of lobes, each lobe in each portion may be the same (e.g., have the same shape, length, width, surface area, and/or radius of curvature of the distal end) or each lobe may be different (e.g., have a different shape, length, width, surface area, and/or radius of curvature of the distal end). For example, in some variations, each of the top portion (221), first side portion (231), and second side portion (241) may comprise two lobes, the lobes (220, 222) in the top portion (221) may have the same length and width as one another, and the length and width of the lobes (220, 222) in the top portion (221) may be different from the length and width of the lobes (230, 232, 240, 242) in the side portions (when length and width of each lobe is measured relative to the proximal end of the heat exchanger (200)). In some instances, one or more lobes (230, 232) in the first side portion (231) may be a mirror image of one or more lobes (240, 242) in the second side portion (241) and/or the lobes (220, 222) in the top portion (221) may be mirror images of one another.

As shown in FIG. 2A, for example, the top and side portions of the heat exchanger (200) may generally form a cactus-like shape or that of a set of splayed fingers. In some variations, the top portion (221) and base portion (210) may define a common longitudinal axis. The first side portion (231) and the second side portion (241) may extend from the base portion (210) at an acute angle with respect to the longitudinal axis. The lobes of the side portions may have different acute angles with respect to the longitudinal axis. In some variations, one or more of the lobes may be tapered. In some variations, the lobes may extend from either another portion of the heat exchanger (e.g., first lobe (230) extends from base portion (210) at an acute angle) or from another lobe (e.g., second lobe (232) extends from first lobe (230)). In some variations, a length of a first lobe to a length of a second lobe may be from about 2:1 to about 0.5:1. In some variations, a width of a first lobe to a width of a second lobe may be from about 2:1 to about 0.5:1.

In the variation depicted in FIGS. 2A-2B, the top portion (221) may comprise a first lobe (220) and a second lobe (222), the first side portion (231) may comprise a first lobe (230) and a second lobe (232), and the second side portion (241) may comprise a first lobe (240) and a second lobe (242). As shown there, the length of the first lobes (230, 240) of the first portion (231) and the second portion (241) may be greater than a length of the second lobes (232, 242) of the first portion (231) and the second portion (241). Additionally or alternatively, the length of the first and second lobes in the first side portion (231) and the second side portion (241) may be less than the length of the first and second lobes in the top portion (221). In some variations, an area of either the first side portion or the second side portion to an area of the top portion is from about 2:1 to about 0.5:1. In some variations, the heat exchanger (200) may comprise a length of from about 30 cm to about 50 cm, and a width of from about 35 cm to about 80 cm.

Figure 2C:
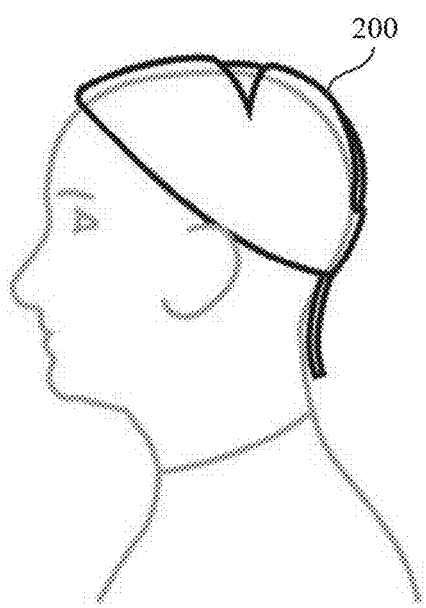
FIGS. 2C and 2D are schematic views of an illustrative variation of a heat exchanger placed on a scalp of a patient.
Figure 2D:
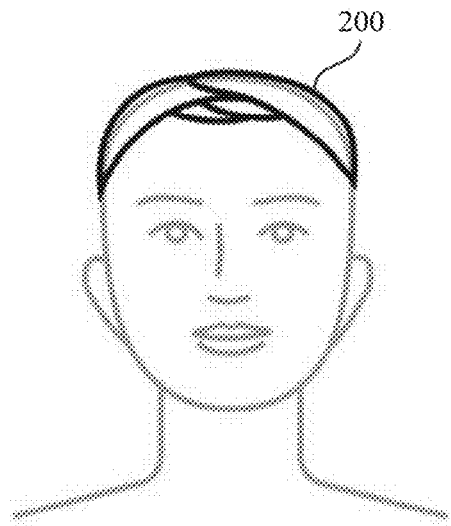
Figure 2E:
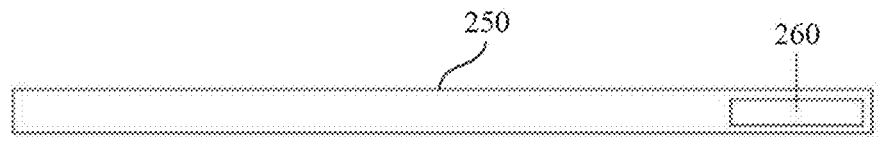
Figure 2F:
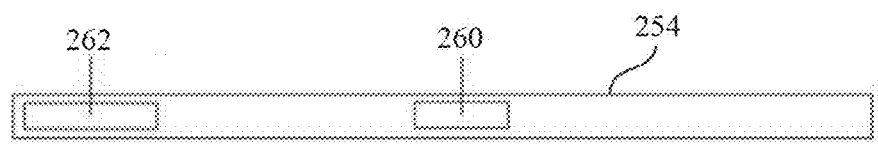
Figure 2G:
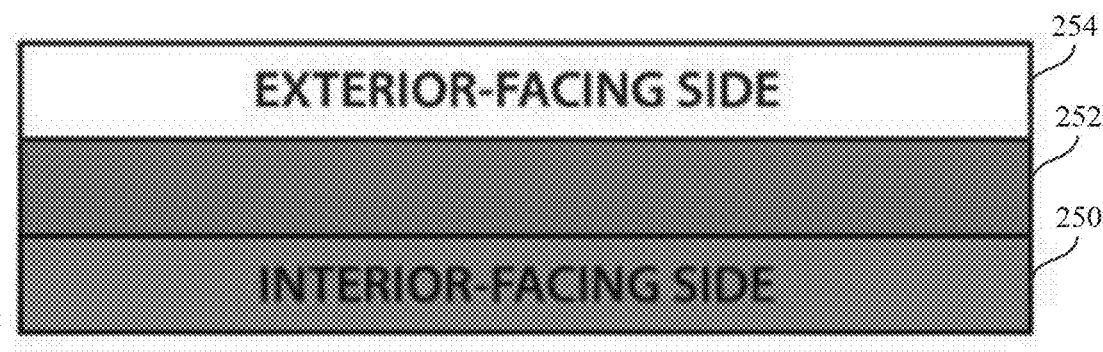
Figure 2H:
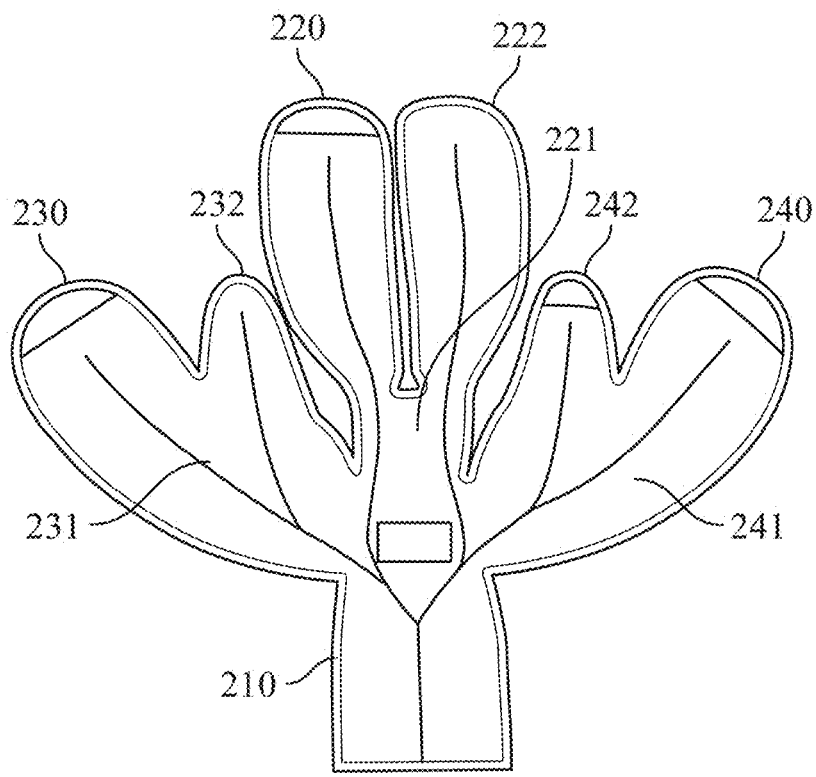
FIGS. 2H-2L are plan views of an illustrative variation of steps in assembling a heat exchanger.
Figure 2I:
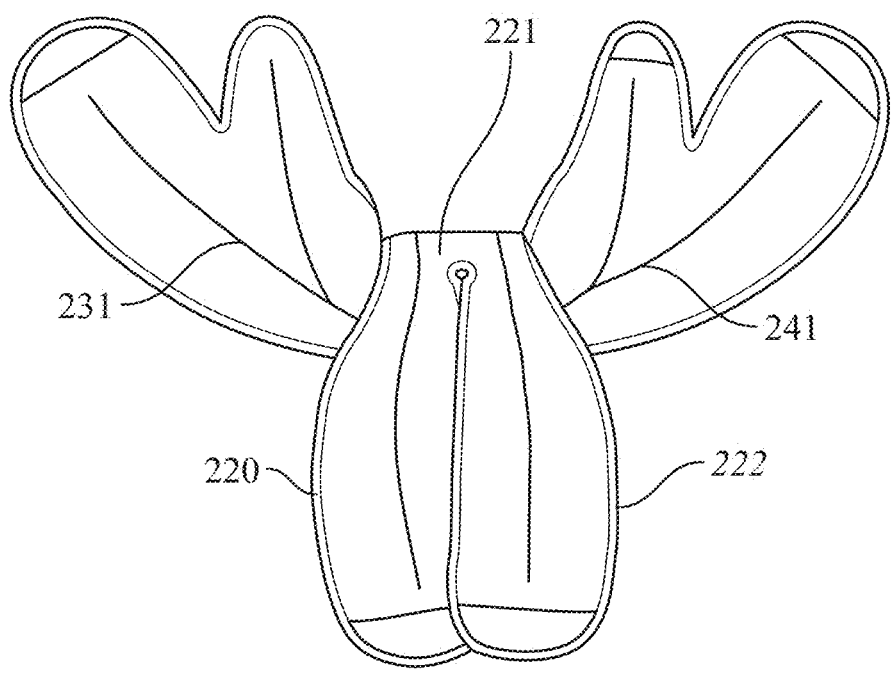
Figures 2J, 2K:
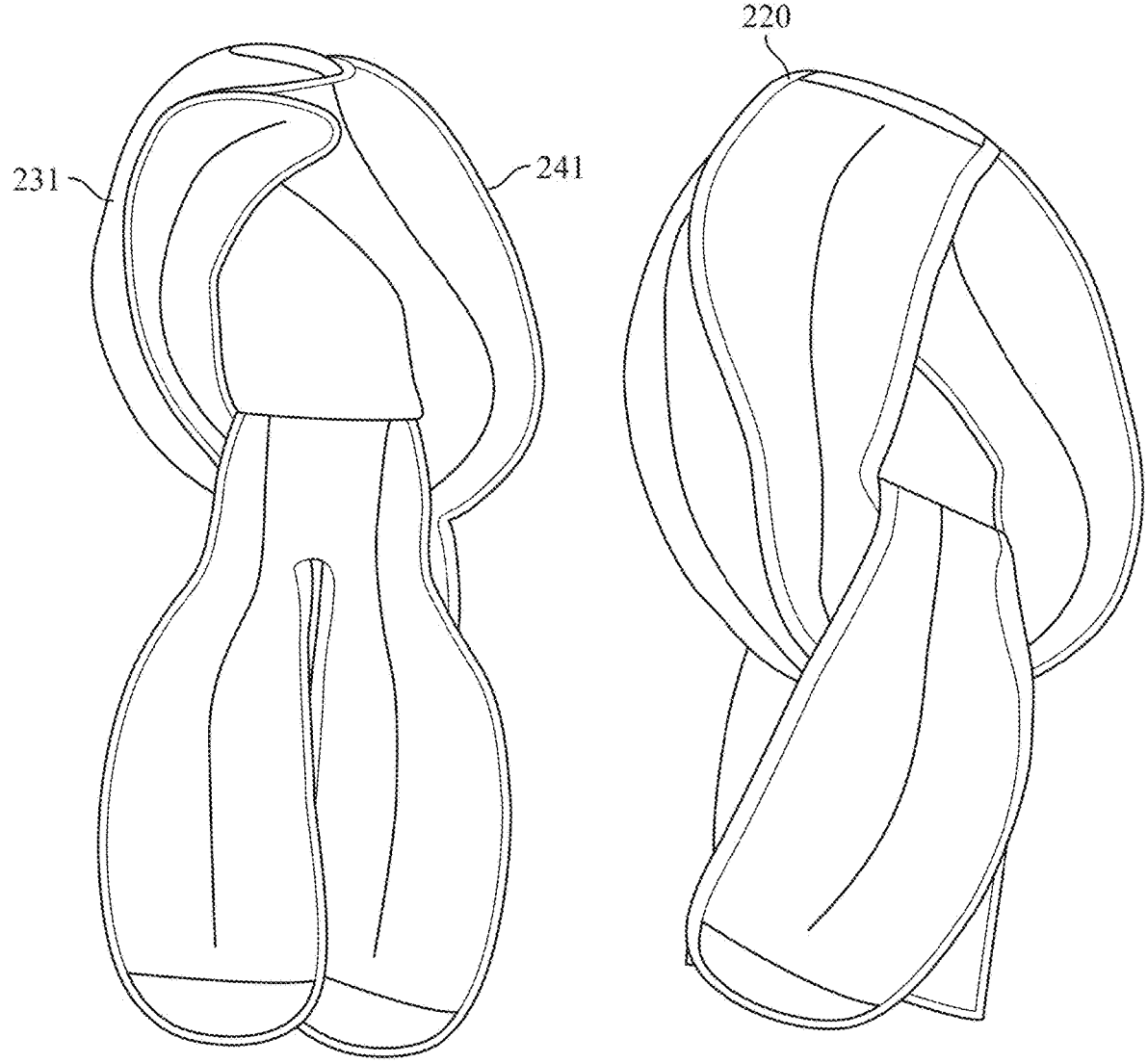
Figure 2L:
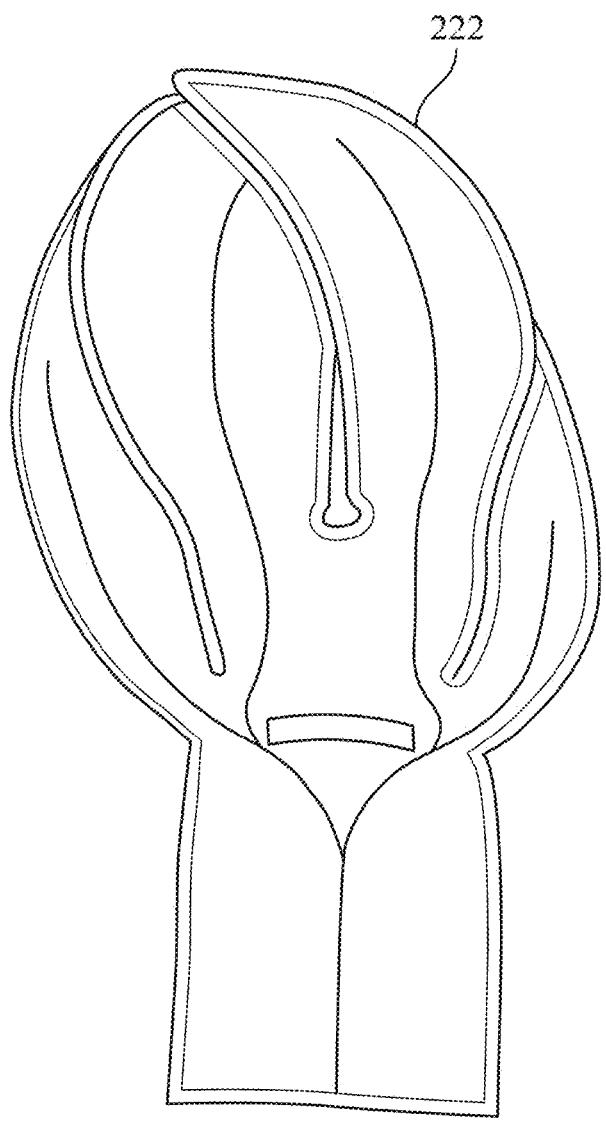
Figure 2M:
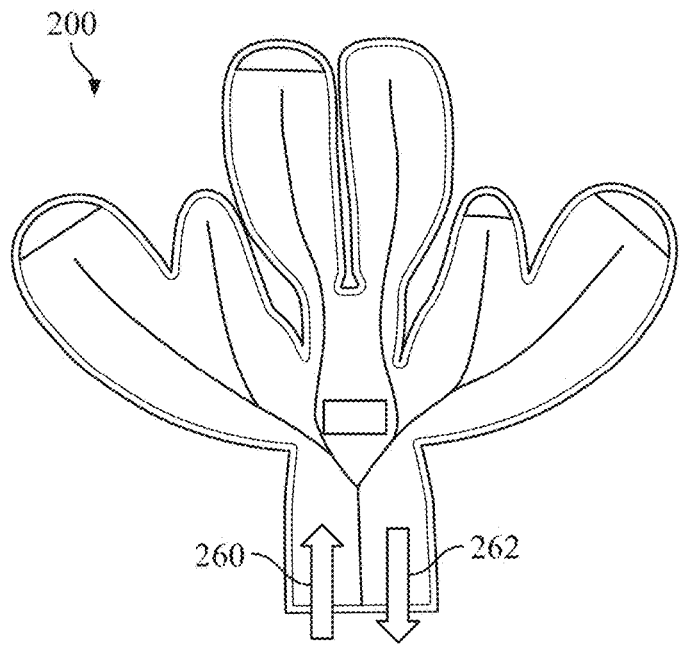
FIG. 2M is a plan view of an illustrative variation of a fluid flow pattern of a heat exchanger.

The heat exchanger (200) may generally comprise one or more fluid channels (not shown) forming a fluid path through at least one of the base portion (210), the top portion (221), the first side portion (231), and the second side portion (241). For example, in some variations, each portion of the heat exchanger (200) may comprise at least a portion of a fluid channel. In some instances, each portion of the heat exchanger (200) comprises a plurality of fluid channels (e.g., two, three, four, or more). The fluid channels may have any size and shape suitable to circulate cooling fluid through the portions of the heat exchange. For example, each fluid channel may comprise a cross-sectional area of from about 9 mm$^2$ to about 100 mm$^2$. When in use, the fluid channels may comprise circulating fluid that may have a temperature that is lower than a temperature of the scalp of a patient. FIG. 2M illustrates one variation of a fluid flow pattern of a heat exchanger (200). In the variation shown there, each lobe of the heat exchanger (200) may comprise two fluid channels and fluid may enter (260) and exit (262) the heat exchanger (200) through a base portion of the heat exchanger (200).

Figure 2N:
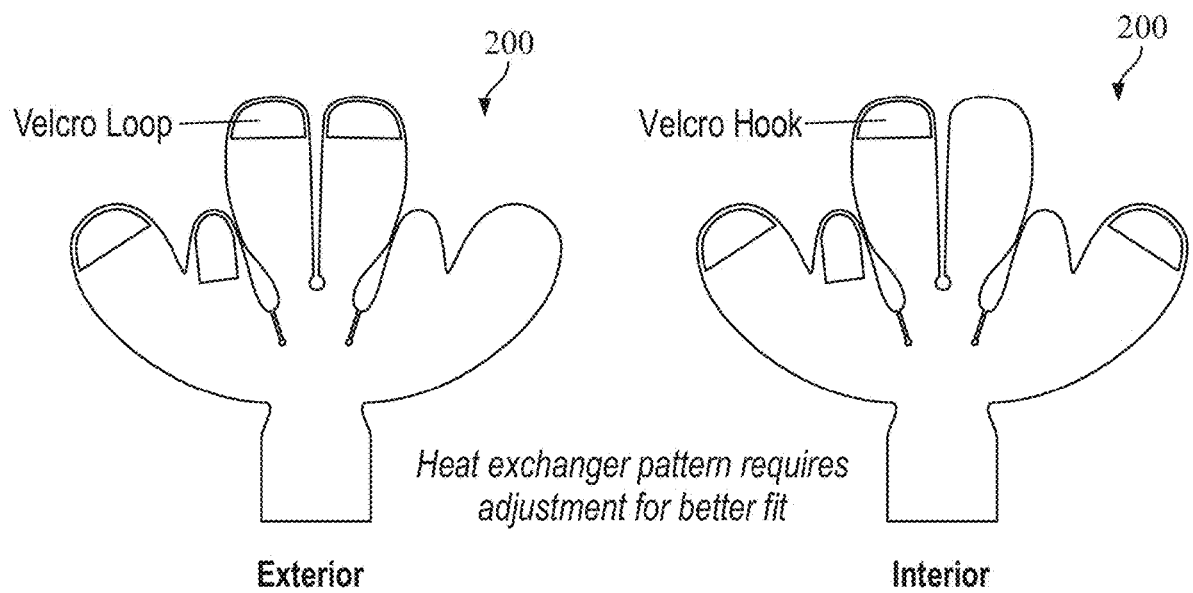
FIG. 2N depicts schematic views of an illustrative variation of fasteners of a heat exchanger.

As shown in at least FIGS. 2A, 2B, and 2N, the heat exchanger (200) may comprise one or more releasable fasteners (280) (e.g., hooks, loops, Velcro®, a combination thereof or the like) configured to form and hold the heat exchanger (200) in a predetermined shape configuration. For example, one or more end portions of the heat exchanger (200) may comprise fasteners having any suitable shape or size. FIGS. 2A and 2B show a set of fasteners (280) coupled to distal ends of the lobes. For example, a semispherical loop fastener may be disposed on a first side of the heat exchanger (200) (FIG. 2A) on a distal end of each lobe. On a second side of the heat exchanger (200) opposite the first side (FIG. 2B), a semispherical hook fastener may be disposed on four of the lobes. Furthermore, a loop fastener may be disposed on the second side of the base portion (210). The portions and/or lobes may be manipulated such that the hooks and loops of different portions may overlap and couple to each other so as to wrap around and secure the heat exchanger to a scalp of a patient.

In some variations, the heat exchanger (200) may comprise a flexible material such as nylon, urethane coated nylon, woven polyester, polyvinyl chloride (PVC), loop fabric, non-woven fabric, combinations thereof and the like. This may allow one or more portions of the heat exchanger (200) to be manipulated and adjusted to conform to a shape of a patient's head and to accommodate patients of various head sizes. As shown in the side and front schematic views of FIGS. 2C and 2D, the heat exchanger (200) may be generally shaped to be wrapped around a head of a patient. For example, one or more end portions of the heat exchanger may be configured to adjustably overlap so as to surround at least a portion of the head, as described herein in more detail with respect to FIGS. 2H-2L.

The heat exchanger (200) may be formed from several layers that may be coupled to one another, one or more of which may form fluid passageways within the heat exchanger. FIG. 2G is a schematic cross-sectional view of a portion of one variation of the layers of a heat exchanger (200). The heat exchanger (200) may comprise a first, bottom layer (250) configured to face a patient and a second, top layer (254) configured to face away from the patient (e.g., face an inflatable member). The first layer (250) and the second layer (254) may form a cavity and/or one or more of fluid channels (depicted schematically as 252) therebetween, which may receive circulating fluid when the heat exchanger is in use. In some variations, the layers of the heat exchanger may be radio frequency or thermally welded to one another to form a circuitous and/or tortuous path for circulating fluid and may be water impermeable. In some variations, the first layer (250) and/or the second layer (254) may comprise a flexible material such as nylon. In some variations, for example, when a liner is not used, the second layer (254) may comprise a soft fabric such as terry cloth and/or absorbent fabric. Additionally or alternatively, in some variations, one or more portions of the heat exchanger (200) (e.g., the first layer (250) or a portion thereof and/or the second layer (254) or a portion thereof) may optionally comprise a compressible material (e.g., an open cell foam, a closed cell foam). In variations comprising a compressible material, the compressible material may be integrated into or embedded within one or more layers of the heat exchanger and/or may be attached to an internal and/or external surface of one or more layers of the heat exchanger (200). Utilizing a compressible material may increase the rigidity of the heat exchanger (200) so as to increase resistance to buckling from, for example, internal liquid pressure and/or may increase a distance between the first layer (250) of the heat exchanger (200) and the patient's scalp, which may reduce the risk of frostbite. FIGS. 2E and 2F are schematic side cross-sectional views of the heat exchanger (200). For example, FIG. 2E illustrates the first layer (250) comprising a hook fastener (260) and the second layer (254) comprising a hook fastener (260) and loop fastener (262).

Figure 11A:
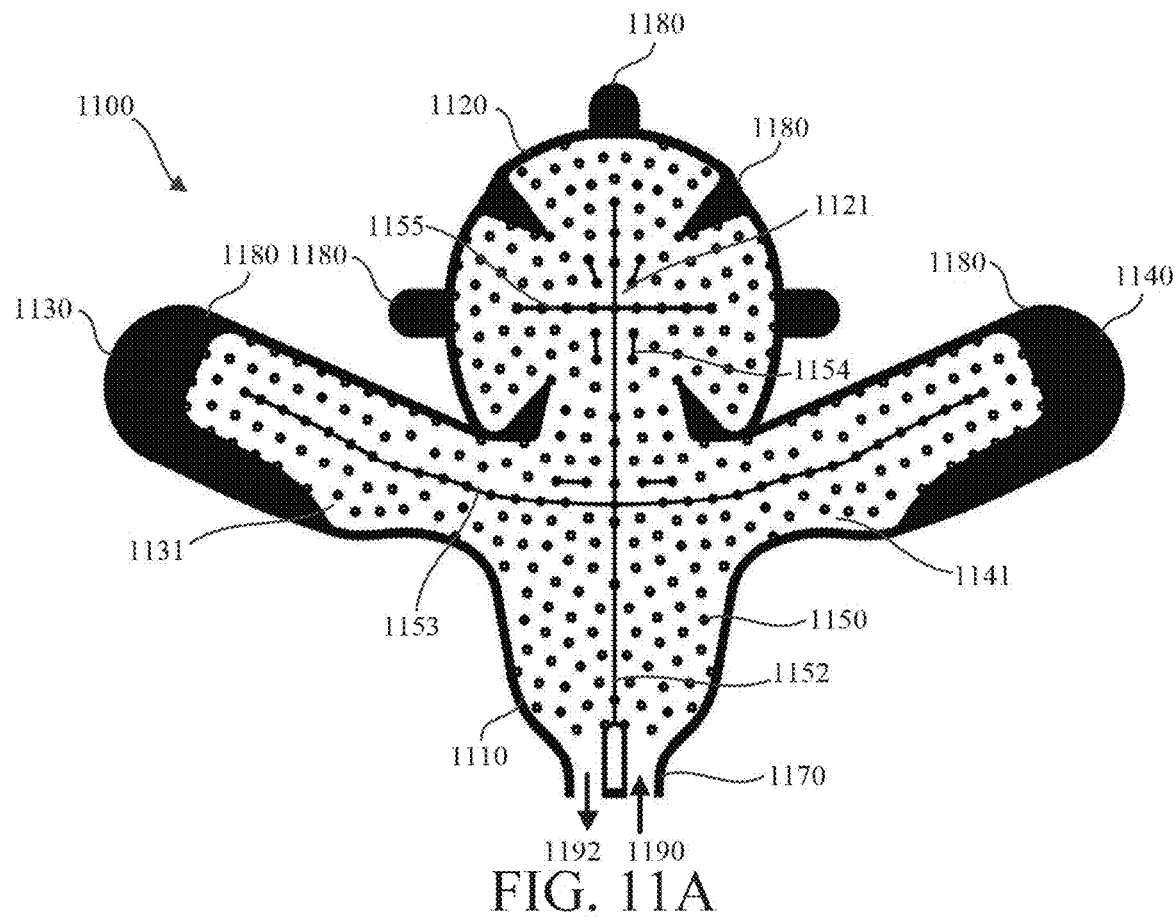
FIGS. 11A and 11B are schematic views of illustrative variations of a heat exchanger.
Figure 11B:
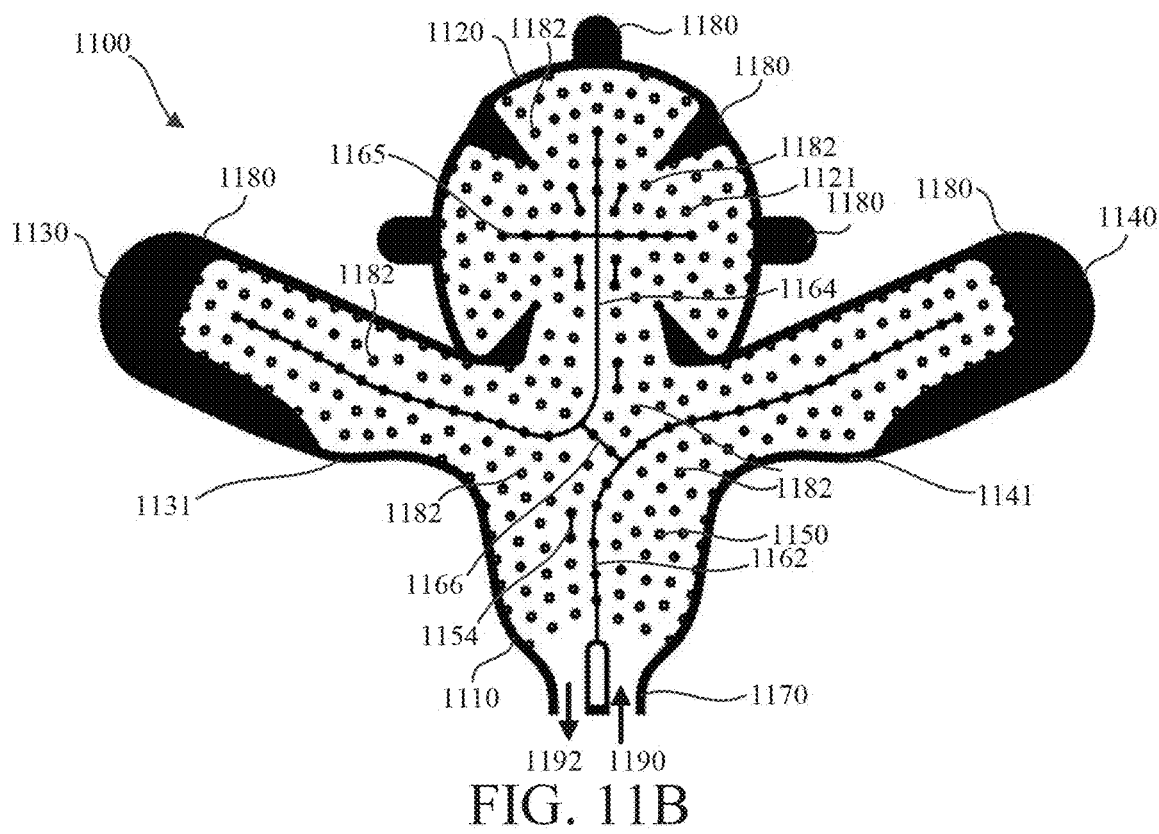

FIGS. 11A and 11B are schematic views of additional variations of a heat exchanger (1100) comprising a design configured for efficient cooling and fluid flow. As shown there, the heat exchanger (1100) may comprise a base portion (1110), a top portion (1121), a first side portion (1131) comprising a first arm (1130), a second side portion (1141) comprising a second arm (1140)), and a fluid connector (1170). Furthermore, one or more portions of the heat exchanger (1100) may comprise one or more fluid barriers (1150, 1152, 1154) (e.g., a plurality of fluid barriers such as two, three, four, five, or more), one or more fasteners (1180), (e.g., a plurality of fasteners such as two, three, four, five or more), and one or more sensors (1182) (e.g., a plurality of sensors such as two, three, four, five or more). The fluid connector (1170) may be configured to couple the heat exchanger (1100) to a cooling unit (not shown) and may be coupled to any suitable portion of the heat exchanger (1100), for example, any of the base portion (1110), the top portion (1121), or either side portion (1131, 1141). The fluid connector (1170) may comprise a fluid conduit such as tubing configured to couple to an inlet and an outlet of a cooling unit. The top portion (1121) may be configured to cover the top ridge and/or forefront of the head, the base portion (1110) may be configured to cover the back of the head and/or the neck, and the first and second side portions (1131, 1141) may be configured to cover the left and right hemispheres of the head. For example, the top portion (1121) may have a generally circular or ellipsoidal shape, the first and second side portions (1131, 1141) may have a generally elongate shape with rounded (e.g., bulbous) ends and the base portion (1110) may have a generally tapered shape and may extend away from the top portion (1121) and side portions (1131, 1141).

In some variations, the top portion (1121), the first side portion (1131) and/or the second side portion (1141) may each comprise one or more arms or lobes, for example, one, two, three, four, or more. In some variations, the first side portion (1131), the second side portion (1141), and the top portion (1121) may comprise three arms or lobes in total, and the heat exchanger (1100) may only comprise a total of three arms or lobes (i.e., the base portion (1110) may not have any arms). The arms of each portion of the heat exchanger may be sized and shaped to adjustably cover different portions of a patient's head. For example, the arms of each of the first and second side portions may generally be elongate (e.g., have a larger length than width) and may each have a curved or rounded distal end. The top portion (1121) may have a generally circular or ellipsoidal shape in the shape of a head. One or more of the distal ends may comprise a fastener (e.g., hook, loop) used to fasten the arms to one another. Each arm may extend outward from the base (1110) in opposing directions and may be flexible so as to allow conformance to a patient's head and for patient adjustment. In variations in which the top portion (1121), first side portion (1131), and second side portion (1141) each comprise a plurality of arms, each arm in each portion may be the same (e.g., have the same shape, length, width, surface area, and/or radius of curvature of the distal end) or each arm may be different (e.g., have a different shape, length, width, surface area, and/or radius of curvature of the distal end).

Figure 11C:
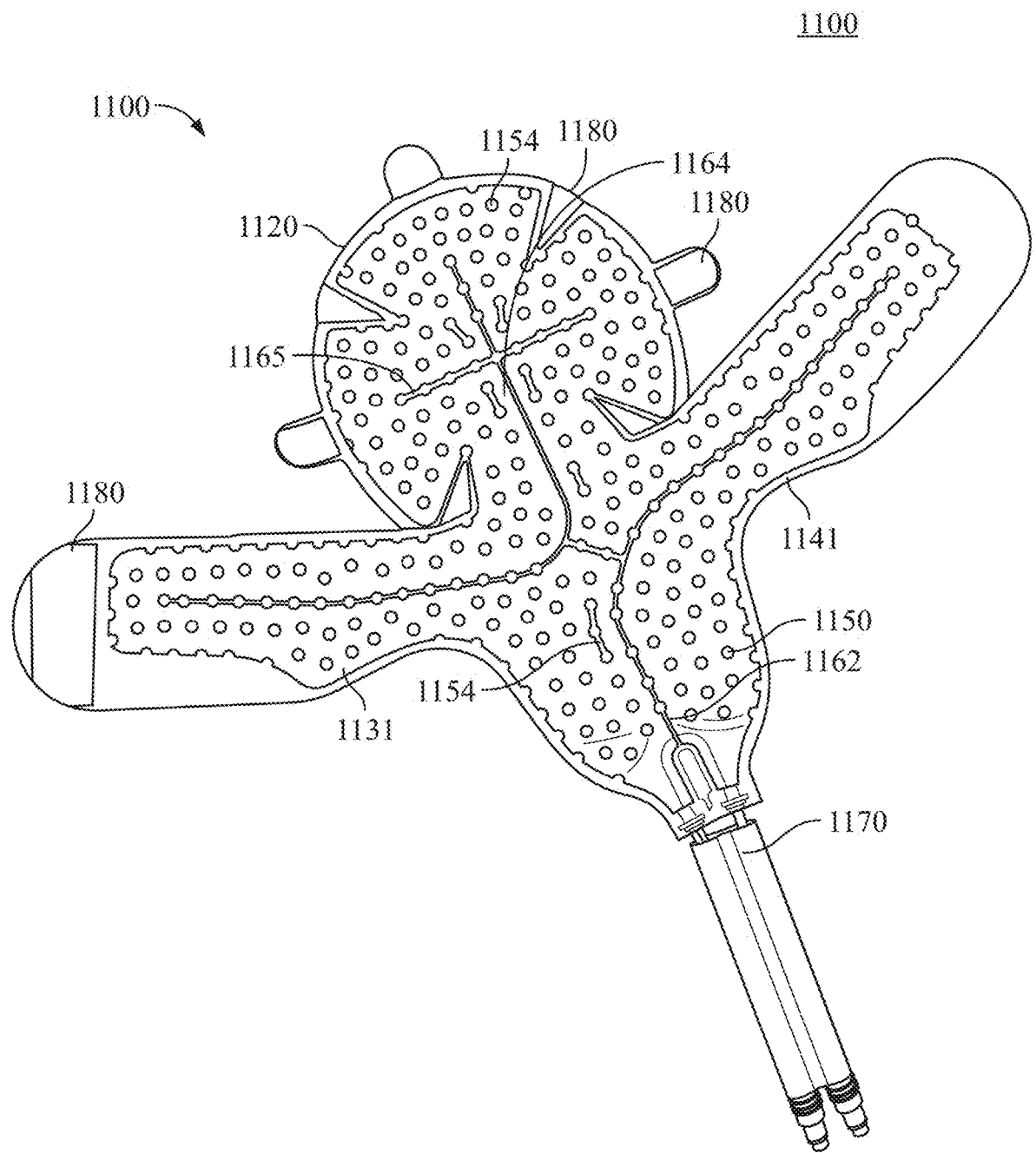
FIG. 11C is an image of an illustrative variation of a heat exchanger.

As shown in FIGS. 11A-11C, for example, the top and side portions of the heat exchanger (1100) may generally form one or more of a humanoid shape (e.g. scarecrow), T-shape, and/or cross shape. In some variations, the top portion (1121) and base portion (1110) may define a common longitudinal axis, and in some instances, the fluid barrier (1152) may generally extend along the common longitudinal axis (e.g., the fluid barrier (1152) may generally extend along a longitudinal axis of the heat exchanger (1100)). The first side portion (1131) and the second side portion (1141) may extend from the base portion (1110) at an acute angle with respect to the longitudinal axis. In some variations, the first side portion (1131) and the second side portion (1141) may form a generally curved shape relative to the base portion (1110). For example, the side portions may extend from the base portion (1110) at the same or at different arcuate angles with respect to the longitudinal axis. In some variations, one or more of the arms may be tapered (e.g., proximal end has a larger width than distal end, distal end has a larger width than a proximal end). In some variations, the arms may extend from either another portion of the heat exchanger (e.g., first arm (1130) extends from base portion (1110) at an acute angle) or from another arm (e.g., second arm (1140) extends from top portion (1121)). For example, the first arm (1130) and the second arm (1140) may form an angle from about zero degrees to about 80 degrees relative to the longitudinal axis. In some variations, a ratio of the length of a first arm to the length of a second arm may be from about 2:1 to about 0.5:1. In some variations, a ratio of the width of a first arm to the width of a second arm may be from about 2:1 to about 0.5:1.

In some variations, the heat exchanger (1100) may comprise a length of from about 30 cm to about 50 cm, including all sub-ranges and values in-between, for example, from about 35 cm to about 45 cm. In some variations, the heat exchanger (1100) may comprise a width of from about 35 cm to about 80 cm, including all sub-ranges and values in-between. In some variations, a ratio of a length of an arm to a diameter of the top portion may be from about 3:2 to about 3:4. For example, in some variations, the top portion (1121) may comprise a diameter of about 20 cm, and the base portion (1110) may comprise a length of about 20 cm, and each side portion (1131, 1141) may comprise a length of about 25 cm.

The heat exchanger (1100) may generally comprise a fluid path (e.g., fluid channels) through at least one of the base portion (1110), the top portion (1121), the first side portion (1131), and the second side portion (1141). For example, in some variations, each portion of the heat exchanger (1100) may comprise at least a portion of a fluid path. The fluid path may have any size and shape suitable to circulate cooling fluid through the portions of the heat exchanger (1100). When in use, the fluid path may comprise circulating fluid that may have a temperature that is lower than a temperature of the scalp of a patient. FIGS. 11A and 11B illustrate variations of a fluid flow pattern (1190, 1192) of a heat exchanger (1100). In the variations shown there, fluid may enter (1190) and exit (1192) the heat exchanger (1100) through the base portion (1110) (e.g., at a proximal end of the base portion (1110)) of the heat exchanger (1100). For example, fluid may flow in a generally counter-clockwise direction sequentially through the base portion (1110), second side portion (1141), top portion (1120), first side portion (1131), and out through the base portion (1110).

In some variations, a heat exchanger (1100) may comprise a fluid barrier configured to direct fluid flow through the heat exchanger (1100) and to provide a predetermined shape to the heat exchanger (1100) in an expanded configuration. The fluid barriers described herein may aid in promoting even and consistent cooling and may reduce pooling of fluid within the heat exchanger (1100). For example, the fluid barriers may be configured to reduce turbulent fluid flow throughout the heat exchanger (1100) by defining a predetermined fluid flow path. Furthermore, the fluid barriers may be configured to reduce expansion of one or more portions of a heat exchanger (1100). In some variations, the heat exchanger (1100) may comprise a set of fluid barriers (1150, 1152, 1154) including, but not limited to, point fluid barriers, elongate fluid barriers, rounded fluid barriers, and shaped fluid barriers. For example, the fluid barriers may include one or more of a sidewall and weld within an interior cavity of the heat exchanger (1100) which does not include the walls defining the outer perimeter (e.g., boundary) of the heat exchanger (1100). For example, each barrier may be coupled between opposing layers (e.g., top layer, bottom layer) of the heat exchanger (1100) such that when the heat exchanger (1100) is in an expanded configuration (e.g., filled with fluid), the heat exchanger (1100) may maintain a predefined thickness and shape throughout rather than "ballooning" out. As described in more detail herein, one or more of the fluid barriers may be formed by a welding process.

In some variations, an elongate fluid barrier (1152, 1153, 1155) may define a fluid flow path through one or more portions and/or arms of the heat exchanger (1100) and may provide a predetermined shape to the heat exchanger (1100). For example, FIG. 11A illustrates that a longitudinal elongate fluid barrier (1152) may bisect each of the base portion (1110) and the top portion (1121). Similarly, lateral elongate fluid barriers (1153, 1155) may bisect the first side portion (1131) and the second side portion (1141), and the top portion (1121), respectively. In FIG. 11A, the longitudinal elongate fluid barrier (1152) may form a cross-like shape with each of the lateral elongate fluid barriers (1153, 1155) so as to form a circuitous fluid path through the heat exchanger (1100). One or more elongate fluid barriers (1154) shorter than the longitudinal or lateral elongate fluid barriers (1152) may be disposed in close proximity to the intersections formed between the lateral and longitudinal elongate fluid barriers (1152, 1153, 1155) in order to reduce fluid back pressure (e.g., pooling) in those regions. The elongate fluid barriers (1154) may be generally parallel or angled relative to the lateral or longitudinal elongate fluid barriers (1154).

FIG. 11B illustrates curved elongate fluid barriers (1162) configured to promote non-turbulent or laminar fluid flow near, for example, intersections and/or curved portions of the heat exchanger (1100). FIG. 11C is an image of the heat exchanger (1100) depicted schematically in FIG. 11B. The elongate fluid barriers (1162, 1164) depicted in FIGS. 11B and 11C may comprise one or more curves to reduce fluid back pressure and turbulent flow. Elongate fluid barriers may form a circuitous fluid path through the heat exchanger (1100). For example, FIG. 11B illustrates that a first elongate fluid barrier (1162) that extends through the base portion (1110) and the second side portion (1141). A second elongate fluid barrier (1164) extends through the first side portion (1131) and the top portion (1120). The first and second elongate fluid barriers (1162, 1164) may be coupled by third elongate fluid barrier (1166). A lateral elongate fluid barrier (1165) may form a cross-like shape with respect to the second elongate fluid barrier (1164). One or more elongate fluid barriers (1154) shorter than the first and second elongate fluid barriers (1162,1164) may be disposed in close proximity to the intersections formed between the first, second, third, and lateral elongate fluid barriers (1162, 1164, 1165, 1166) in order to reduce fluid back pressure (e.g., pooling) in those regions. The elongate fluid barriers (1154) may be generally parallel or angled relative to the elongate fluid barriers (1162, 1164, 1165, 1166).

In some variations, the set of fluid barriers may comprise a fluid barrier pattern of spaced-apart fluid barriers (1150) configured to define a fluid flow path and provide a predetermined shape to the heat exchanger (1100). For example, FIGS. 11A and 11B illustrate a set of fluid barriers (1150) comprising a torus-like (e.g., donut, dot, cylinder) shape that may be distributed generally evenly throughout a cavity of the heat exchanger (1100). The center (e.g., hole) of the torus-like fluid barriers are not in fluid communication with the fluid in the heat exchanger. In some variations, one or more of the torus-like fluid barriers (1150) may comprise a diameter of from about 5 mm to about 10 mm and may be spaced apart from other fluid barriers (1150) from about 5 mm to about 15 mm. For example, in some variations, one or more (e.g., a plurality, all) of the torus-like fluid barriers (1150) may comprise a diameter of about 7 mm, and the spacing between the torus-like fluid barriers may be at least 10 mm (e.g., about 10 mm). In some variations, the set of tori (1150) may be generally evenly spaced apart. Each fluid barrier of the set of fluid barriers (1150) may have the same or different diameters. Additionally or alternatively, the set of fluid barriers (1150) may comprise other shapes such as a hemisphere, rectangle, triangle, rhomboid, trapezoid, and other polygon, or a combination thereof (e.g., a plurality of fluid barriers may comprise a first shape (e.g., a torus-like shape) and a plurality of fluid barriers may comprise a second, different shape (e.g., a solid circular shape).

In some variations, one or more (e.g., a plurality, two, three, four, or more) fluid barriers (e.g., fluid barrier (1154)) may comprise a barbell or dumbbell-like shape having a torus-like or circular fluid barrier (or point barriers) coupled to each end of an elongate fluid barrier. These fluid barriers (1154) may be configured to direct fluid flow in a predetermined manner. For example, the elongate fluid barriers (1152, 1154) may promote laminar fluid flow near intersections and sharp angles to reduce fluid back pressure (e.g., pooling, dead spots). Fluid that is relatively stagnant within the heat exchanger (1100) may comprise a relatively higher temperature that may reduce one or more of efficiency and performance of the cooling cap assembly. Thus, elongate fluid barriers may enable non-turbulent flow throughout the heat exchanger (1100). In some variations, the elongate fluid barrier (1152, 1153, 1154, 1162, 1164, 1165, 1166) may be linear or curved, and may comprise a width equal to or less than a diameter or width of the fluid barrier ends (e.g., torus-like fluid barrier, point barrier).

As described in more detail herein, in some variations, the heat exchanger (1100) may comprise one or more sensors (1182), such as, for example, one or more sensors configured to measure temperature. For example, a sensor (1182) may be disposed within the inner "donut hole" (e.g., through hole) of the torus-like fluid barriers (1150) at one or more (e.g., two, three, four, or more) predetermined locations within the heat exchanger (1100), as indicated in FIG. 11B. In some variations, a notification may be generated when one or more measured temperatures is outside a predetermined temperature range or other criteria. For example, in some variations, a patient may be notified if a temperature at one sensor differs from one or more other sensors by a predetermined amount (e.g., 2° C. or more temperature differential).

Additionally, in some variations, the heat exchanger (1100) may comprise one or more releasable fasteners (1180) (e.g., hooks, loops, Velcro®, a combination thereof or the like) configured to form and hold the heat exchanger (1100) in a predetermined shape configuration. For example, one or more end portions of the heat exchanger (1100) may comprise fasteners (1180) having any suitable shape or size. FIGS. 11A and 11B show a set of fasteners (1180) coupled to distal ends of the arms. For example, a semispherical loop fastener may be disposed on a first side of the heat exchanger (1100) on a distal end of each arm. On a second side of the heat exchanger (1100) opposite the first side, a semispherical hook fastener may be disposed on a set of the arms. Furthermore, a loop fastener may be disposed on the second side of the base portion (1110). In some variations, the fasteners (1180) of the top portion (1120) may comprise a triangular shape to allow the top portion (1120) to form a concave or "bowl" shape when the heat exchanger (1100) is in the expanded configuration. For example, FIGS. 11A-11C depict a set of four triangular shaped fasteners (e.g., Velcro®) and three tab-shaped fasteners on a top portion (1120) of the heat exchanger (1100).

In some variations, the portions and/or arms may be manipulated such that the hooks and loops of different portions may overlap and couple to each other so as to wrap around and secure the heat exchanger to a scalp of a patient. For example, the fasteners (1180) on the distal ends of the side portions (1130, 1140) may be wrapped around the side of the patient's head to meet (e.g., couple, overlap) over a patient's forehead. Then, the tab-shaped fasteners (1180) protruding from the top portion (1120) may be coupled to the fasteners (1180) of the side portions (1131, 1141) to secure the top portion (1120) to the side portions (1131, 1141).

In some variations, the heat exchanger (1100) may comprise a flexible material such as nylon, urethane coated nylon, woven polyester, polyvinyl chloride (PVC), loop fabric, non-woven fabric, combinations thereof and the like. This may allow one or more portions of the heat exchanger (1100) to be manipulated and adjusted (e.g., wrapped) to conform to a shape of a patient's head and to accommodate patients of various head sizes.

In some variations, the heat exchanger (1100) may be formed from several layers that may be coupled to one another, one or more of which may form one or more fluid passageways (e.g., fluid paths) within the heat exchanger. For example, the heat exchanger (1100) may comprise a first layer configured to face a patient and a second layer configured to face away from the patient (e.g., face an inflatable member). In some variations, the layers of the heat exchanger may be radio frequency or thermally welded to one another to form a circuitous fluid path for circulating fluid and may be water impermeable. For example, radiofrequency welding may comprise passing electricity using a manufacturing device through the portion of the heat exchanger to be welded. Localized heat and pressure applied by the manufacturing device may create a strong weld (e.g., bond). In some variations, the heat exchanger (1100) may comprise a fabric laminated with thermoplastic polyurethane (TPU).

In some variations, the heat exchanger (1100) may comprise a flexible material such as nylon and/or non-woven fabric. Additionally or alternatively, in some variations, one or more portions of the heat exchanger (1100) may optionally comprise a compressible material (e.g., an open cell foam, a closed cell foam). In variations comprising a compressible material, the compressible material may be integrated into or embedded within one or more layers of the heat exchanger and/or may be attached to an internal and/or external surface of one or more layers of the heat exchanger (1100) which may increase resistance to buckling from, for example, internal liquid pressure and/or reduce the risk of frostbite.

Compression Assembly

The compression assemblies described herein may be configured to increase a contact area between a heat exchanger and a scalp of a patient (in some variations, the contact may be through a liner), which may increase the cooling efficiency of the cooling cap assembly. The compression assemblies described here may generally comprise an inflatable member and an enclosure, and may be separate from and moveable relative to the heat exchanger. Put another way, the compression assembly may be formed separately from the heat exchanger and may be removed or otherwise physically separated from the heat exchanger, for example, during application of the heat exchanger to a patient's scalp. When in use, an interior surface of the inflatable member may contact the heat exchanger and an exterior surface of the inflatable member may contact the enclosure. As the inflatable member is inflated, the enclosure may be configured to resist deformation from the inflatable member and provide a counter force such that the compression assembly may apply a compressive force to the heat exchanger. This compressive force may increase a contact area between the heat exchanger and the scalp, by for example, pressing the heat exchanger into a patient's scalp such that the heat exchanger better conforms to the shape of the patient's scalp. For example, the contour and shape of a patient's scalp may be such that the arms or lobes of a heat exchanger may not fully contact all or a substantial portion of the scalp unless pressure is applied to push the arms or lobes towards the scalp. This application of pressure may allow any voids, gaps, divots, etc. between the heat exchanger and the scalp to be reduced. In some variations, the compression assembly may comprise one or more sensors.

Inflatable Member

Figure 3A:
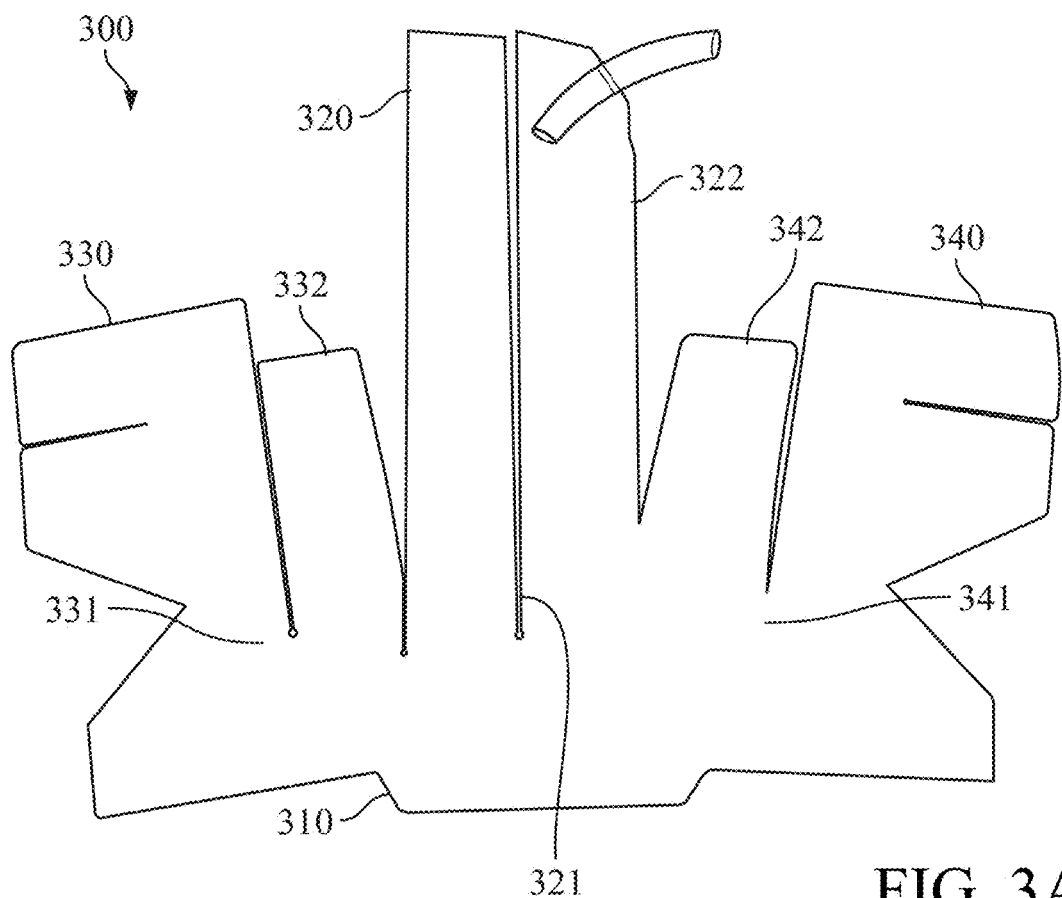
FIGS. 3A and 3B are plan views of an illustrative variation of an inflatable member.
Figure 3B:
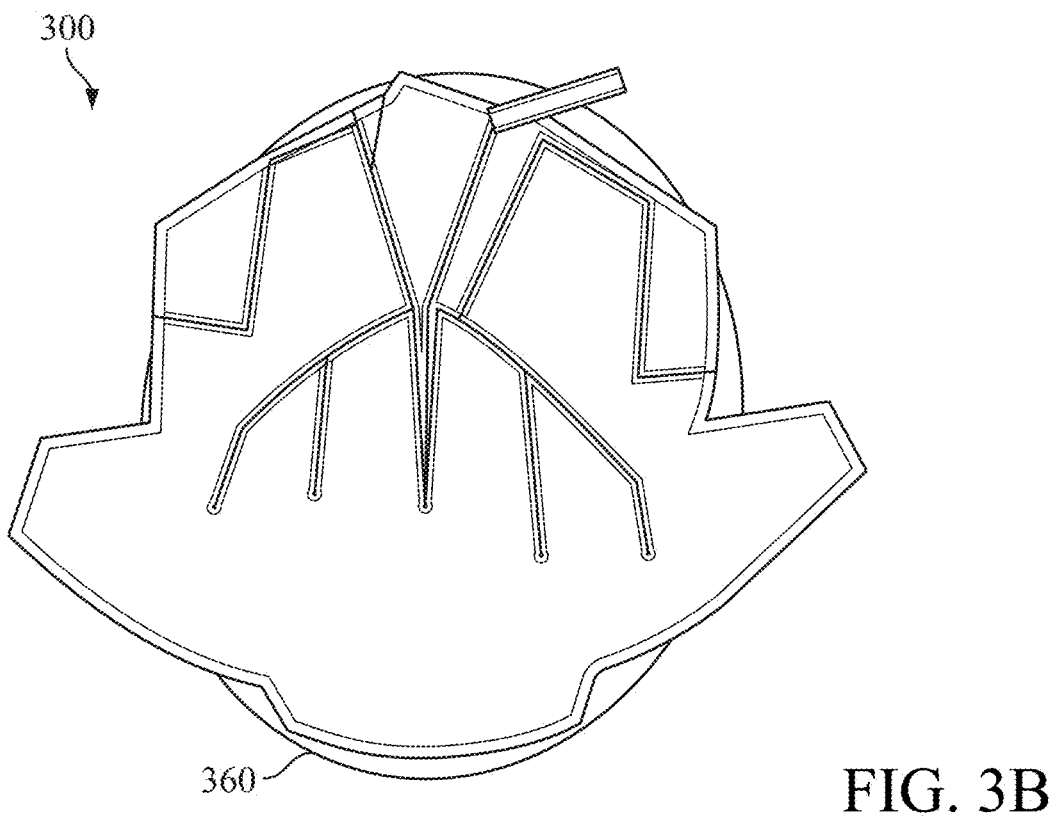

The inflatable members described here may be configured to receive a fluid to transition from a deflated configuration to an inflated configuration in order to increase a force applied by the heat exchanger to the head of a patient. FIGS. 3A and 3B are plan views of a variation of an inflatable member (300). The inflatable member (300) may comprise a base inflatable portion (310), a top inflatable portion (320, 322), a first inflatable side portion (330, 332), and a second inflatable side portion (340, 342). The base inflatable portion (310) may be aligned with the neck and/or rear head of the patient with the top inflatable portion (321) laid over the top ridge and/or forefront of the head. When placed on a patient's head, the side portions (331, 341) may drape over the left and right hemispheres of the head. Each portion may comprise at least one chamber configured to be filled with a fluid (e.g., liquid, gas (e.g., air)). For example, the inflatable member may comprise a plurality of chambers (e.g., two, three, four, five, or more). For example, in one variation, the inflatable member may comprise a front central chamber, a front left chamber, a front right chamber, a top chamber, a back central chamber, a back right chamber, and a back right chamber. In some variations, each of the plurality of chambers may be independently inflatable. As mentioned above, the inflatable member (300) may comprise a deflated configuration and an inflated configuration. When in use on the head of a patient, transitioning the inflatable member (300) from the deflated to the inflated configuration may increase a pressure applied to the head of the patient.

In some variations, a length of the first inflatable side portion (330, 332) and the second inflatable side portion (340, 341) may be less than a length of the top inflatable portion (320, 322). Similar to the heat exchangers described herein, portions of the inflatable member (300) may be configured to adjustably overlap so as to surround at least a portion of the head. For example, FIGS. 3B and 3D are top and perspective views of variations of an inflatable member (300) held in an enclosure (360). The side and top portions of the inflatable member (300) may overlap one another so as to form a generally hemi-spherical shape. In some variations, the inflatable member (300) may be removeably coupled to the enclosure (360). In other variations, the inflatable member (300) may be fixed to the enclosure (360).

The inflatable member (300) may comprise one or more fluid connectors (e.g., tubing) coupled to one or more of the inflation portions (310, 321, 331, 341). In some variations, the inflatable member (300) may further comprise a manual pump fluidly coupled to the one or more chambers of the inflatable member (300) via the fluid connector(s). In other variations, the inflatable member may be fluidly coupled to a separate pump, for example, an air pump contained in the cooling unit, via the one or more fluid connectors. In some variations, one or more of the fluid conduits may comprise a valve that may be used to control or assist in controlling the inflation pressure.

Figure 3C:
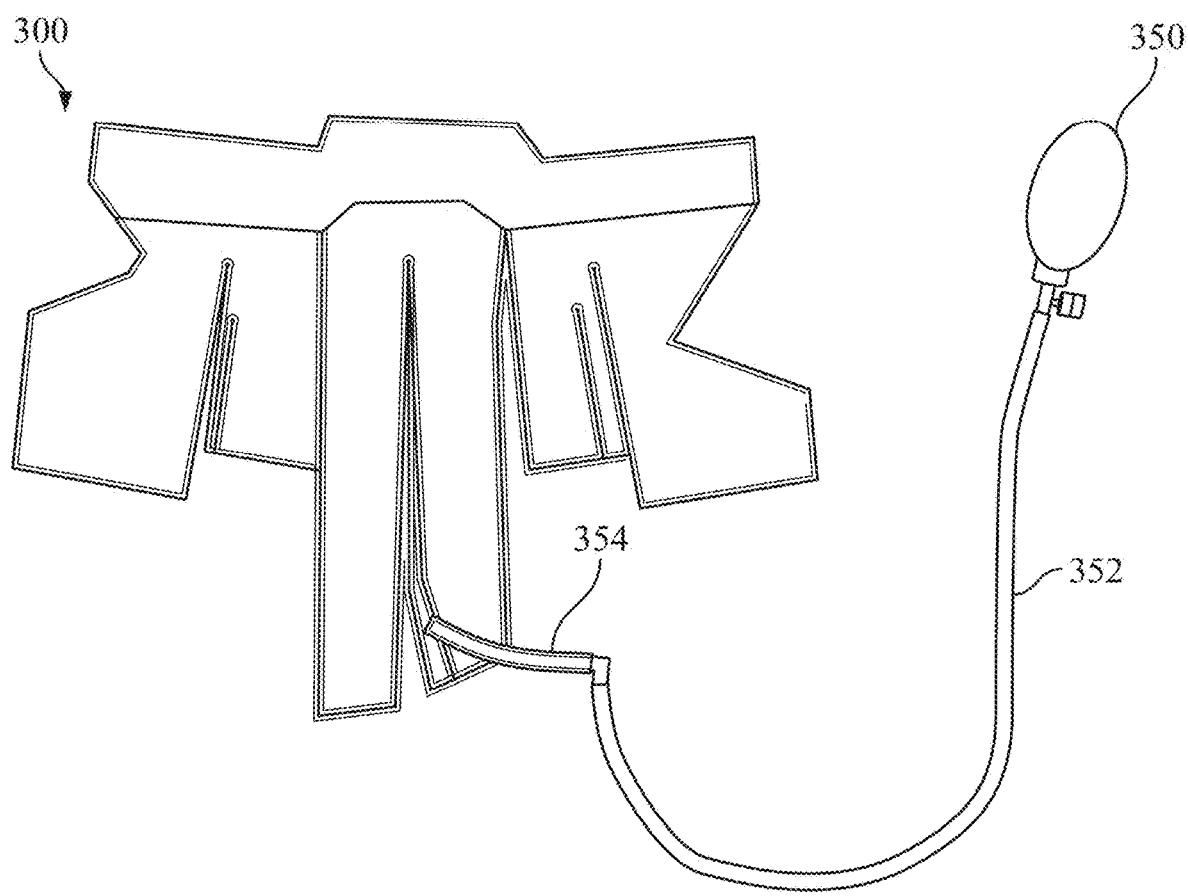
FIG. 3C is a plan view of an illustrative variation of an inflatable member and a pump.
Figure 3D:
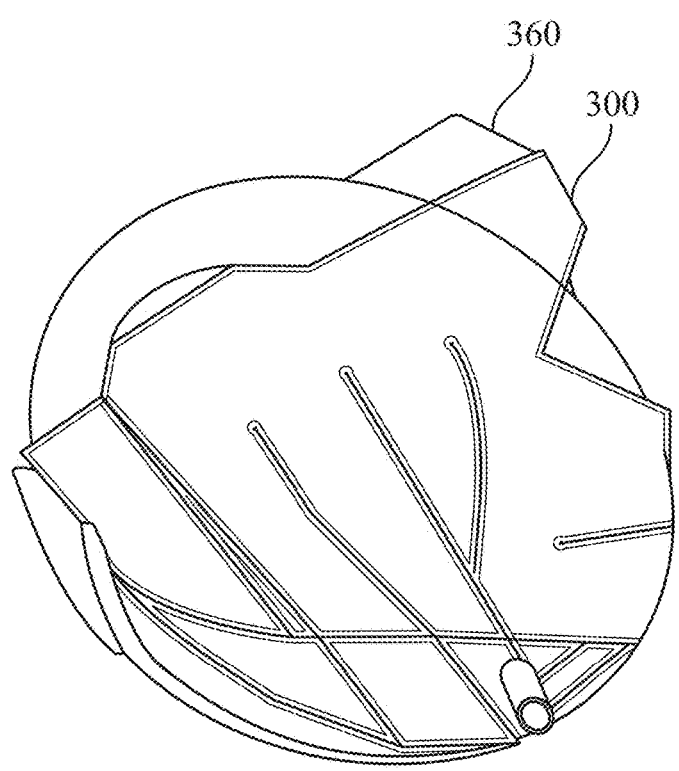
FIG. 3D is a perspective view of an illustrative variation of an inflatable member held in an enclosure.

FIG. 3C depicts a variation of an inflatable member 300 comprising a fluid pump (e.g., air bulb) (350). The fluid pump (350), shown there as manual hand pump (e.g., an air pump bulb), may be coupled to a fluid connector (354) via flexible tubing (352). The flexible tubing (352) may fluidly couple the one or more chambers in the inflation portions (310, 321, 331, 341) to the fluid pump (350) such that the fluid pump (350) may be actuated to fill one or more chambers of the inflatable member (300) to a predetermined pressure (inflation pressure) with, for example, air and/or an inert gas. In some variations, the fluid pump (350) may be actuated by the patient, which may allow the patient to adjust the force applied by the compression assembly to the patient's head via the heat exchanger. This may allow for increased adjustability and comfort of the cooling cap assembly, and may allow for a degree of contact between the heat exchanger and the scalp. As mentioned above, in some variations, the cooling unit may comprise the fluid pump (350). In these variations, the cooling system may further comprise a controller that may be configured to manually (e.g., via user input) and/or dynamically (e.g., using sensor data) control an inflation pressure of the inflatable member (300) using the fluid pump (350).

Figure 12D:
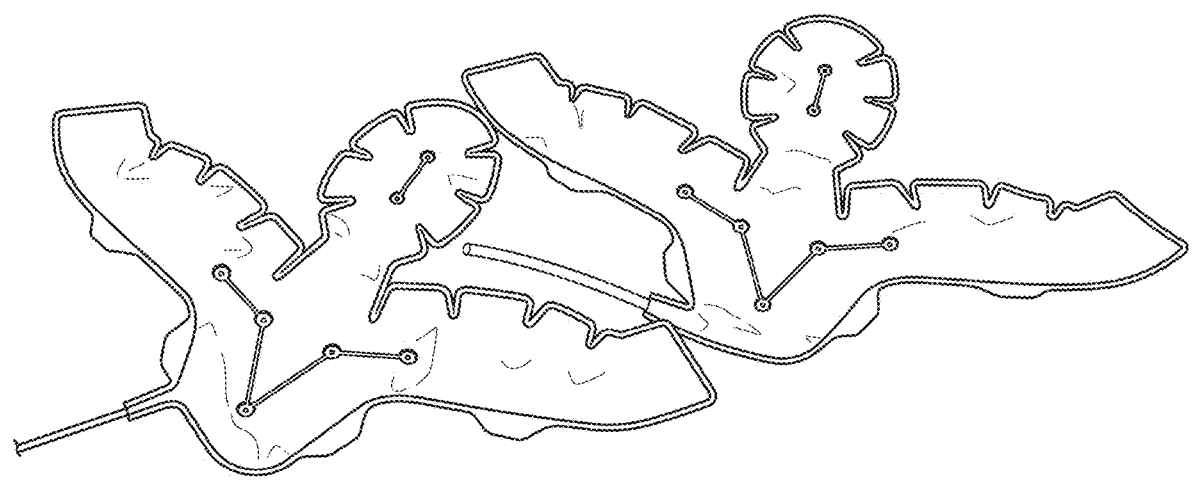
FIG. 12D is an image of illustrative variations of an inflatable member in a first and a second configuration.

In some variations, an inflatable member may be configured to conform to the shape of a patient's head when inflated and held in an enclosure such as a cooling cap. FIG. 12A is a schematic view of another variation of an inflatable member (1200). FIG. 12B is a bottom view of a variation of an inflatable member (1200) in a first configuration (e.g., uninflated configuration) when held in an enclosure. FIG. 12C is a bottom view of an illustrative variation of an inflatable member in a second configuration (e.g., inflated configuration) when held in an enclosure. Similarly, FIG. 12D is an image of illustrative variations of an inflatable member in respective first and second configurations.

The inflatable member (1200) depicted in FIGS. 12A-12D may comprise a base inflatable portion (1210), a top inflatable portion (1220) (e.g., top chamber (1221)), a first inflatable side portion (1230) (e.g., left chamber (1231)), and a second inflatable side portion (1240) (e.g., right chamber (1241)), fluid barriers (1250), fluid connector (1270), slits or voids (1242), and fasteners (1280). The base inflatable portion (1210) may be aligned with the neck and/or rear head of the patient with the top inflatable portion (1221) laid over the top ridge and/or forefront of the head. When placed on a patient's head, the inflatable side portions (1230, 1240) may cover over the left and right hemispheres of the head. Each portion may comprise at least one chamber configured to be filled with a fluid (e.g., liquid, gas such as air). For example, the inflatable member (1200) may comprise a plurality of chambers (e.g., two, three, four, five, or more). For example, in one variation, the inflatable member (1200) may comprise a left chamber (1231), a right chamber (1241), and a top chamber (1221). As mentioned above, the inflatable member (1200) may comprise a first deflated configuration, a second inflated configuration, and a plurality of partially-inflated configurations in-between. When in use on the head of a patient, transitioning the inflatable member (1200) from the first deflated configuration to the second inflated configuration may increase a pressure applied to a heat exchanger and the head of the patient.

In some variations, the top portion (1220) may have a generally ellipsoidal or circular shape. The first and second side portions (1230, 1240) (e.g., wings, arms) may have a generally elongate shape that may be concave to form a "bowl" shape. The base portion (1210) may have a generally tapered shape and may extend away from the top portion (1220). In some variations, a length of the first inflatable side portion (1230) and the second inflatable side portion (1240) (along a respective longitudinal axis) may be more than a length of the top inflatable portion (1220) (along a longitudinal axis of the top inflatable portion). Similarly to the heat exchangers described herein, portions of the inflatable member (1200) may be configured to adjustably overlap so as to surround at least a portion of the head. For example, FIGS. 12B and 12C are top views of variations of an inflatable member (1200) held in an enclosure (1260). The side portions (1230, 1240) and top portion (1220) of the inflatable member (1200) may overlap one another so as to form a generally hemi-spherical shape. In some variations, the inflatable member (1200) may be removeably coupled to the enclosure (1260). In other variations, the inflatable member (1200) may be fixed to the enclosure (1260). When held in the enclosure (1260) in the inflated configuration, the inflatable member (1260) may be configured to apply a generally even amount of pressure to the head of a patient. In some variations, the inflatable member (1200) may comprise one or more slits (1242), voids, or indents to aid in the folding, shaping, and/or overlapping of different portions of the inflatable member (1200) within an enclosure (1260).

In some variations, the top portion (1220) and base portion (1210) may define a common longitudinal axis that bisects the inflatable member (1200). The first side portion (1230) and the second side portion (1240) may extend from the base portion (1210) at an acute angle with respect to the longitudinal axis. For example, the first side portion (1230) and the second side portion (1240) may form an angle from about zero degrees to about 80 degrees relative to the longitudinal axis. In some variations, the ratio of a length of a first portion to a length of a second portion may be from about 2:1 to about 0.5:1. For example, the first portion and the second portion may be mirror images of one another. In some variations, a ratio of the width of a first portion to the width of a second portion may be from about 2:1 to about 0.5:1.

In some variations, the inflatable member (1200) may comprise a length from about 25 cm to about 50 cm, including all sub-ranges and values in-between, such as, for example, from about 30 cm to about 40 cm. In some variations, the heat exchanger (1200) may comprise a width of from about 35 cm to about 80 cm, from about 50 cm to about 70 cm, from about 60 cm to about 70 cm, including all sub-ranges and values in-between.

In some variations, one or more portions of the inflatable member (1200) may comprise one or more fluid barriers (1250). In some variations, the inflatable member (1200) may comprise a set of fluid barriers (1210) (e.g., walls, welds) configured to provide a predetermined shape to the inflatable member (1200) in an inflated configuration. The fluid barriers described herein may aid in promoting even and consistent inflation of the inflatable member (1200). For example, the fluid barriers may be configured to reduce expansion of one or more portions of an inflatable member (1200). Each barrier may be coupled between opposing layers (e.g., top layer, bottom layer) of the inflatable member (1200) such that when the inflatable member (1200) is in an inflated configuration (e.g., filled with fluid), the inflatable member (1200) may maintain a predefined thickness and shape throughout rather than "ballooning" out. This may aid patient comfort and increase cooling efficiency. One or more of the fluid barriers may be formed by a welding process a described herein. In some variations, one or more of the fluid barriers (1250) may be elongate and may generally extend through a mid-point of a chamber. That is, the fluid barriers (1250) may be disposed within an interior cavity of the inflatable member. For example, a fluid barrier (1250) may be linear and/or form a "V"-like shape.

In some variations, one or more portions of the inflatable member (1200) may comprise one or more releasable fasteners (1280) (e.g., hooks, loops, Velcro®, a combination thereof or the like) configured to form and hold the inflatable member (1200) in a predetermined shape configuration. The inflatable member (1200) may be manipulated such that the hooks and loops of different portions may overlap and couple to each other so as to wrap around and secure the inflatable member within an enclosure. One or more edges of the inflatable member (1200) may comprise a fastener (e.g., hook, loop) used to fasten the portions to each other. Each side portion may extend from the base portion (1210) and may be flexible so as to allow conformance to a patient's head and for patient adjustment.

A fluid connector (1270) may be used to couple the inflatable member (1200) to a pump (not shown) and may be coupled to any suitable portion of the inflatable member (1200), for example, any of the base portion (1210), the top portion (1220), or either side portion (1230, 1240). The fluid connector (1270) may comprise a fluid conduit such as tubing configured to couple to a pump. In some variations, the inflatable member (1200) may further comprise a manual pump fluidly coupled to the one or more chambers of the inflatable member (1200) via the fluid connector(s). In other variations, the inflatable member may be fluidly coupled to an air pump contained in the cooling unit, via the one or more fluid connectors. In some variations, one or more of the fluid conduits may comprise a valve that may be used to control or assist in controlling the inflation pressure.

In some variations, one or more chambers of the inflatable member (1200) may be inflated to a predetermined pressure (inflation pressure) with, for example, air and/or an inert gas. In some variations, A fluid pump may be actuated by the patient, which may allow the patient to adjust the force applied by the compression assembly to the patient's head via the heat exchanger. This may allow for increased adjustability and comfort of the cooling cap assembly, and may allow for a degree of contact between the heat exchanger and the scalp. As mentioned above, in some variations, the cooling unit may comprise the fluid pump. In these variations, the cooling system may further comprise a controller that may be configured to manually (e.g., via user input) and/or dynamically (e.g., using sensor data) control an inflation pressure of the inflatable member (1200) using the fluid pump (1250).

In some variations, the inflatable member (1200) may comprise a flexible material such as nylon, urethane coated nylon, woven polyester, polyvinyl chloride (PVC), loop fabric, non-woven fabric, combinations thereof and the like. This may allow one or more portions of the inflatable member (1200) to be manipulated and adjusted (e.g., wrapped) to conform to a shape of a patient's head and to accommodate patients of various head sizes. In some variations, the inflatable member (1200) may comprise a flexible material such as nylon and/or non-woven fabric.

In some variations, one or more inflation portions and/or chambers of the inflatable member may be independently inflated and/or deflated. As shown in FIG. 1B, for example, the inflatable member may comprise a plurality of segmented chambers that may be independently inflated and/or deflated. In these variations, a fluid conduit (144) may be coupled to each chamber of the inflatable member (130) to allow independent control of the fluid pressure in each inflatable portion and/or chamber of the inflatable member. This may allow for more uniform cooling of the head by allowing for individual adjustment of the inflation pressure of each inflation portion and/or chamber as necessary. For example, after an initial inflation of each chamber to a predetermined inflation pressure, temperature sensors coupled to each arm or lobe of the heat exchanger may measure temperature readings that indicate uneven cooling of the scalp. In response, a controller may increase inflation pressure of chambers corresponding to arms or lobes having increased temperature by, for example, increasing an output of the pump fluidly coupled to those chambers or otherwise directing additional fluid into those particular chambers.

Enclosure

Generally, the enclosures described here may comprise a surface configured to resist deformation as the inflatable member is moved from the deflated to the inflated configuration. The enclosures described here may provide a counter force to the inflatable member as it is inflated, which, when in use with a heat exchanger, may allow a compressive force to be applied by the heat exchanger to a patient's head. Using the enclosure as a counter force to the inflatable member in the inflated configuration may allow the inflatable member to retain a uniform shape when in the inflated configuration and may increase a contact area between the heat exchanger and a scalp of a patient.

Figure 13:
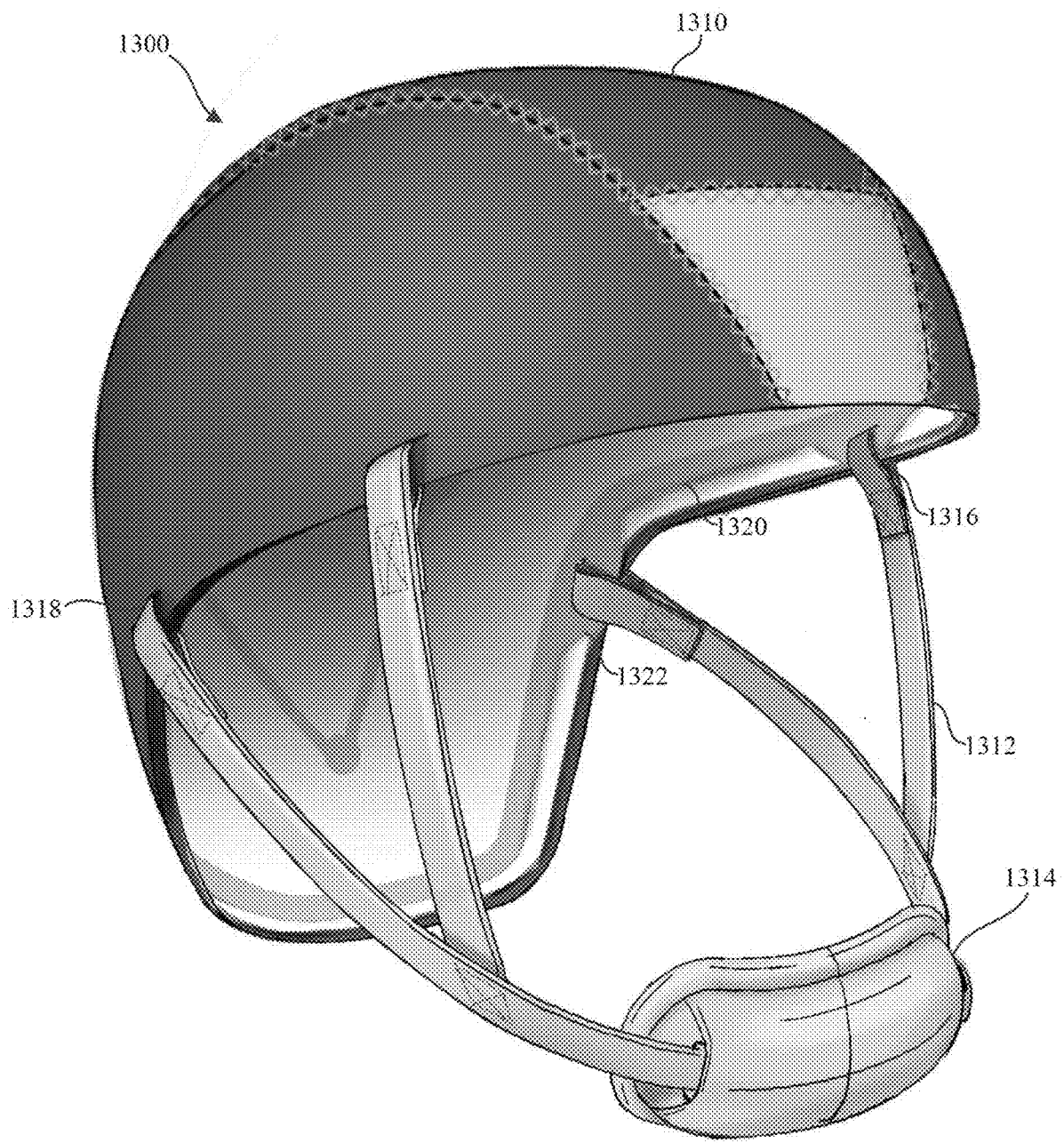
FIG. 13 is a perspective view of an illustrative variation of an enclosure

FIG. 13 is a perspective view of an illustrative variation of an enclosure (1300) comprising a shell (1310), strap (1312), chin strap (1314), strap fastener (1316), shell fastener (1318), inflatable member (1320), and inflatable member fastener (1322). In some variations, the shell (1310) may comprise a hemispherical or dome shape, and may be in the form of a helmet. For example, the shell (1310) may comprise a rigid (e.g., molded plastic) or a semi-rigid material. For example, the shell (1310) may be more rigid than the inflatable member (1320). As shown in FIG. 13, the shell (1310) may be configured to surround at least a portion of, and in some variations, the entire inflatable member (1320). For example, the shell (1310) may define a cavity configured to surround at least a portion of the inflatable member (1320) and/or receive the head of a patient (not shown). In some variations, the shell (1310) may be surrounded by a flexible cover as described herein. The shell (1310) may comprise one or more ports (not shown) configured to permit one or more fluid connectors to connect to one or more of the inflatable member (1320) and a heat exchanger (not shown). The ports may be further configured to permit wired connection to one or more sensors of the cooling cap assembly. In some variations, the shell (1310) may comprise one or more electronic components (e.g., processor, memory, PCB, battery, leads, audio output device, haptic feedback device, visual output device) of the cooling cap assembly. For example, the shell (1310) may comprise an audio output device near an earhole portion of the enclosure (1300) configured to provide audio notification related to a cooling treatment (e.g., operation state) of the cooling cap assembly. As another example, a haptic feedback device may be configured to vibrate during a power state transition of a cooling unit coupled to the cooling cap.

In some variations, the enclosure (1300) may comprise one or more straps (1312) configured to fasten the shell (1310) to a patient. The strap (1312) may comprise a chin strap (1314) configured to wrap underneath a jaw of the patient. In some variations, the chin strap (1314) may be adjustable for comfort and may comprise one or more rigid and soft components. For example, the chin strap (1314) may be threaded through one or more components of the cooling cap assembly. In some variations, the strap (1312) may comprise a strap fastener (1316) (e.g., loop) configured to fasten the strap (1312) to one or more of the shell (1310), inflatable member (1322), cover, and heat exchanger (not shown). In some variations, the shell fastener (1318) and inflatable member fastener (1322) may each comprise a slit configured to allow the strap fastener (1316) to loop therethrough.

Figure 14C:
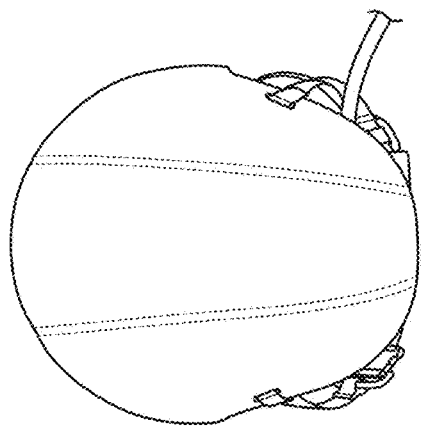
FIGS. 14A-14F are perspective views of an illustrative variation of a cooling cap.
Figure 14F:
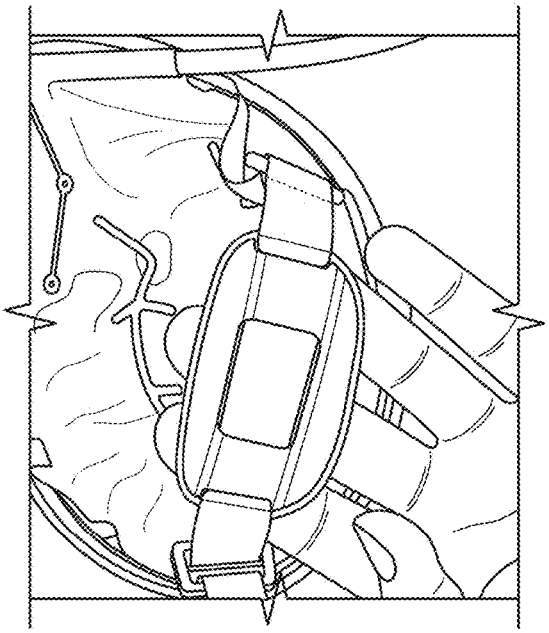
Figure 14B:
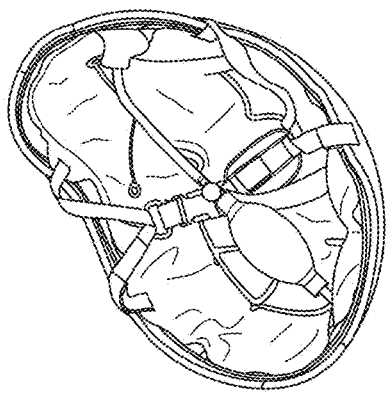
Figure 14E:
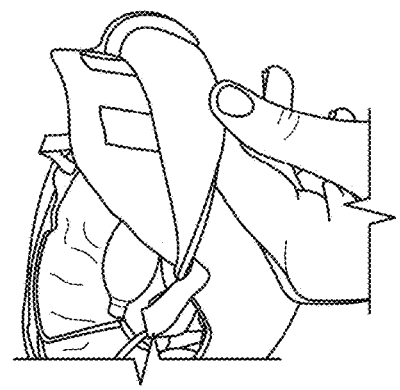
Figure 14A:
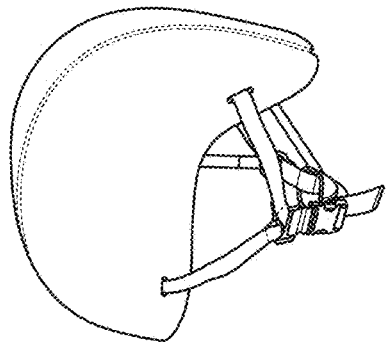
Figure 14D:
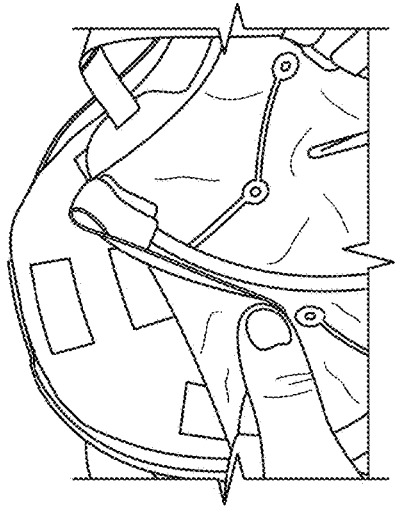
Figure 15C:
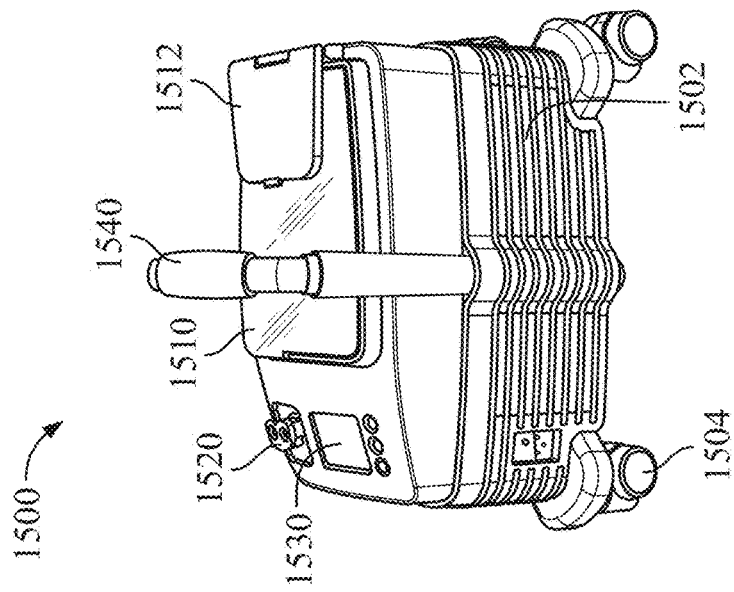
Figure 15B:
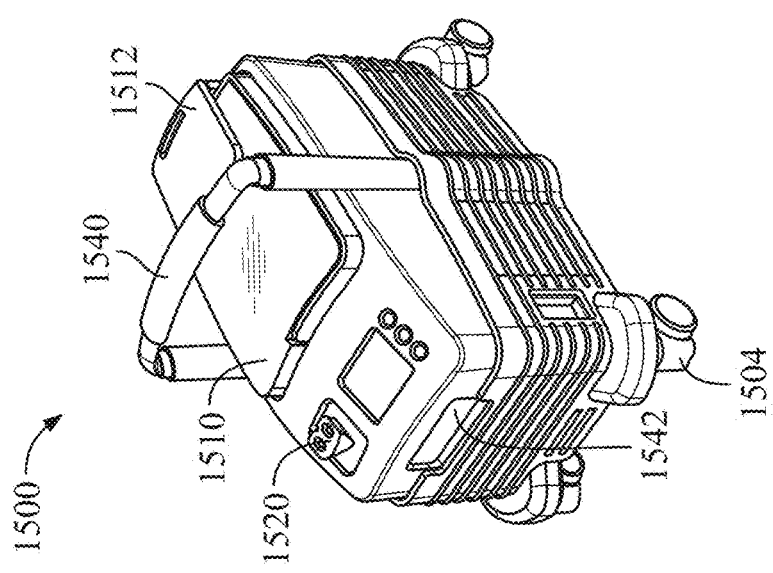
Figure 15A:
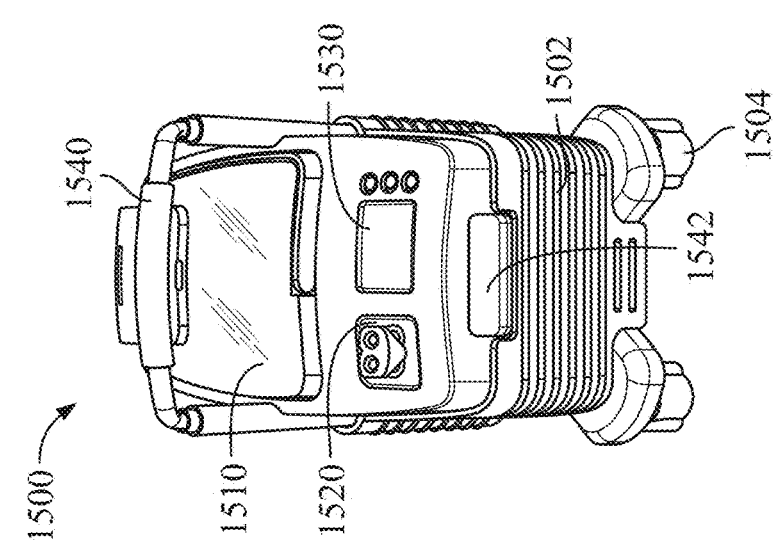
Figure 15H:
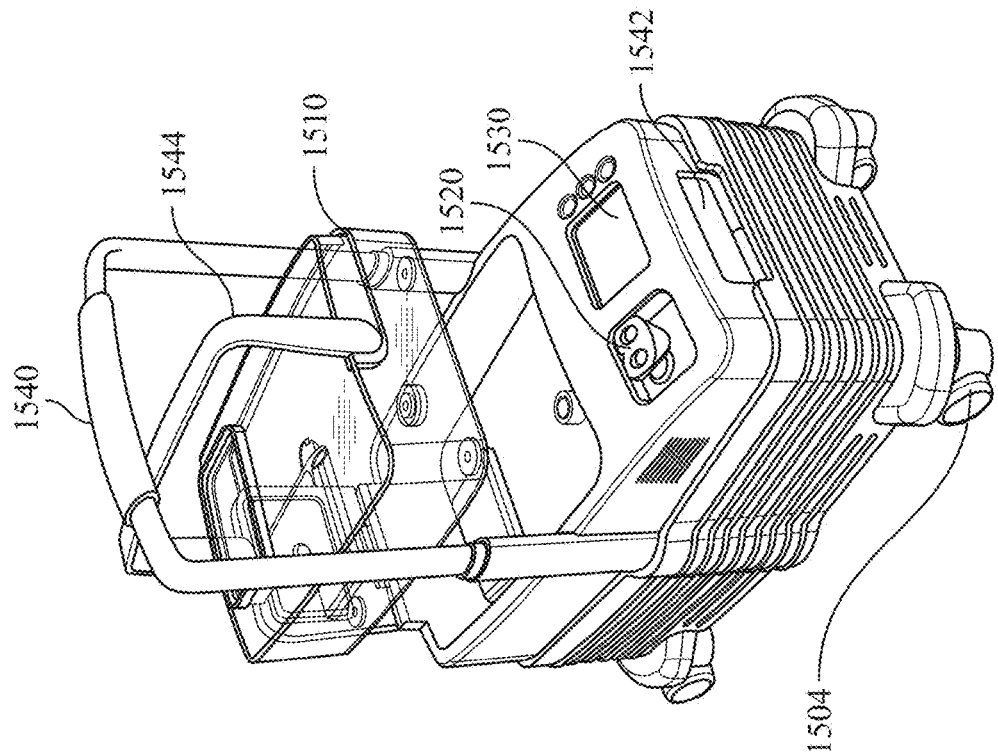
Figure 15G:
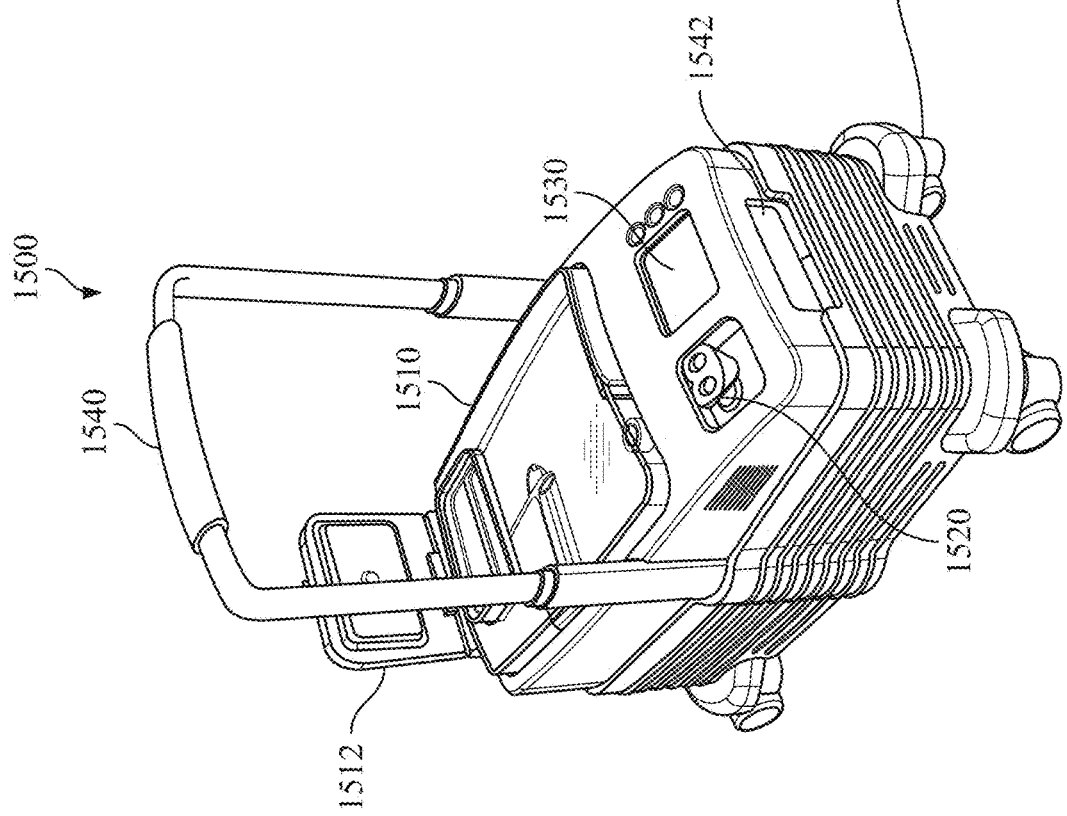
Figure 16A:
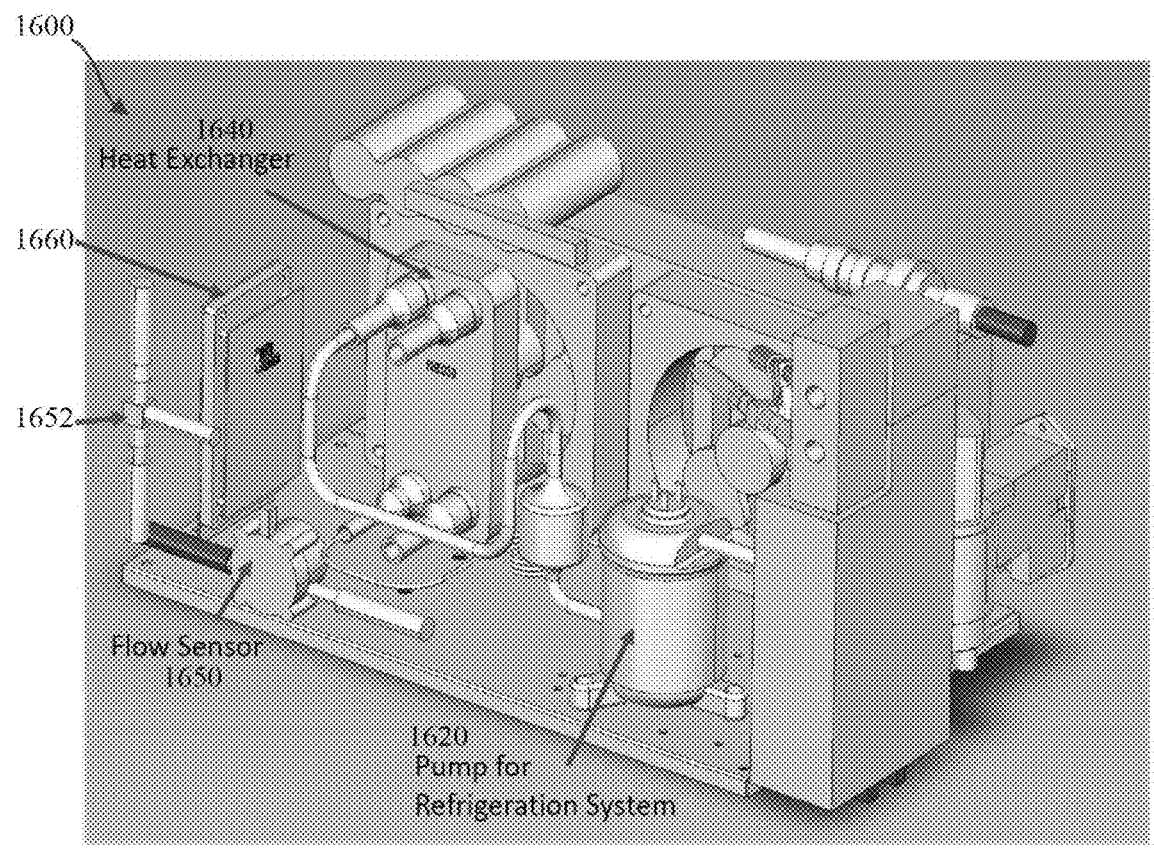
FIGS. 16A-16D are internal views of an illustrative variation of a cooling unit.
Figure 16B:
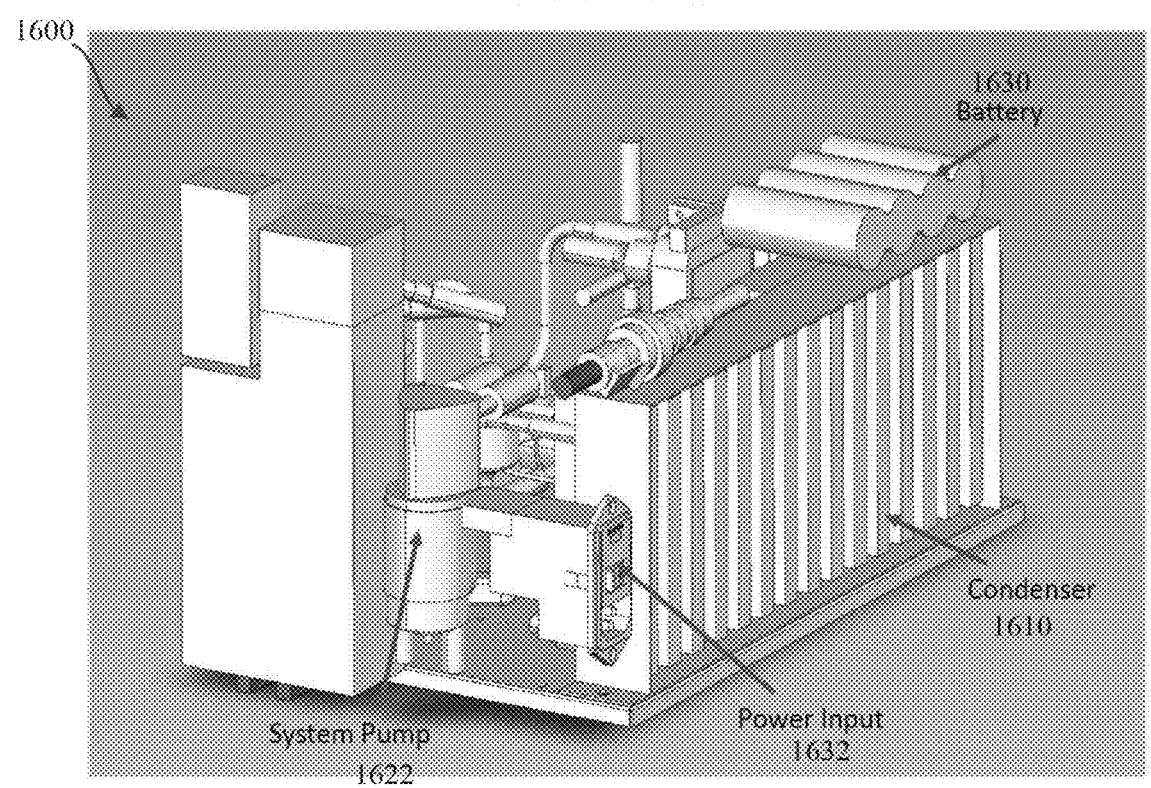
Figure 16C:
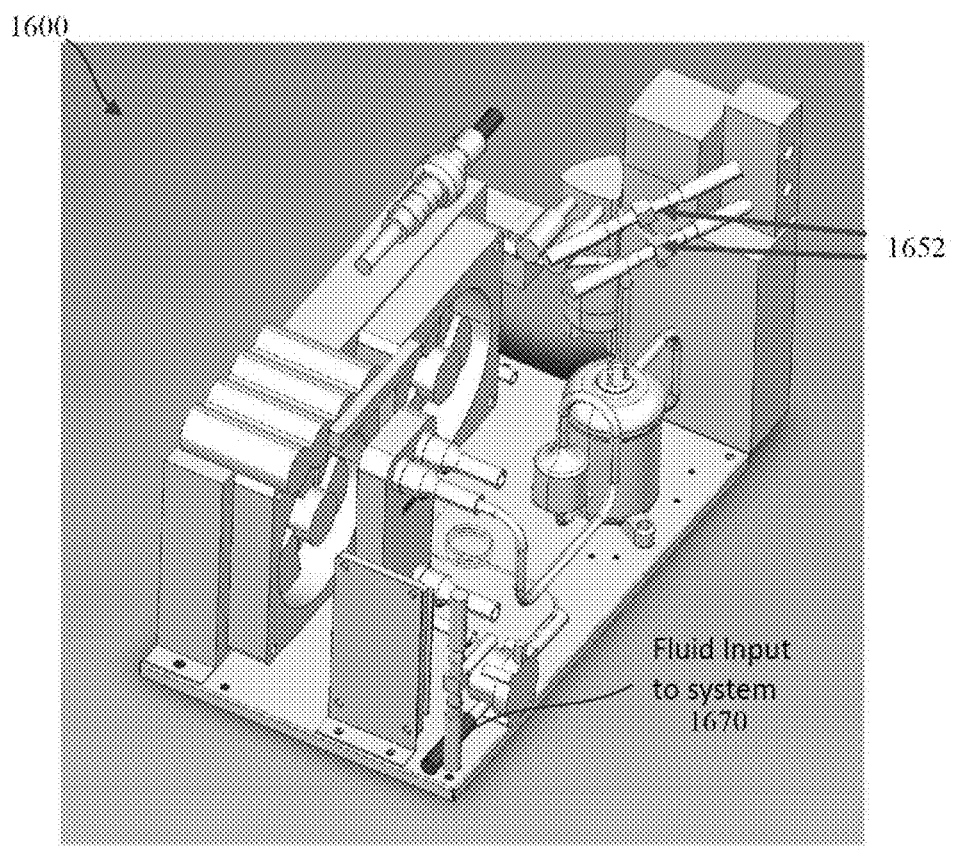
Figure 16D:
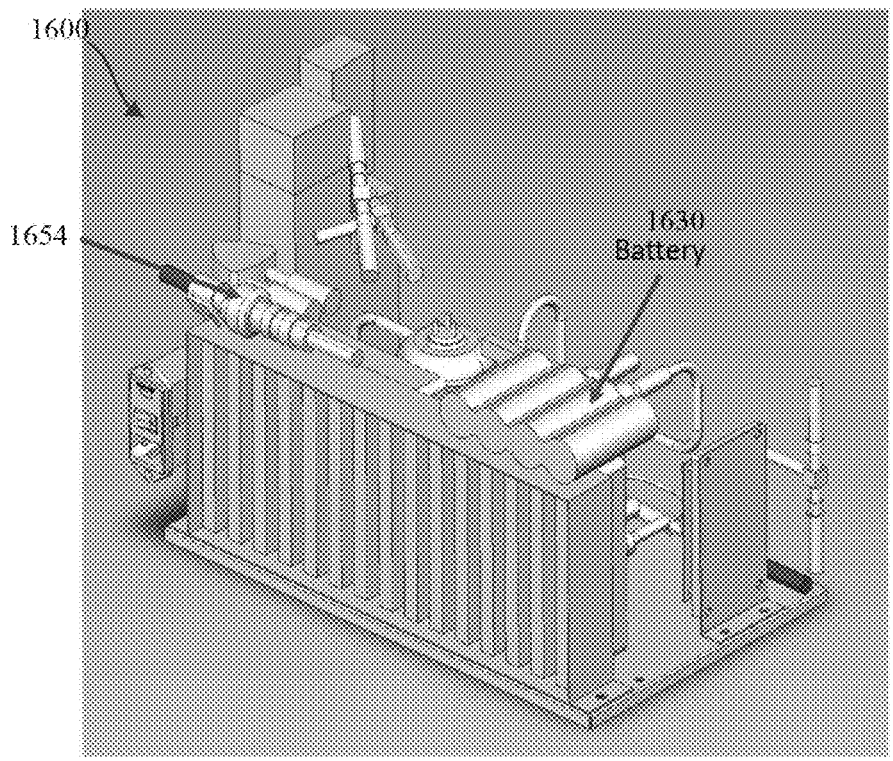

FIGS. 14A-14F are perspective views of an illustrative variation of an enclosure (e.g., cooling cap). FIGS. 14A and 14C are respective side and rear views of the enclosure. FIG. 14B is a bottom view of the enclosure with an inflatable member disposed within the enclosure. A manual pump is coupled to the inflatable member. FIGS. 14D and 14E illustrate that the inflatable member and a flexible cover may be releasably coupled (e.g., via Velcro®) to a more rigid shell of the enclosure. FIG. 14F is a detail view of a chin strap of the enclosure. In some variations, a fastener (e.g., double-sided hook tape) may secure a shell of an enclosure to an inflatable member.

Figure 4A:
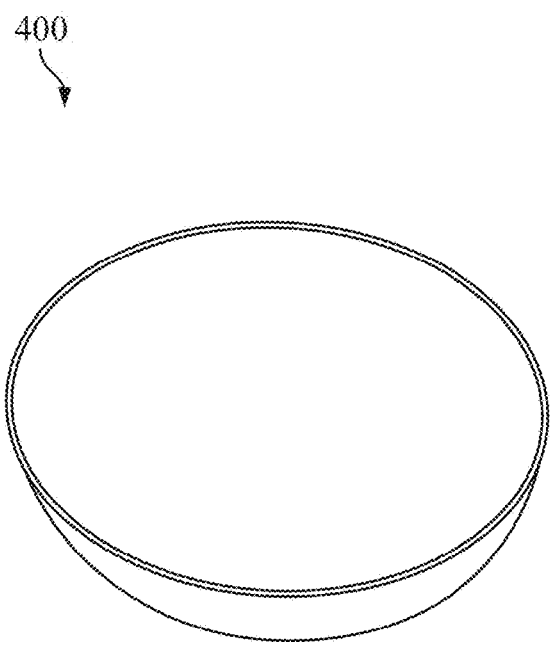
FIGS. 4A and 4B are perspective views of an illustrative variation of an enclosure.
Figure 4B:
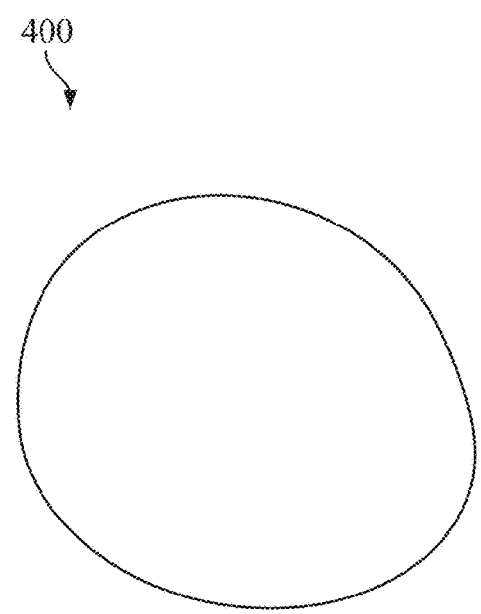

FIGS. 4A and 4B are interior and exterior perspective views of a variation of an enclosure (400). In some variations, the enclosure (400) may comprise a rigid (e.g., molded plastic) or a semi-rigid material. For example, the enclosure (400) may be more rigid than the inflatable member. As shown in FIGS. 4A-4B, the enclosure (400) may be configured to surround at least a portion of the inflatable member. For example, the enclosure (400) may define a cavity configured to surround at least a portion of the inflatable member and/or receive the head of a patient. In some variations, the enclosure may comprise a hemispherical shell (e.g., the enclosure may comprise a dome shape). Although not depicted in FIGS. 4A and 4B, in some variations, the enclosure may comprise a fastener that may reversibly couple the enclosure (and the entire compression assembly) to a patient's head.

Liner

Generally, the liners described here may be configured to contact one or more of the hair and scalp of a patient and to provide a barrier between the heat exchanger and the scalp. In some variations, the liner may be thin flexible, and/or lightweight, and may allow for heat transfer between the heat exchanger and the scalp. For example, the liner may comprise a flexible and/or elastic material such as a knit polyamide or a knit nylon. The liner may form a cavity configured to receive a patient's head, however, unlike the enclosure, the liner may be adaptable and without a particular structure (e.g., floppy and conformable). The liner may be applied over a patient's scalp and may conform thereto. In some variations, a patient's hair may be evenly spread across the scalp prior to application of the liner to the head, which may assist in providing more evenly distributed cooling to the scalp. For example, a patient's hair may be adjusted to cover a patient's part line, which may help protect the patient's part line during cooling. In some variations, the liner may assist in holding the hair in a desired configuration. In some variations, a moisturizing lotion and/or hair conditioner may be applied to the scalp before application of the liner to improve conduction and/or prevent the hair from freezing during treatment. The liner may comprise a washable, reusable material. In some variations, the liner may be elastic. The liner may be disposed between the patient's scalp and a heat exchanger such that the heat exchanger is moveable relative to the liner. In some variations, the liner may form a friction fit with the scalp such that the liner may remain on the scalp when a cooling cap assembly is removed from a patient's head. As mentioned above, in some variations, the cooling cap assembly may not include a liner.

Cover

Generally, when included in the cooling assemblies described herein, the cover may be configured to hold (e.g., fix, anchor) a compression assembly to the patient. For example, a cover may be disposed over an enclosure of the cooling cap assembly and may comprise a fastener that may reversible couple the cooling cap assembly to a patient. In this manner, the cooling cap assembly may be secured to a head of a patient such that the cooling cap assembly applies a predetermined pressure to the heat exchanger and head of the patient. The inflatable member may be inflated to further increase the compression to the head and a contact area between the heat exchanger and the scalp of the patient, as described in more detail above. In some variations, the cover may comprise a flexible, elastic material such as neoprene, which may be configured to expand as necessary and to hold the compression assembly in place on the head. In some variations, the cover may hold the compression assembly and the heat exchanger, such that the compression assembly and the heat exchanger may be removed from the patient's head together. Subsequently, the cooling cap assembly (e.g., the compression assembly and the heat exchanger) may be placed back onto the head of the patient as a single piece during future use.

In some variations, the cover may be fixedly coupled to compression assembly (e.g., to the enclosure), while in other variations, the cover may be releasably coupled to the compression assembly. The cover may assist a patient in placing the cooling cap assembly (e.g., the compression assembly) on the head and may secure the cooling cap assembly to the head during use. In some variations, as will be described in more detail herein, the heat exchanger may be separate from, but may releasably couple, to the compression assembly. In these variations, the cover may also assist in removing, securing, and re-applying the heat exchanger from a patient's head.

Figure 5:
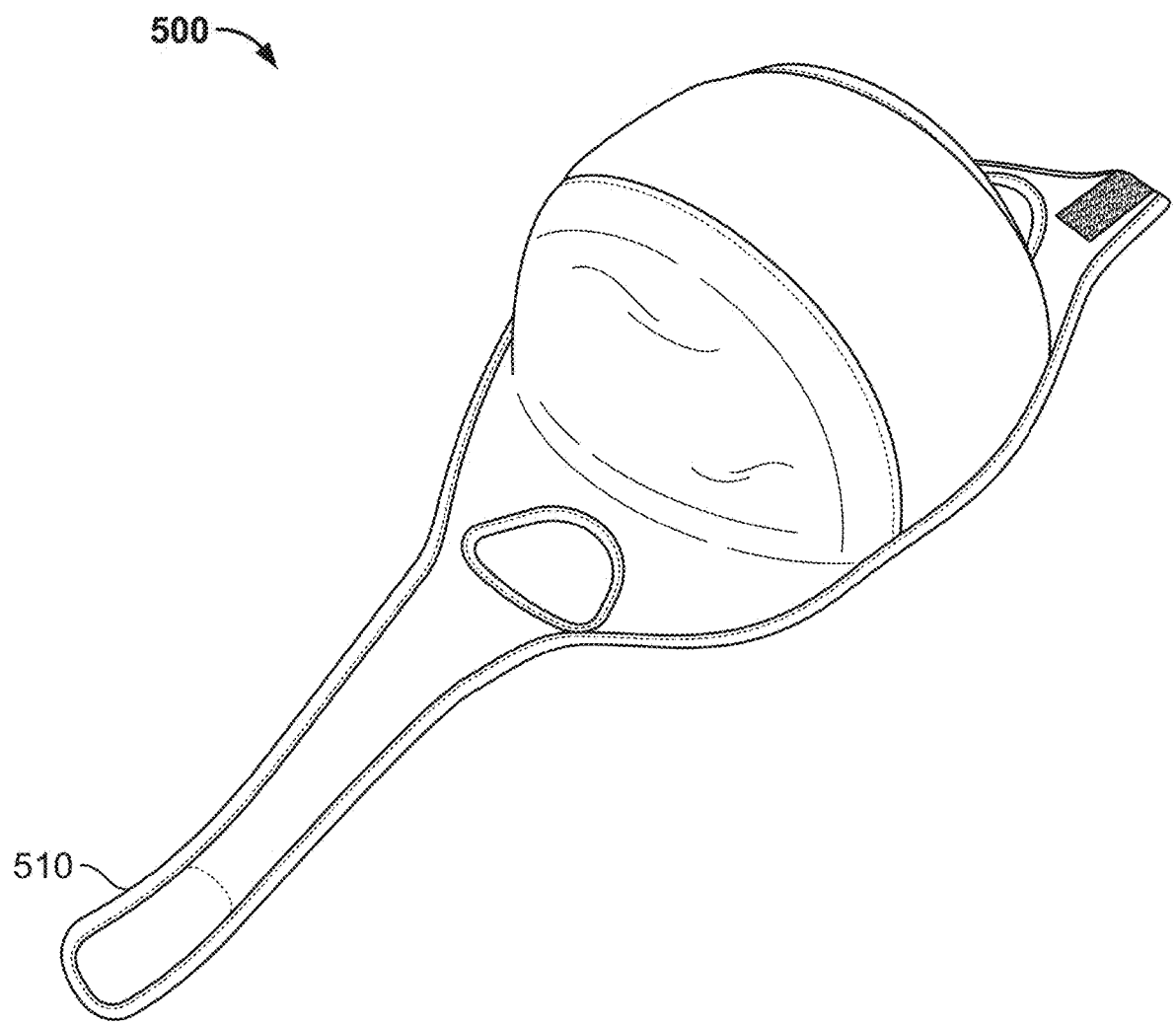
FIG. 5 is a perspective view of an illustrative variation of a flexible cover.

FIG. 5 is a perspective view of an illustrative variation of a flexible cover (500). As shown there, the cover (500) (e.g., distensible cap) may comprise a fastener assembly (e.g., chin strap (510)) configured to wrap underneath a jaw of the patient.

Sensors

Generally, the sensors described here may be configured to measure one or more parameters such as, for example, temperature or force (e.g., pressure), which may be used to control one or more components of a cooling unit and/or a cooling cap assembly. As shown in FIG. 1B, in some variations, the cooling cap assembly may comprise one or more sensors (132). In this variation, the one or more sensors (132) may be coupled to the heat exchanger (120) and may be configured to measure one or more parameters of the cooling cap assembly, such as, for example, a temperature of the fluid circulating in the heat exchanger, a scalp temperature, and/or a force applied to a patient's scalp by the heat exchanger or vice versa. In some variations, the sensors may include one or more temperature sensors (e.g., two, three, four, five, or more) and/or one or more pressure or force sensors (e.g., two, three, four, five, or more).

In some variations, the heat exchanger (120) may comprise at least one sensor (132) in each of the portions of the heat exchanger (120). For example, each arm or lobe of the heat exchanger (120) may comprise one or more sensors (132) (e.g., one temperature sensor, one pressure sensor). In some variations, a temperature sensor may be disposed on an external surface of the heat exchanger (120), within the heat exchanger (120), or within a fluid channel of the heat exchanger (120). For example, a temperature sensor may be disposed on an interior side of the heat exchanger (120) (e.g., facing the scalp) and a pressure sensor may be disposed on an exterior side of the heat exchanger. The sensors may be disposed at a distal end of the arms or lobes. In one instance, the sensors may comprise six temperature sensors coupled to the heat exchanger and an ambient temperature sensor disposed external of the cooling cap assembly. In some variations, the temperature may be a scalp temperature and/or a fluid temperature. In some variations, the one or more sensors (132) may comprise a radial pattern on the heat exchanger.

In some variations, one or more sensors may be coupled to a controller. The controller may be configured to receive and process the sensor measurements (e.g., temperature, force) to control the cooling cap assembly. For example, inflation pressure of an inflatable member may be adjusted by the controller based on temperature measurements.

In some variations, an inflation pressure of each chamber of an inflatable member (130) may be independently adjusted based on a measured temperature of one or more of its respective chamber. In some variations, the measured temperature may be compared to a predetermined threshold or target temperature or a predetermined target temperature range. For example, in some variations, the target temperature range for the temperature of a patient's scalp may be from about 3° C. to about 5° C. or from about 16° C. to about 18° C. If one or more of the scalp temperatures exceeds the predetermined threshold and/or is outside of the predetermined range, the controller may instruct or otherwise transmit signals to one or more valves fluidly coupled to the chambers of the inflatable member (130) and/or a pump fluidly coupled to the inflatable member (130) to increase an inflation pressure in one or more chambers. Selectively increasing the inflation pressure in particular chambers may increase the contact area between the scalp and the heat exchanger in the location(s) corresponding to those particular chambers. In this way, the controller, and one or more valves and/or the pump fluidly coupled to the inflatable member (130) may be configured to dynamically control the inflation pressure.

Cooling Unit

As mentioned above, the cooling systems described herein may comprise a cooling unit. The cooling unit may be configured to decrease a temperature of a cooling fluid and to transfer the cooled cooling fluid to the cooling cap assembly (e.g., the heat exchanger) to reduce a scalp temperature of a patient using the cooling cap assemblies described herein. As shown in FIG. 1A, the cooling unit (150) may comprise a compressor and/or a thermoelectric cooling mechanism (152) (e.g., a vapor compressor comprising a refrigerant), a reservoir (154), a sensor (156), and a pump (158) (e.g., gear pump). The cooling unit (150) may be fluidly coupled to the heat exchanger (120) of the cooling cap assembly (110) and may be configured to circulate a cooling fluid through the heat exchanger (120). In some variations, the fluid may comprise water and alcohol or liquid water, ice, and salt. For example, the fluid may comprise a mixture of isopropyl alcohol and water. In some variations, the ratio of alcohol to water may be from about 5% to about 50%, from about 5% to about 30%, from about 20% to about 30%, and from about 5% to about 25%, including all sub-values and ranges in-between. In some variations, a composition and ratio of the fluid may be determined based on a size of the reservoir and/or volume of fluid.

In some variations, the cooling unit (150) may be compact such that the cooling unit (150) may be portable and enable freedom of movement for the patient. Additionally, in some variations, the cooling unit (150) may comprise a portable power source (e.g., a battery), which may allow a patient to use the cooling system without access to an electrical outlet. As will be apparent from the description below, the cooling unit (150) enables the cooling systems described herein to be used without dry ice, thereby increasing safety and reducing operational complexity.

As mentioned above, the cooling unit (150) may be fluidly coupled to the cooling cap assembly (110). For example, the cooling unit may comprise a fluid conduit (not shown) releasably coupled to the heat exchanger (120). For example, the fluid conduit (e.g., tubing assembly, tube) may comprise a set of flexible, polymeric tubes of a predetermined length, such as, for example, between about 1 foot and about 15 feet. In some instances, the cooling unit (150) and/or the fluid conduit may comprise one or more valves that may assist in controlling the flow of the circulating cooling fluid. In some variations, the fluid connector may comprise one or more of polyvinyl chloride (PVC) and thermoplastic polyurethane (TPU). In some variations, the fluid connector may be covered by an outer sheath, which may comprise an insulating fabric (e.g., neoprene) that may be elastic and/or laminated.

Figure 1C:
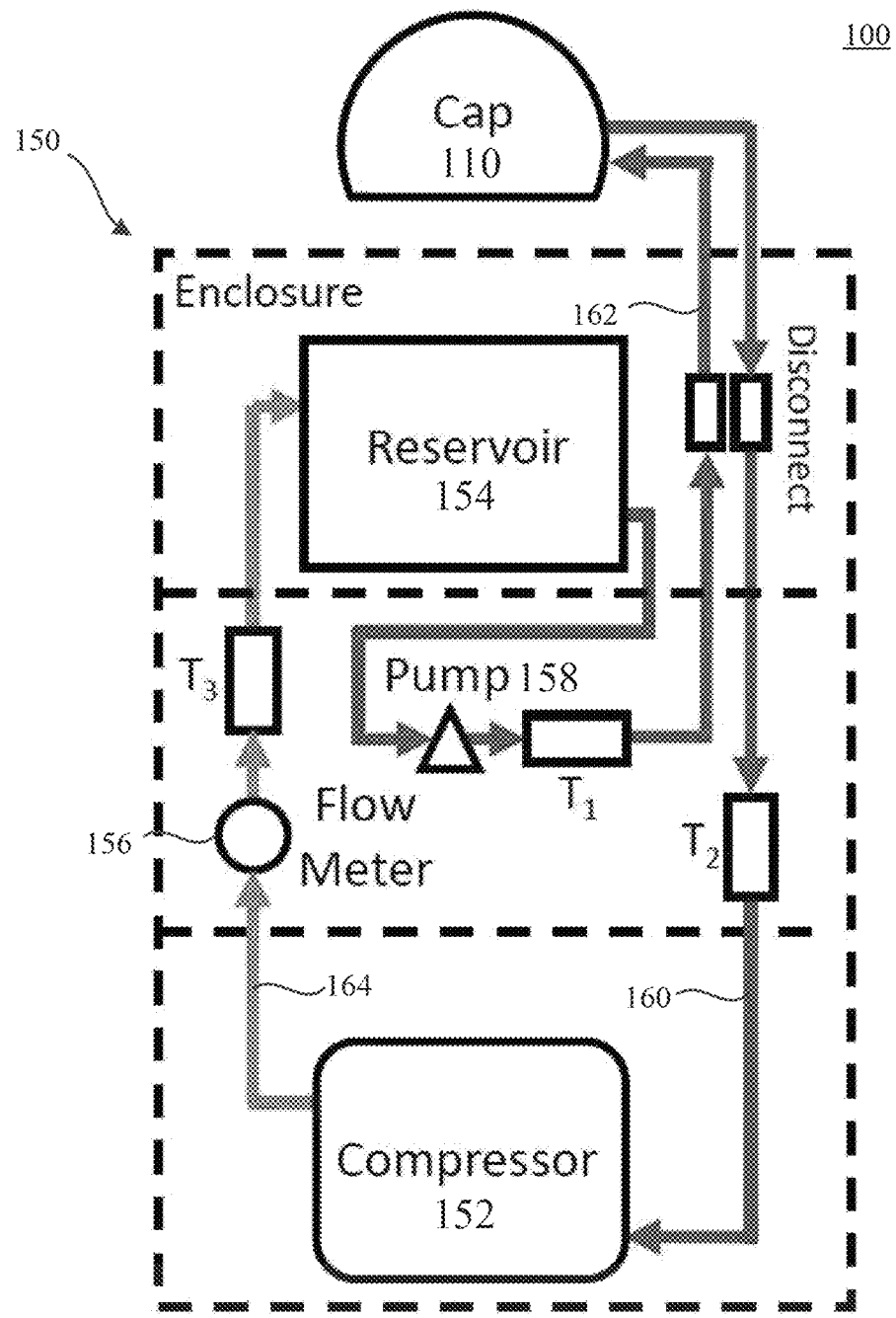

FIG. 1C is a block diagram of a variation of a cooling system (100) comprising a cooling cap assembly (110) and a cooling unit (150). A fluid (162) (e.g., water, water and alcohol) at a first temperature $T_1$ may be output from the cooling unit (150) to the cooling cap assembly (110). A fluid (160) at a second temperature $T_2$ may be received by the cooling unit (150) from the cooling cap assembly (110). A compressor (152) may be configured to reduce a temperature of circulating fluid returned from the heat exchanger (120). In some variations, the compressor (152) may be configured to compress a refrigerant used to cool fluid passing through an expansion chamber. For example, the fluid (160) may be input into the compressor (152), and the compressor (152) may be configured to output a fluid (164) at a temperature $T_3$, which may be lower than the temperature $T_2$. The reservoir (154) may be configured to hold cooled fluid received from the compressor (152). For example, the reservoir (154) may comprise a container in which the fluid (164) may be stored, and in some variations, the reservoir (154) may comprise ice. A flow meter (152) may be disposed in a fluid path between the compressor (152) and the reservoir (154), and may be configured to measure a flow of the fluid in the cooling unit (150). A pump (158) may be configured to circulate the fluid to and from the cooling cap assembly (110). For example, an output of the reservoir (154) may be fluidly coupled to the pump (158) configured to pump the fluid (162) at a temperature $T_3$ into the cooling cap assembly (110).

The sensor (156) may be configured to measure one or more system parameters such as duration of use, fluid flow, and/or temperature. For example, in some variations, the sensor (156) may comprise one or more temperature sensors, which may be coupled to a fluid flow path between a cooling cap assembly (110) and the compressor (152) (e.g., on an inlet of the cooling unit (150), between the compressor (152) and the reservoir (154), within the reservoir (154), between the reservoir (154) and the pump (158), on the outlet side of the pump (158), and/or between the outlet of the cooling unit (150) and the cooling cap assembly (110)). The one or more temperature sensors may be configured to measure the temperature of fluid flowing to, through, or out of the cooling unit (150), for example, temperatures $T_1$, $T_2$, and $T_3$. In some variations, the temperature sensors may be thermistors or thermocouples housed in liquid-impermeable fittings. Additionally or alternatively, the sensor (156) may comprise a fluid flow sensor, which may be coupled to the fluid flow path between the cooling cap assembly (110) and the compressor (152) (e.g., on an inlet of the cooling unit (150), between the compressor (152) and the reservoir (154), within the reservoir (154), between the reservoir (154) and the pump (158), on the outlet side of the pump (158), and/or between the outlet of the cooling unit (150) and the cooling cap assembly (110)). The fluid flow sensor may be configured to measure the flow rate of fluid flowing to, through, or out of the cooling unit (150). Additionally or alternatively, the sensor (156) may comprise or otherwise be communicatively coupled to a timer configured to count or otherwise determine a duration of, for example, a cooling treatment session, based at least in part on one or more of fluid flow, temperature, and power usage measurements.

In some variations, the cooling unit (150) may comprise a controller as described herein to control the flow rate and/or the temperature of the circulating fluid based on, for example, sensor (156) measurements, sensors in the cooling cap assembly, and/or user input. For example, the controller may receive sensor data and alter the output of a cooling unit component, e.g., the pump (158) and/or the compressor (152), based on the sensor data. As mentioned above, in some variations, the sensor (156) of the cooling unit (150) may comprise a fluid flow sensor (e.g., a hall-effect sensor) configured to measure a flow rate of fluid circulating through the cooling unit (150) and cooling cap assembly and/or a temperature sensor (e.g., thermistor, thermocouple) configured to measure the temperature of the circulating fluid at various locations in the cooling system. In particular, in some instances, the controller may be configured to receive a plurality of temperature measurements from the temperature sensors (in the cooling unit and/or the cooling cap assembly) and to calculate a temperature difference (i.e., delta T) between two or more of the temperature measurements (e.g., between a first temperature and a second temperature measured at different locations in the cooling unit (150) and/or the cooling cap assembly (110)). The controller may also be configured to receive fluid flow rate measurements from the fluid flow sensor. The controller may be configured to compare the temperature measurements, the calculated delta T, and/or the flow rate measurements to target measurements (e.g., target temperature, target delta T, target flow rate) and/or a target range of measurements, and may adjust one or more components of the cooling unit (150) to achieve a desired result (e.g., a lower cooling fluid temperature, a higher cooling fluid temperature, a lower scalp temperature (as measured by sensors in the cooling cap assembly), a higher scalp temperature, a lower flow rate, a higher flow rate). For example, the controller may adjust the power delivered to the compressor (152) and/or the pump (158) to alter (e.g., increase or decrease) or maintain the measured temperatures, measured flow rate, and/or delta T. Adjusting the power to the compressor (152) may increase or decrease the temperature of the cooling fluid exiting the compressor (152) while adjusting the power to the pump (158) may increase or decrease the flow rate of the cooling fluid in the system. A higher flow rate may be generally correlated to a lower delta T (as the fluid is exchanged faster and there is less time for heat exchange between the cooling fluid and the scalp). In some variations, the target temperature range for the cooling fluid at the site of cooling (e.g., in the heat exchanger) may be from about 2° C. to about 4° C. and/or the target temperature range for the cooling fluid in the cooling unit may be from about −2° C. to about 2° C. or between about 0° C. to about 2° C. In some variations, the controller may comprise a timer, and the controller may be configured to determine the duration of, for example, a cooling treatment session.

In some variations, the controller may display a graphical user interface to enable user adjustment of the flow rate and/or temperature of the circulating fluid. In some variations, the controller may provide a user with instructions, via the graphical user interface, to add or remove ice from the reservoir and/or to modify the cooling fluid (e.g., modify the ratio of water to alcohol) to alter the temperature of the cooling fluid. In some variations, the controller may adjust the power to the compressor (152) and/or pump (158) in response to user input received via, e.g., the graphical user interface. While described above in relation to the cooling unit (150), it should be appreciated that the controller may be separate from the cooling unit (150), for example, in variations in which the controller is a computing device (e.g., a smartphone, tablet, or the like).

In some variations, the cooling cap assembly (110) and cooling unit (150) may be self-contained, portable, reusable, and configured to be self-operated by a patient (e.g., without assistance from a technician). As mentioned above, in some variations, the cooling unit (150) may comprise a battery that enables portability and freedom of movement for the patient.

FIGS. 15A-15K are external views of an illustrative variation of a cooling unit (1500). In some variations, the cooling unit (1500) may be self-contained, portable, reusable, and configured to be self-operated by a patient (e.g., without assistance from a technician). As mentioned above, in some variations, the cooling unit (1500) may comprise a battery (not shown) that enables portability and freedom of movement for the patient. The cooling unit (1500) may comprise a housing (1502), wheels (1504), fluid reservoir (1510), latch (1512), fluid connector port (1520), user interface (1530), and handles (1540, 1542, 1544). The housing (1502) may enclose and protect the internal components of the cooling unit (1500) as described herein and, for example, with respect to FIGS. 16A-16D. The handles (1540, 1542, 1544) and wheels (1504) of the cooling unit (1500) may enable portability of the cooling unit (1500) as they allow a patient to easily move the cooling unit (1500) from one location (e.g., clinic, office, room) to another (e.g., transportation, home, another room) while performing a continuous cooling treatment. In some variations, the cooling unit (1500) may comprise a height adjustable handle (1540) and side handles (1542). The wheels (1504) may be configured to allow the cooling unit (1500) to roll in any direction. In some variations, the cooling unit (1500) may be configured to fit on a floor of a car seat (e.g., behind a driver or front passenger seat) or on a car seat itself. For example, the cooling unit (1500) may have a width from about 200 mm to about 500 mm, a length from about 400 mm to about 600 mm, and a height from about 350 mm to about 500 mm.

In some variations, the cooling unit (1500) may comprise a fluid reservoir (1510) releasably coupled to the housing (1502). In some variations, the fluid reservoir may be configured to hold from about 0.5 L to about 4 L of fluid. For example, the fluid reservoir (1510) may be configured to hold about 3 L of fluid. In some embodiments, the fluid reservoir (1510) may have a width from about 100 mm to about 300 mm, a length from about 200 mm to about 300 mm, and a height from about 50 mm to about 150 mm. In some embodiments, the fluid reservoir may comprise a handle (1544) configured to enable a user to separate the fluid reservoir (1510) from the housing (1502) of the cooling unit (1500). In some variations, the cooling unit (1500) may comprise a latch (1512) configured to releasably engage the fluid reservoir (1510) to the housing (1502). As shown, for example, in FIGS. 15B-15G, the latch (1512) may comprise a hinge configured to transition between an engaged and disengaged configuration. The latch (1512) may overlie the fluid reservoir (1510) in the engaged configuration to form a fluid seal over an opening of the fluid reservoir (1510). In some variations, the latch (1512) may further comprise an attachment sensor configured to generate an attachment signal when the fluid reservoir (1510) is engaged to the latch (1512). A controller of the cooling unit (1500) may be configured to prevent operation if the attachment signal is not received.

In some variations, the cooling unit (1500) may comprise a fluid connector port (1520). In some variations, the fluid connector port (1520) may comprise a fluid inlet and a fluid outlet configured to fluidly couple the cooling unit (1500) to a heat exchanger (not shown) of a cooling cap. In some variations, fluid connector port (1520) may be located on an external surface of the housing (1502) to allow easy access and visualization confirmation of fluid connection/disconnection by the patient. In some variations, the cooling unit (1500) may comprise a user interface (1530) configured to display cooling information and/or allow control of the cooling unit (1500).

FIGS. 15L-15N are exploded perspective views of an illustrative variation of a cooling unit (1500). In particular, FIG. 15N depicts the battery (1550), condenser (1560), system pump (1570), cooling pump (1580), and temperature sensor (1590).

FIGS. 16A-16D are internal views of an illustrative variation of a cooling unit (1600). In some variations, the cooling unit (1600) may comprise a condenser (1610), cooling pump (1620), system pump (1622), battery (1630), power input (1632), heat exchanger (1640), sensors (1650, 1652, 1654), controller (1660) (e.g., circuit board, processor, memory), and fluid input (1670). The condenser (1610) may be configured to condense pressurized gas into a liquid vapor. The pump (1620, 1622) may comprise a cooling pump (1620) (e.g., compressor) configured to reduce a temperature of circulating fluid and a system pump (1622) configured to circulate the fluid to and from a cooling cap assembly (not shown). In some variations, the cooling pump (1620) may be configured to compress a refrigerant used to cool fluid passing through an expansion chamber. The fluid input (1670) may be configured to receive fluid from one or more of a fluid reservoir and cooling cap assembly (not shown).

The sensors (1650, 1652, 1654) may be configured to measure one or more system parameters such as duration of use, fluid flow, temperature, and/or pressure. For example, in some variations, the sensors may comprise a fluid flow rate sensor (e.g., a flow meter) (1650), a temperature sensor (1652), and/or a pressure sensor (1654). In some variations, the system may comprise a plurality of one or more of the above-mentioned sensors. In variations comprising one or more flow rate sensors (1650), the flow meter (1650) may be configured to measure a flow of the fluid in the cooling unit (1600). In variations comprising one or more temperature sensors, the temperature sensors (1652) may be configured to measure the temperature of fluid flowing to, through, or out of the cooling unit (1600). In some variations, the temperature sensors may be thermistors or thermocouples housed in liquid-impermeable fittings. In variations comprising one or more pressure sensors, the pressure sensors (1654) may be configured to measure a pressure of the fluid flowing to, through, or out of the cooling unit (1600).

In some variations, the cooling unit (1600) may comprise a controller (1660) as described herein to control the flow rate, pressure, and/or the temperature of the circulating fluid based on, for example, cooling unit sensor measurements, sensors in the cooling cap assembly, and/or user input. For example, the controller (1660) may receive sensor data and alter the output of a cooling unit component, e.g., the pump (1620, 1622) based on the sensor data. In particular, in some instances, the controller (1660) may be configured to receive a plurality of temperature measurements from the temperature sensors (in the cooling unit and/or the cooling cap assembly) and to calculate a temperature difference (i.e., delta T) between two or more of the temperature measurements (e.g., between a first temperature and a second temperature measured at different locations in the cooling unit (150) and/or the cooling cap assembly (110)). The controller (1660) may also be configured to receive fluid flow rate measurements from the fluid flow rate sensor. The controller may be configured to compare the temperature measurements and/or the flow rate measurements to a target and/or target range of measurements, and may adjust one or more components of the cooling unit (1600) to achieve a desired result (e.g., a lower cooling fluid temperature, a higher cooling fluid temperature, a lower scalp temperature (as measured by sensors in the cooling cap assembly), a higher scalp temperature, a lower flow rate, a higher flow rate). In some variations, the controller (1660) may comprise a timer configured to count or otherwise determine a duration of, for example, a cooling treatment session, based at least in part on one or more of fluid flow, pressure, temperature, and power usage measurements.

In some variations, the controller (1660) may control a user interface to enable user adjustment of the flow rate and/or temperature of the circulating fluid. In some variations, the controller (1660) may provide a user with instructions, via the graphical user interface to, for example, add or remove ice from the fluid reservoir and/or to modify the cooling fluid (e.g., modify the ratio of water to alcohol) to alter the temperature of the cooling fluid. In some variations, the controller may adjust the power to the condenser (1610) and/or pump (1620, 1622) in response to user input received via, e.g., the user interface. While described above in relation to the cooling unit (1600), it should be appreciated that the controller may be separate from the cooling unit (1600), for example, in variations in which the controller is a computing device (e.g., a smartphone, tablet, or the like).

Figure 6:
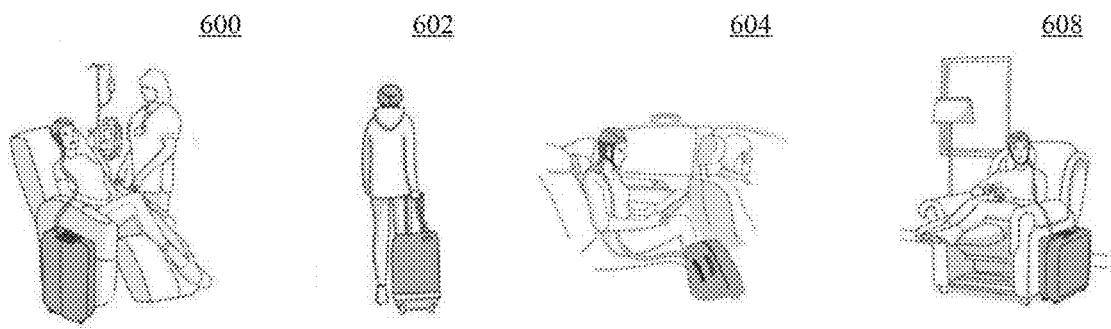
FIG. 6 is a schematic depiction of an illustrative variation of a portable cooling process.
Figure 8A:
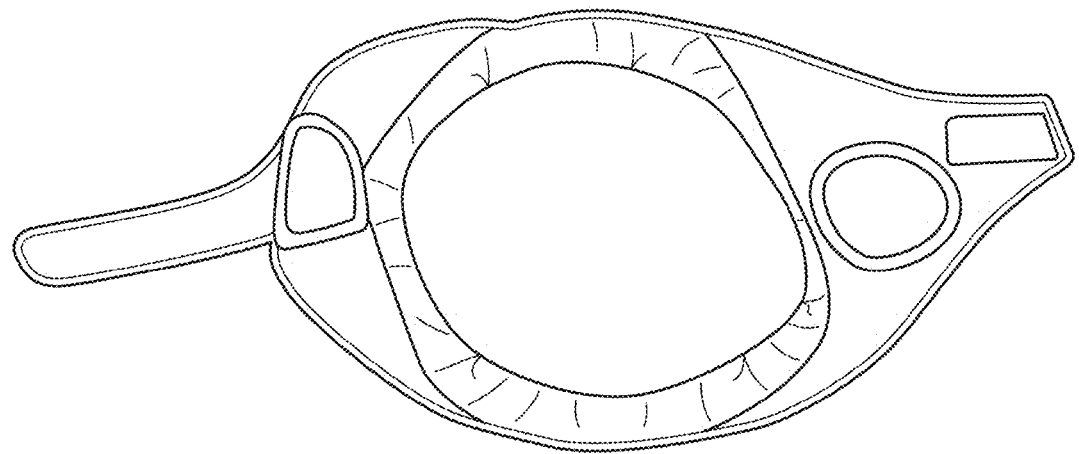
FIGS. 8A-8E are perspective views of an illustrative variation of a cooling cap assembly process.
Figure 8B:
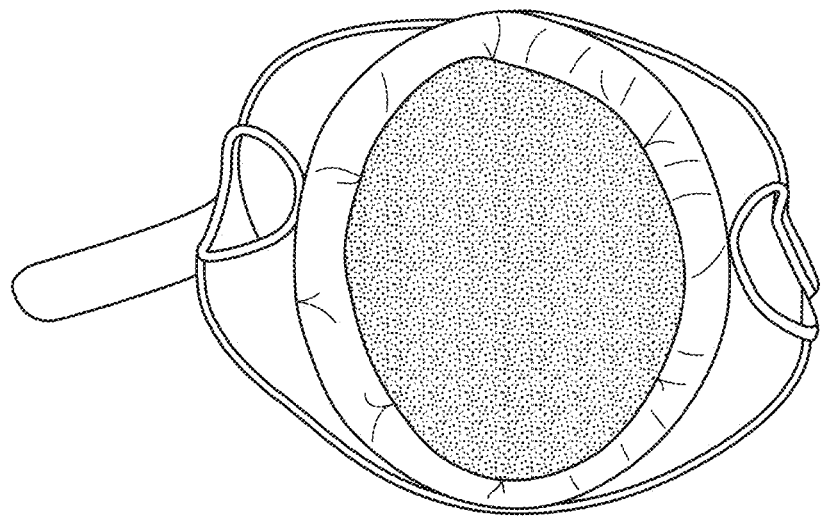
Figure 8C:
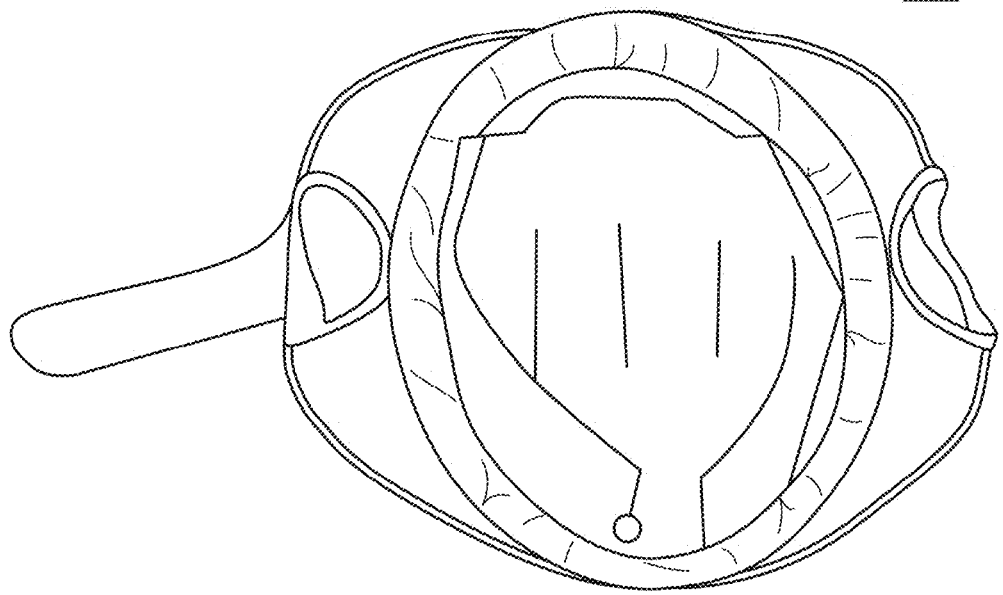
Figure 8D:
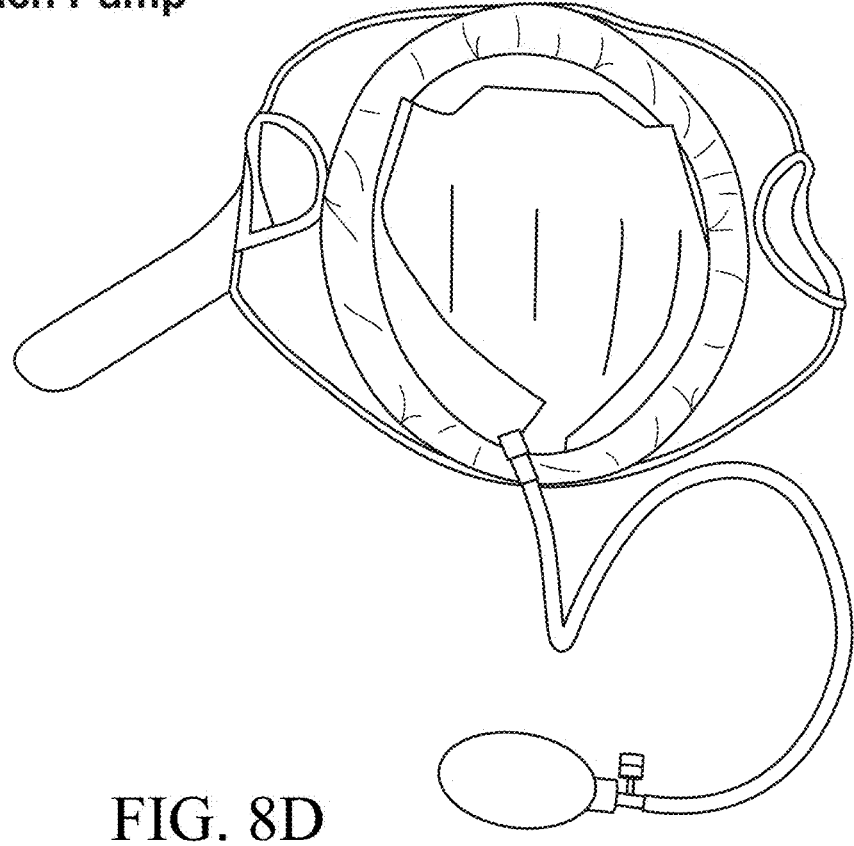
Figure 8E:
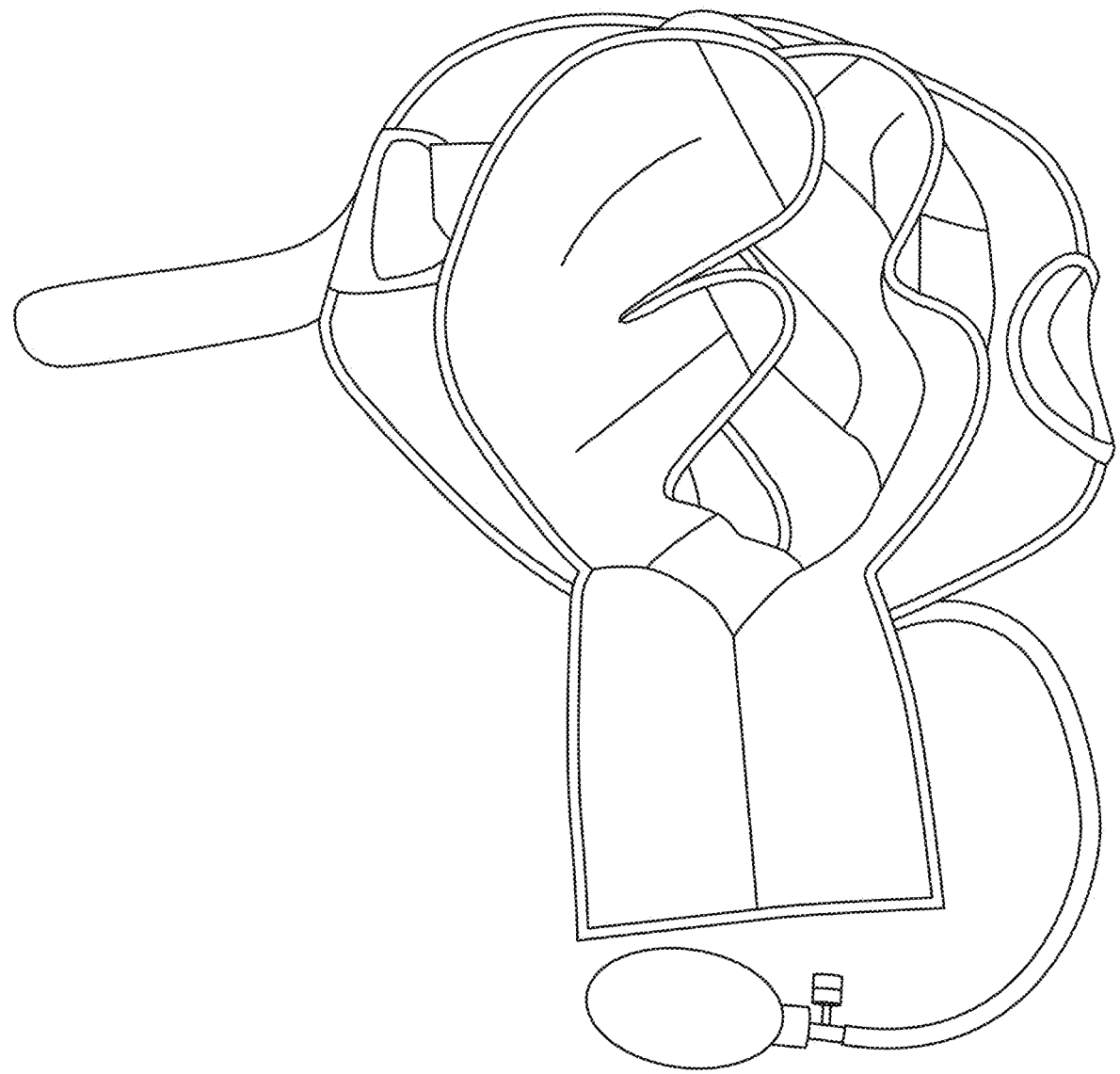

FIG. 6 is a schematic depiction of the cooling system in use. As shown there, a patient may use the portable cooling system in conjunction with a chemotherapy treatment session (600). For example, a patient may apply the cooling cap assembly to the patient's head and may couple the cooling cap assembly to the cooling unit without the assistance of a medical professional (e.g., by themselves). In some embodiments, a patient may begin a cooling treatment prior to receiving a chemotherapy infusion and continue the cooling treatment while receiving a chemotherapy infusion. The cooling unit may be configured to be portable in a manner that allows the patient to perform basic activities (e.g., movement, continence) while receiving cooling treatment. The patient may continue to use the cooling system when the chemotherapy session is completed (602) by transporting the cooling system to the patient's home or other destination. Therefore, the patient need not remain at a treatment center to complete the cooling treatment session. The cooling unit may comprise sufficient portability (e.g., having a suitable size and weight) for a patient to use while traveling (604), for example, between the patient's home and a chemotherapy treatment center. The patient may continue many of their daily activities without interruption outside a chemotherapy treatment center (e.g., at a home) while the cooling treatment is being performed (608). In some variations, a patient may control the cooling system using a graphical user interface on a computing device (e.g., a mobile phone, tablet, laptop, etc.).

Additionally or alternatively, the cooling unit may be located within a medical cart, a bag, a portable case, or the like, which may comprise a handle such that it is easy for the patient to transport.

Controller

As mentioned above, one or more of the cooling cap assembly and the cooling unit may comprise a controller. Additionally or alternatively, the system may further comprise a separate controller (e.g. a computing device) that may be used in conjunction with the cooling cap assembly and/or the cooling unit. Generally, the controller described here may comprise a processor (e.g., CPU) and memory (which can include one or more non-transitory computer-readable storage mediums). The processor may incorporate data received from memory and over a communication channel to control one or more components of the system (e.g., the cooling cap assembly (110), the cooling unit (150, 1600)). For example, in some embodiments, the processor may be configured to control the fluid pump coupled to the inflatable member, the fluid pump (158, 1620, 1622) of the cooling unit (150, 1600), and/or the compressor (152) of the cooling unit (150, 1600). The memory may further store instructions to cause the processor to execute modules, processes and/or functions associated with the methods described herein. In some variations, the memory and processor may be implemented on a single chip. In other variations, they can be implemented on separate chips.

A controller may be configured to receive and process sensor data from the cooling system and other data (e.g., patient data, therapy data) from other sources (e.g., computing device, database, user input). The controller may be configured to control one or more of inflation pressure of the inflatable member, circulating fluid temperature, and flow rate based on the measured sensor data and/or other data (e.g., patient data, therapy data, user input). The controller may be configured to receive, process, compile, store, and access data. In some variations, the controller may be configured to access and/or receive data from different sources. The controller may be configured to receive data directly input and/or measured from a patient. Additionally or alternatively, the controller may be configured to receive data from separate devices (e.g., a smartphone, tablet, computer) and/or from a storage medium (e.g., flash drive, memory card). The controller may receive the data through a network connection, as discussed in more detail herein, or through a physical connection with the device or storage medium (e.g. through Universal Serial Bus (USB) or any other type of port). In variations in which the controller is part of a computing device, the computing device may include any of a variety of devices, such as a cellular telephone (e.g., smartphone), tablet computer, laptop computer, desktop computer, portable media player, wearable digital device (e.g., digital glasses, wristband, wristwatch, brooch, armbands, virtual reality/augmented reality headset), television, set top box (e.g., cable box, video player, video streaming device), gaming system, or the like.

The controller may be configured to receive various types of data. For example, the controller may be configured to receive a patient's personal data (e.g., gender, weight, birthday, age, height, diagnosis, etc.), general health information, or any other relevant information. In some variations, the controller may be configured to create, receive, and/or store patient profiles. The patient profiles may contain patient preferences and/or historical data on treatment sessions (e.g., treatment session characteristics such as, for example, duration, location, time of day, and day of week or cooling parameters such as, for example, inflation pressures, cooling fluid temperatures, scalp temperatures, and cooling fluid flow rate, from prior treatment sessions). A patient profile may additionally or alternatively contain any of the patient specific information previously described. While the above mentioned information may be received by the controller, in some variations, the controller may be configured to process any of the above data from information it has received using software stored on the device itself, or externally. Moreover, in some variations, the controller may be configured to adjust the inflation pressure of the inflatable member, the temperature of the cooling fluid, the flow rate of the cooling fluid, treatment session duration, or other treatment session characteristics or cooling parameters based on a combination of a patient's personal data, general health information, and/or patient profile in addition to the measurements received from the sensors described herein.

The processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), and/or the like. The processor may be configured to run and/or execute application processes and/or other modules, processes and/or functions associated with the system and/or a network associated therewith. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some variations, the memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, and the like. The memory may store instructions to cause the processor to execute modules, processes, and/or functions associated with the communication device cooling unit control, inflation control, and/or communication. Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some variations, the controller may further comprise a communication device configured to permit a patient and/or health care professional to control one or more components of the cooling unit and/or cooling cap assembly. The communication device may comprise a network interface configured to connect the controller to another system (e.g., Internet, remote server, database) by wired or wireless connection. In some variations, the controller may be in communication with other devices via one or more wired and/or wireless networks. In some variations, the network interface may comprise a radiofrequency receiver, transmitter, and/or optical (e.g., infrared) receiver and transmitter configured to communicate with one or more devices and/or networks. The network interface may communicate by wires and/or wirelessly.

The network interface may comprise RF circuitry configured to receive and send RF signals. The RF circuitry may convert electrical signals to/from electromagnetic signals and communicate with communications networks and other communications devices via the electromagnetic signals. The RF circuitry may comprise well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

Wireless communication through any of the computing and measurement devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

The communication device may further comprise a user interface configured to permit a user (e.g., patient, predetermined contact such as a partner, family member, health care professional, etc.) to control the controller. The communication device may permit a user to interact with and/or control a controller directly and/or remotely. For example, a user interface of the controller may include an input device for a user to input commands and an output device for a user to receive output.

In some variations, an output device may comprise a display device comprising at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

In some variations, a user may communicate with other users using the audio device and a communication channel. For example, a user may form an audio communication channel (e.g., VoIP call) with a remote health care professional. In some variations, an audio device may comprise at least one of a speaker, piezoelectric audio device, magnetostrictive speaker, and/or digital speaker.

In some variations, the user interface may comprise an input device (e.g., touch screen) and an output device (e.g., a display). For example, user control of an input device (e.g., keyboard, buttons, touch screen) may be received by the user interface and may then be processed by processor and memory for the user interface to output a control signal to the cooling unit (150). Some variations of an input device may comprise at least one switch configured to generate a control signal. For example, an input device may comprise a touch surface for a user to provide input (e.g., finger contact to the touch surface) corresponding to a control signal. For example, a user may input a command to begin and stop cooling treatment, increase or decrease inflation pressure, increase or decrease fluid temperature, and/or set a cooling treatment session duration.

An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio data and recognize a user voice as a control signal.

A haptic device may be incorporated into one or more of the input and output devices to provide additional sensory output (e.g., force feedback) to the user. For example, a haptic device may generate a tactile response (e.g., vibration) to confirm user input to an input device (e.g., touch surface). As another example, haptic feedback may notify that user input is overridden by the controller.

Network

In some variations, the devices and systems described herein may be in communication with other devices (e.g., within the system, outside the system) or systems via, for example, one or more networks, each of which may be any type of network (e.g., wired network, wireless network). The communication may or may not be encrypted. A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks comprising wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication.

Methods

Also described here are methods for assembling a cooling cap assembly and for cooling a scalp using the systems and devices described herein. The methods of cooling a scalp of a head described herein may reduce, prevent, or assist in preventing hair loss, for example, resultant from chemotherapy. For example, the methods may increase heat transfer between a cooling cap assembly and a scalp of a patient and thus may improve the effectiveness of a scalp cooling treatment. As another example, the methods may increase user compliance with a cooling treatment therapy regimen. In some variations, methods may include use of a cooling cap assembly and a cooling unit that may be configured to provide a closed-loop feedback system for responsive cooling. In these variations, the methods may include adjusting one or more of an inflation pressure of an inflatable member, a temperature of a cooling fluid, and a cooling fluid flow rate based on sensor measurements, via, for example, a controller. Additionally or alternatively, methods may include adjusting one or more of the above mentioned parameters based on user input.

Assembling a Cooling Cap Assembly

Generally, methods of assembling a cooling cap assembly may comprise wrapping a heat exchanger around a portion of a head (e.g., a scalp, a portion of a scalp) and placing a compression assembly over the heat exchanger and onto the head. FIGS. 2I-2L are plan views of one variation of the assembly steps for applying a heat exchanger (200) to the scalp of a patient. The heat exchanger (200) is depicted separately from a patient's head for clarity. FIG. 2H depicts the exterior side of the heat exchanger in a spread out configuration where the interior side may be placed on top of a patient's head. The base portion (210) may be aligned with the neck and/or rear head of the patient with the top portion (221) laid over the top ridge and/or forefront of the head. When placed on a patient's head, the side portions (231, 241) may drape over the left and right hemispheres of the head. As shown in FIG. 2I, the first and second lobes (220, 222) of the top portion (221) may be flipped over the base portion (210). The ends of the first side portion (230) and second side portion (240) may be overlapped and held together, as shown in FIG. 2J, such that the side portions form an ovoid shape. A first lobe (220) of the top portion may be folded over at least a portion of the first side portion (230) and second side portion (240), as depicted in FIG. 2K. Then, as shown in FIG. 2L, a second side lobe (222) of the top portion may be folded over at least a portion of the top portion (220), first side portion (230), and second side portion (240). Fasteners may secure the overlapped portions to one another such that the heat exchanger forms a cap-like (e.g., semispherical) shape that may generally conform to the scalp of a patient. Additionally or alternatively, one or more of the assembly steps may be performed separately from the head, such as on a table or other surface, and the heat exchanger may be placed on the patient's head after partial or full assembly. Optionally, the patient may further adjust (e.g., tighten) the portions of the heat exchanger to optimize contact area and comfort after placement on the head.

FIGS. 7A-7F are a schematic depiction of a variation of a method of assembling a cooling cap assembly. In the variation depicted in FIGS. 7A-7F, the method may comprise forming a cooling cap assembly on head of a patient, by, for example, placing a liner on a scalp of a patient (700), wrapping a heat exchanger around a portion of the scalp (702), and applying a compression assembly over the heat exchanger (704, 706). The method of forming the cooling cap assembly may further comprise applying a cover over the compression assembly (708). While application of the compression assembly (e.g., an inflatable member and an enclosure) and the cover are depicted as separate steps (704-708), it should be appreciated that in some variations, the compression assembly and the cover may be coupled to one another (e.g., using snaps, buckles, bonding, hook and loop fasteners, or the like) such that they may be applied in a single step.

More specifically, in variations in which the cooling cap assembly comprises a liner, the method may begin by placing the liner around a portion of the head, for example, around a patient's scalp. The heat exchanger may be positioned on top of the liner (702) and the compression assembly may be placed on the head and over the wrapped heat exchanger such that the heat exchanger is disposed between the liner and the compression assembly. In variations in which a liner is not used, the heat exchanger may be placed in direct contact with the patient's scalp and may be disposed between the surface of the patient's scalp and the compression assembly. In particular, the inflatable member, which may be coupled to the enclosure (e.g., outer member, outer shell), may be placed over the heat exchanger (704) such that the heat exchanger is disposed between the inflatable member and the liner or the surface of the patient's scalp. In variations in which the cover is fixed to the enclosure, the cover may be placed on the patient's head in conjunction with the inflatable member and the enclosure. In other variations in which the cover is not originally fixed to the enclosure, the cover may be applied to the patient's head over the compression assembly. Methods may further comprise releasably coupling the cooling cap assembly to a patient's head using a fastener (e.g., a chin strap with a buckle, a hook, Velcro®, or the like.). FIG. 7F illustrates a partial cut-out cross-section of the cooling cap assembly (710) after application to, or assembly on, a head of a patient.

As mentioned above, in some variations, wrapping a heat exchanger around a portion of the scalp (702) may comprise fully or partially assembling the heat exchanger while it remains off of a patient's head, placing the fully or partially assembled heat exchanger on the head, and optionally adjusting the partially or fully assembled heat exchanger. In other variations, wrapping a heat exchanger around a portion of the scalp (702) may comprise partially or fully assembling the heat exchanger while the heat exchanger is on the patient's head.

In some variations, the heat exchanger may be separate from, but may releasably couple to, the compression assembly. In these variations, the heat exchanger may be removed from the head using the compression assembly. That is, the heat exchanger may form a friction fit with the inflatable member such that the compression assembly and the heat exchanger may be removed from a patient's head as a single piece. The heat exchanger may be placed back on the scalp using the compression assembly during future treatment sessions. In variations comprising a cover, the cover may also assist in removing from, securing, and re-applying the heat exchanger to a patient's head. In some variations, there may be a friction fit between the compression assembly and at least one other component of a cooling cap assembly (e.g., heat exchanger, cover) to reduce the number of disassembly steps. For example, the heat exchanger, compression assembly, and cover may be removed together from a patient's head in a single piece, thereby leaving just a liner on the patient's scalp. This single unit cooling cap assembly may then be placed back onto the patient's head to perform another cooling treatment session. Having previously adjusted and fitted the heat exchanger and inflatable member to the patient's anatomy, the assembled cooling cap assembly may be simply placed on top of the patient's head with minimal readjustment.

FIGS. 8A-8E are perspective views of another variation of a cooling cap assembly process. In this variation, a cover may be opened to receive the compression assembly (800). In particular, the enclosure or outer shell may be placed into a cavity of the cover (802). The inflatable member may be pre-shaped and placed into the outer shell or may be shaped through placement into the outer shell (804). The heat exchanger may be assembled and placed into the cavity of cover and the enclosure adjacent to the inflatable member (808). As described above, the heat exchanger may comprise a base portion, a top portion, a first side portion, and a second side portion. During assembly of the heat exchanger, the ends of the first side portion and the second side portion may be placed over one another. Similarly, an end of the top portion may be placed over the ends of the first side portion and the second side portion so as to surround at least the portion of the scalp when placed thereon.

Figure 9A:
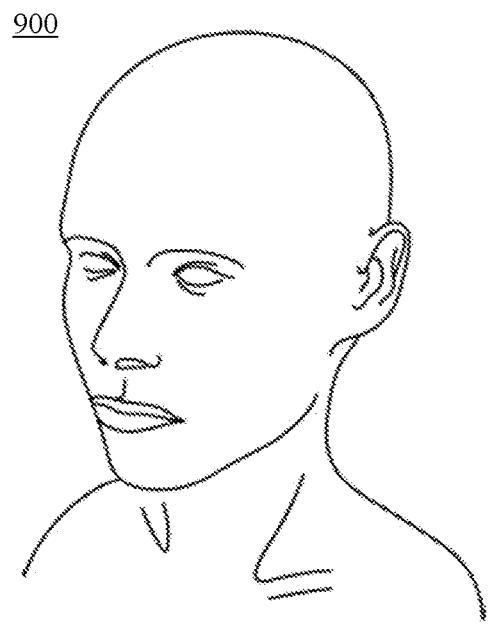
FIGS. 9A-9F are perspective views of an illustrative variation of a cooling cap assembly process.
Figure 9B:
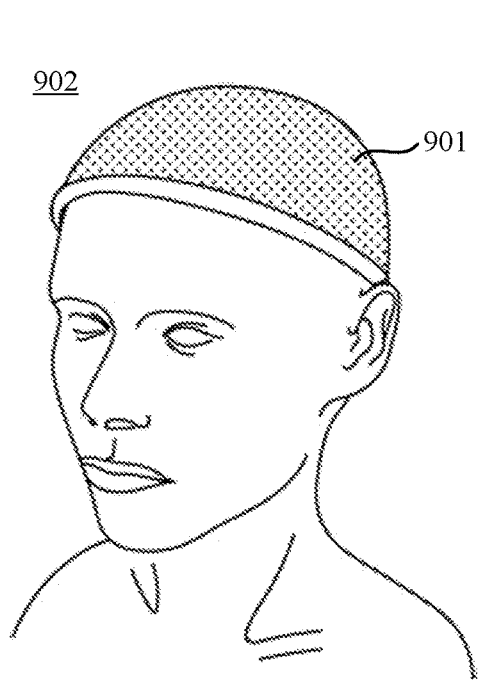
Figure 9C:
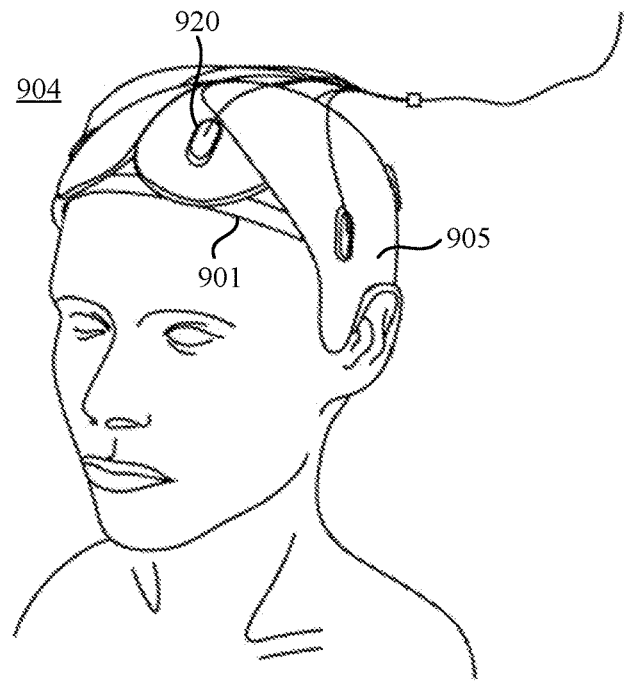
Figure 9D:
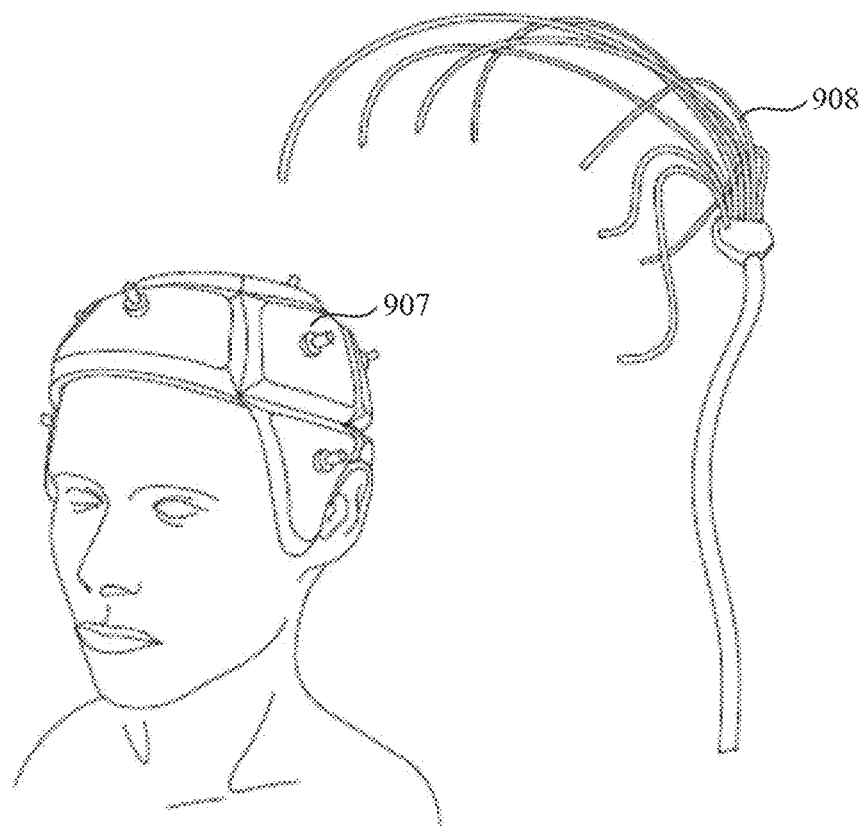
Figure 9E:
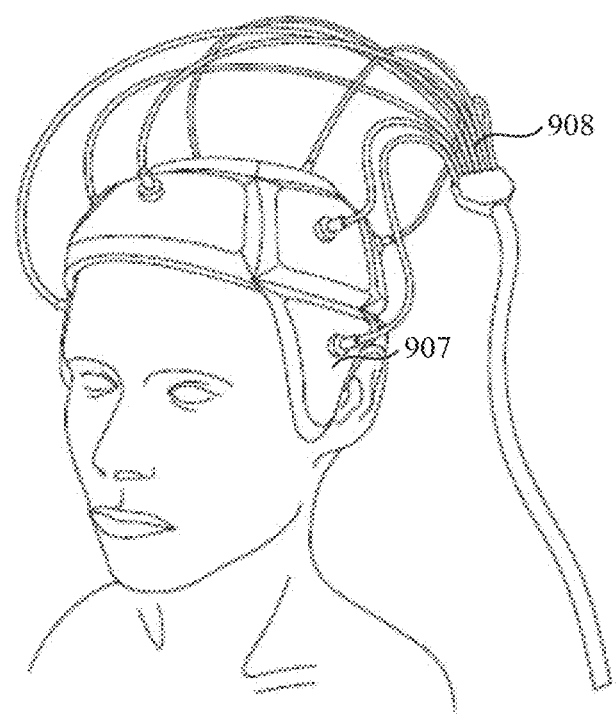
Figure 9F:
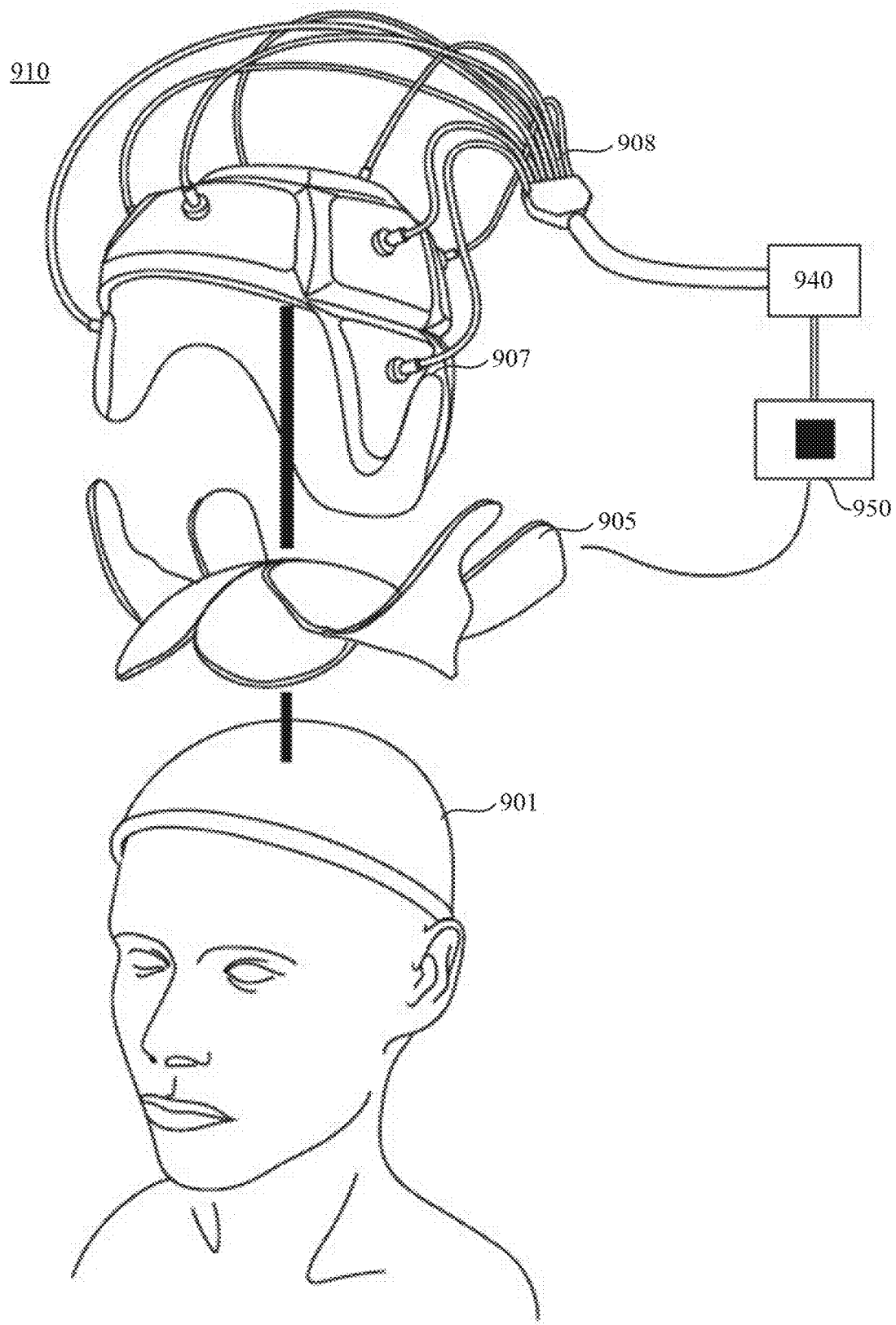

FIGS. 9A-9F are perspective views of yet another variation of a cooling cap assembly process. FIGS. 9A and 9B show a patient (900) and a liner (901) covering a portion of the head (902). A heat exchanger (905) may be wrapped around the head (904) over the liner (901), as shown in FIG. 9C. The heat exchanger (905) may comprise a plurality of sensors (920), which may be communicatively coupled (e.g., wired, wirelessly) to a controller (950). An inflatable member (907) may be placed over the heat exchanger (906) and a set of fluid conduits (908) may be coupled to the inflatable member (907). As shown in FIGS. 9D and 9E, the inflatable member (907) may comprise a plurality of independently inflatable chambers. FIG. 9F is an exploded schematic view of a cooling cap assembly process (910). The controller (950) may be configured to control circulating fluid through the heat exchanger (905) and/or inflation pressure of the inflatable member (907). The fluid conduits (908) may be coupled between the inflatable member (907) and a valve (940) controlled by the controller (950). The valve (940) may be coupled to a pump (not shown). As shown in FIG. 9F, the liner (901) may be placed directly on the scalp, with the heat exchanger (905) and the inflatable member (907) placed concurrently or sequentially thereon.

Using a Cooling System

Generally, methods of using a cooling cap assembly or cooling system described herein may comprise forming a cooling cap assembly on a patient's head, inflating an inflatable member, and circulating cooled fluid through the cooling cap assembly (e.g., the heat exchanger). In some variations, methods may further comprise controlling an inflation pressure of the cooling cap assembly, a temperature of a cooling fluid, and/or a flow rate of a cooling fluid. In some variations, a closed-loop feedback system may be used to dynamically control fluid temperature, fluid flow rate, and/or inflation pressure (i.e., to control compression) to optimize the cooling treatment.

As described in more detail above, forming a cooling cap assembly may comprise placing a liner on a scalp of a patient, wrapping a heat exchanger around a portion of the scalp, and applying a compression assembly over the heat exchanger. A cover may be fitted over the compression assembly and the cover may be fastened to the patient using, for example, a chin strap. A cooling fluid conduit may be used to couple the heat exchanger to a cooling unit and an inflation fluid conduit may be used to couple the inflatable member to a fluid pump (e.g., air pump such as air bulb).

The inflatable member may be inflated (i.e., transitioned from a deflated to an inflated configuration) to compress the heat exchanger between the inflatable member and the scalp (e.g., through the liner). In some variations, transitioning the inflatable member from a deflated to an inflated configuration may increase a force (e.g., pressure) applied to the head by the heat exchanger. A counter pressure may be generated using the enclosure (e.g., outer member) when the inflatable member is in an inflated configuration. Compression of from about 0.1 lb/in² to about 10 lb/in² may be generated to the head when the inflatable member is in an inflated configuration. In some variations, compression of from about 0.1 lb/in² to about 8.0 lb/in², from about 0.1 lb/in² to about 5.0 lb/in², from about 0.1 lb/in² to about 3.0 lb/in², from about 0.1 lb/in² to about 2.0 lb/in², from about 0.1 lb/in² to about 1.0 lb/in², from about 0.5 lb/in² to about 8.0 lb/in², from about 0.5 lb/in² to about 5.0 lb/in², from about 0.5 lb/in² to about 3.0 lb/in², from about 0.5 lb/in² to about 2.0 lb/in², about 1.5 lb/in² to about 2.5 lb/in², or from about 0.5 lb/in² to about 1.0 lb/in² may be generated to the head when the inflatable member is in an inflated configuration. The inflatable member may be inflated with any suitable fluid, for example a gas (e.g., air) or a liquid (e.g., water). In some variations, the inflatable member may be inflated using a hand pump, while in other variations the inflatable member may be inflated using an electric pump, for example, in the cooling unit.

Figure 17:
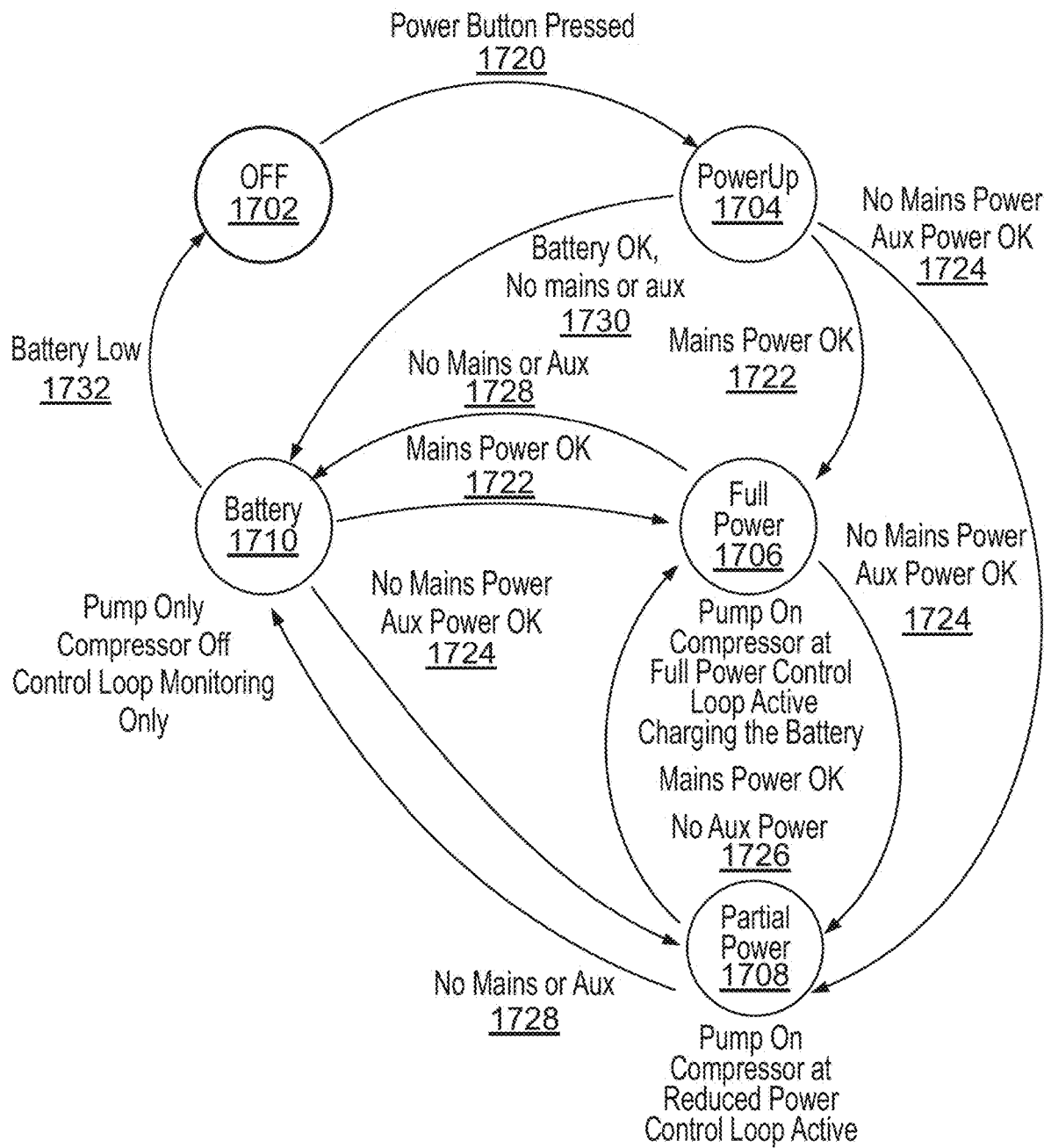
FIG. 17 is a state diagram of an illustrative variation of a cooling process.

Circulating cooling fluid through the cooling cap assembly may comprise circulating fluid at a temperature of from about −10° C. to about 5° C. through the heat exchanger using the cooling unit. In some variations, the fluid may be from about −2° C. to about 2° C. or from about −2° C. to about 4° C. The fluid may be circulated through the heat exchanger for the duration of the treatment session. The treatment session may include a pre-cooling portion before administration of a chemotherapy treatment, a transition portion in which a patient is traveling to receive a chemotherapy treatment, a chemotherapy portion in which the patient is receiving a chemotherapy treatment, a second transition portion in which a patient is traveling to another location (e.g., home) from the chemotherapy treatment, and a post-cooling portion in which the patient is continuing to cool the scalp for a period of time after a chemotherapy treatment. The patient may receive cooling treatment throughout each portion of a treatment session. In some variations, the fluid may be circulated for about 45 minutes to 10 hours, about 1 hour to about 8 hours, about 1 hour to about 6 hours, or about 1 hour to about 4 hours. The cooling system may be plugged into an electrical outlet during one or more portions of the treatment session (e.g., the pre-cooling portion, the chemotherapy portion, and the post-cooling portion), but need not be plugged into an electrical outlet during the transition portions. Put another way, the cooling unit may be battery powered during the transition portions (e.g., patient traveling from one location to another location) of a cooling treatment session. After the patient finishes a cooling treatment session, the cooling cap assembly may be removed from the head and stored for later use. In some variations, methods may further comprise re-applying the cooling cap assembly to the scalp and re-circulating cooling fluid as described above In some variations, a cooling unit may be operated in one of a plurality of operation states (e.g., full power, reduced power, battery power) with different functionality based on an available power source. For example, a pump and compressor may be turned on when at full power when the cooling unit is plugged into an AC power source while only a pump may be active when the cooling unit is in a battery power mode. FIG. 17 is a state diagram showing an illustrative method of controlling a cooling unit as described herein. In some variations, a cooling process (1700) may comprise a power OFF state (1702) in which a pump and compressor of a cooling unit is off (e.g., not receiving power). Consequently, the cooling unit may be inhibited from circulating fluid and/or providing cooled fluid to a cooling cap assembly. A patient or user may input a power ON signal (e.g., press a power button) to activate the cooling unit. In response, the controller may determine that the system transitions from a power OFF state (1702) to a power ON state (1704) (e.g., Power up state). In response to the power ON state (1704), the controller of the system may identify an active power source used to energize the cooling unit. The system may determine to transition from the power ON state (1704) to a full power state (1706) when the system first receives mains power (1722) (e.g., mains power OK, AC power supply). Mains power corresponds to, for example, wall power from an electric utility. In the full power state (1706), a cooling unit pump is on (e.g., active), and a cooling unit compressor may be operated at full power. For example, the cooling unit may be operated without any power restrictions or loss of functionality (e.g., control loop active). For example, an active control loop may comprise closed-loop temperature feedback. In some variations, a cooling unit battery may be recharged while in the full power state (1706).

The system may determine to transition from the power ON state (1704) or the full power state (1706) to a partial power state (1708) when the system is receiving auxiliary power and is not receiving mains power (1724) (e.g., auxiliary power OK). For example, the cooling unit in the partial power state (1708) may receive auxiliary power from a DC source such as a car battery. In the partial power state (1708), a cooling unit pump is on (e.g., active), and a cooling unit compressor may be operated in a reduced power state (e.g., about 50% to about 80% of full power state). For example, the cooling unit may be operated up to a predetermined power level with closed-loop control.

The system may determine to transition from the power ON state (1704) to a battery power state (1710) when the system is receiving cooling unit battery power and not receiving mains power or auxiliary power (1730) (e.g., battery OK, no mains or aux power). In the battery power state (1710), a cooling unit pump is on (e.g., active), and the cooling unit compressor is off. Therefore, fluid may be circulated but not actively cooled by the cooling unit. In some variations, sensor measurements may be performed without active closed-loop control (e.g., control loop monitoring only).

The system may determine to transition from the partial power state (1708) to the full power state (1706) when the system is receiving mains power and not receiving auxiliary power (1730) (e.g., mains power OK, no aux power). The system may determine to transition from the partial power state (1708) to the battery power state (1710) when the system is not receiving mains or auxiliary power (1728) (e.g., no mains or aux power).

The system may determine to transition from the battery power state (1710) to the partial power state (1708) when the system receives auxiliary power and is not receiving mains power (1724) (e.g., no mains power, aux power OK). The system may determine to transition from the battery power state (1710) to the full power state (1706) when the system receives mains power (1722) (e.g., mains power OK). The system may determine to transition from the battery power state (1710) to the power OFF state (1702) when the battery reaches a predetermined power level (1732) (e.g., battery low).

The system may determine to transition from the full power state (1706) to the battery power state (1710) when the system is not receiving mains or auxiliary power (1728) (e.g., no mains or aux power). The system may determine to transition from any of the power states (except the power OFF state) to a power OFF state (1702) when a patient or user inputs a power off signal (e.g., press a power button).

As mentioned above, in some variations, the methods described here may comprise controlling or otherwise adjusting (e.g., manually or automatically) an inflation pressure of the cooling cap assembly, a temperature of a cooling fluid, and/or a flow rate of a cooling fluid. In some variations, the cooling unit may comprise a user interface through which the patient may control one or more of the cooling unit (e.g., inflatable member pump, circulating fluid pump) and cooling cap assembly. Additionally or alternatively, the patient may control the temperature and/or flow rate of the circulating fluid and/or an inflation pressure of the compression assembly using a graphical user interface (GUI) displayed on a computing device such as a smartphone or tablet. For example, the GUI may output sensor measurements including temperature, force, inflation pressure, and fluid flow rate generated by the various sensors of the system.

In some variations, a controller may dynamically control treatment time, inflation pressure, fluid temperature, and/or fluid flow rate. For example, the controller may instruct or otherwise transmit signals to the cooling unit (e.g., one or more pumps, compressor) to alter one or more cooling parameters (e.g., flow rate of cooling fluid, temperature of cooling fluid, inflation pressure of one or more chambers of an inflatable member). In some variations, the patient may be notified when one or more temperature measurements exceed predetermined thresholds and may be provided the option to adjust one or more cooling treatment parameters using, for example, a computing device or the user interface on the cooling unit.

As an example, in one variation, the method may comprise circulating fluid through the heat exchanger coupled to a scalp of a patient and adjusting a cooling parameter of the cooling system based on one or more temperature and/or force measurements. In some variations, adjusting the cooling parameter may comprise manually adjusting the cooling parameter (e.g., inflation pressure, temperature of cooling fluid, flow rate of cooling fluid). In these variations, the patient may control one or more of the cooling parameters using the graphical user interface of a controller (e.g., mobile phone, tablet). In some of these variations, a patient may be notified using the graphical user interface to manually modify (e.g., increase) an inflation pressure of a cooling cap assembly by manually actuating a pump in response to a measured temperature and/or force. For example, an animation of a hand squeezing a pump may be displayed on a display of a patient's computing device when an average measured temperature exceeds a predetermined temperature threshold.

Additionally or alternatively, adjusting the cooling parameters may comprise using the controller to dynamically (e.g., automatically) adjust one or more cooling parameters based on one or more of the measured temperatures and/or forces (e.g., a single temperature/force measurement, an average of a plurality of temperature/force measurements) and predetermined temperature and/or force thresholds, maximums, targets, or ranges. For example, in the variation in which dynamic control is utilized, if an average measured temperature exceeds a predetermined temperature threshold, the controller may increase the inflation pressure of an inflatable member using, for example, one or more fluid valves and/or a fluid pump coupled to the inflatable member as described in more detail above. If a measured inflation pressure exceeds a predetermined pressure threshold, the controller may decrease the inflation pressure until the inflation pressure is within a suitable range. If the measured inflation pressure is within a target range, the controller may maintain the inflation pressure within that range. Additionally or alternatively, if one or more temperatures (e.g., a temperature of the cooling fluid measured within the cooling unit, a temperature of the cooling fluid measured within the heat exchanger, temperature measured on or at a patient's scalp, an average of several temperatures measured on or at a patient's scalp, a calculated delta T between any of the aforementioned temperatures) is above or below a target value and/or outside of a target range, the controller may adjust one or more parameters of the cooling system to adjust (e.g., increase or decrease) the heat transfer between the cooling cap assembly and the patient's scalp. For example, the controller may adjust the temperature of the circulating cooling fluid by adjusting the power of the compressor of the cooling unit and/or may adjust the flow rate of the cooling fluid by adjusting the power of the cooling fluid pump in the cooling unit until the temperature reaches the target, surpasses a threshold value, is below a maximum value, or is within a target range. In some variations, the patient may be notified audibly and/or visually when the controller alters one or more of the inflation pressure, fluid temperature, and fluid flow rate so as to reduce surprise or anxiety.

In some variations, the method may further comprise independently adjusting an inflation pressure of a plurality of chambers (e.g., each chamber) of the inflatable member based on a set of measured temperatures. For example, an inflation pressure of in a chamber of the inflatable member may be increased when a measured temperature or an average of measured temperatures of a corresponding portion of the heat exchanger exceeds a predetermined maximum temperature. As another example, a measured temperature of a first arm or lobe of a heat exchanger may exceed a predetermined maximum temperature such that the controller may adjust one or more valves and/or a fluid pump to inflate the chamber of the inflatable member corresponding to the arm or lobe. In these variations, additional cooling may be precisely targeted on the patient's head. Once the measured temperature of the arm or lobe reduces to below the predetermined threshold, the controller may maintain the pressure of the chamber or may deflate the chamber to a predetermined pressure.

In some variations, methods may further comprise generating a patient profile for each patient. The patient profile may comprise a set of cooling treatment protocols that may be executed for a variety of patient scenarios. For example, a quiet treatment protocol may reduce the power consumption of the cooling unit such that noise is reduced. A maximum cooling treatment protocol may apply a predetermined maximum compression to a heat exchanger and set the circulating fluid to a predetermined maximum flow rate in order to maximize heat transfer. In some variations, a patient may personalize the treatment protocols and/or the system may adjust preset treatment protocols based on patient information input into the system. The patient may further be provided real-time control of treatment parameters such as treatment time, inflation pressure, fluid temperature, and fluid flow rate. Moreover, the GUI may include visual instructions on how to assemble or wrap the heat exchanger, assemble and disassemble the cooling cap assembly from the patient's head, as well as how to operate the cooling unit and perform a cooling treatment session. For example, in some variations, the GUI may provide a series of visual and/or audible (e.g., spoken) prompts that instruct a user how to assemble the heat exchanger, how to assemble and/or disassemble the cooling cap assembly, and/or how to perform a cooling treatment session.

Examples

Figure 10:
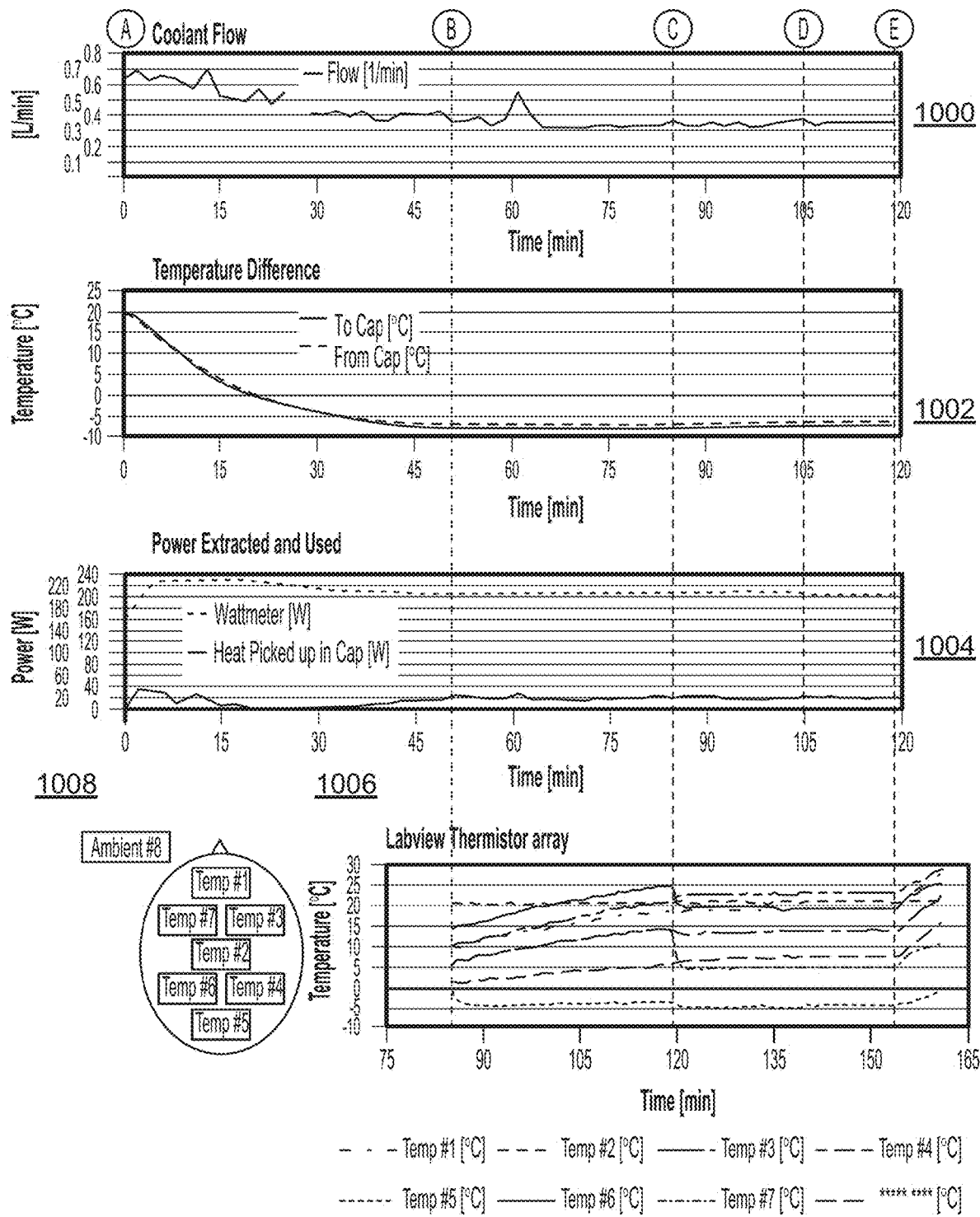
FIG. 10 is a set of plots of sensor and power measurements of an illustrative variation of a cooling cap assembly.

FIG. 10 is a set of graphs of sensor and power measurements of one variation of a cooling cap assembly. As shown in FIG. 10, parameters including coolant flow (1000), temperature change (1002), power (1004) (i.e., extracted power, used power) may be plotted against time. An array of temperature sensors (1008) may be placed over a head with the temperature (1006) of each sensor plotted against time. At time point A of FIG. 10, pre-cool full power is applied. At time point B, a cooling cap assembly powered by a 40 W load may be applied to a head of a patient. At time point C, an inflatable member of the cooling cap assembly may be inflated to increase the contact area between the heat exchanger and the patient's scalp. For example, the inflatable member may be inflated to increase compression to the head. At time point D, the speed of a compressor may be reduced in order to reduce noise and increase patient comfort. As the fluid within the heat exchanger reduces in temperature and the contact area between the cooling cap and the scalp increases, the fluid flow through the heat exchanger may be decreased while at least maintaining an effectiveness of cooling therapy. At time point E, the system may be turned off. Between time points C and E, steady state may be achieved where all 40 W are removed.

The specific examples and descriptions herein are exemplary in nature and variations may be developed by those skilled in the art based on the material taught herein without departing from the scope of the present invention, which is limited only by the attached claims.

We claim:

1. A cooling cap assembly comprising:
a flexible heat exchanger configured to remove heat from a scalp of a patient;
and a cooling unit fluidly coupled to the heat exchanger and configured to circulate fluid through the heat exchanger, the cooling unit comprising:
a controller configured to:
determine a power source for the cooling unit among an auxiliary power source, a battery of the cooling unit, and an AC power source;
select a first active operation state of the cooling unit when the determined power source is the auxiliary power source;
select a second active operation state of the cooling unit different from the first active operation state when the determined power source is the battery;
select a third active operation state of the cooling unit different from the first and second active operation states when the determined power source is the AC power source;
and restrict a maximum power level of a compressor of the cooling unit based on the determined power source being among the auxiliary power source and the battery.

2. The cooling cap assembly of claim 1, wherein a fluid flow rate of the fluid circulated through the heat exchanger by the cooling unit is based on the determined power source, and wherein each power source corresponds to a different maximum fluid flow rate.

3. The cooling cap assembly of claim 1, wherein the cooling unit comprises the compressor and a pump.

4. The cooling cap assembly of claim 3, wherein the active operation state is one of a full power state a partial power state, and a battery power state.

5. The cooling cap assembly of claim 4,
wherein the pump and the compressor are active in the full power state, the pump is active and the compressor is restricted to a reduced power state in the partial power state based on the determined power source being]the auxiliary power source, and the pump is active and the compressor is restricted to inactive in the battery power state based on the determined power source being the battery.

6. The cooling cap assembly of claim 5, wherein the reduced power state of the compressor is restricted to between about 50% to about 80% of the full power state of the compressor independent of temperature.

7. The cooling cap assembly of claim 6, wherein the battery is configured to recharge in the full power state.

8. The cooling cap assembly of claim 4, wherein the battery power state comprises control loop monitoring only and the partial power state comprises active closed-loop control.

9. The cooling cap assembly of claim 1, wherein the active operation state is a battery power state when the determined power source is the battery of the cooling unit.

10. The cooling cap assembly of claim 1, wherein the active operation state is a partial power state when the determined power source is the auxiliary power source.

11. The cooling cap assembly of claim 1, wherein the auxiliary power source is a car battery.

12. The cooling cap assembly of claim 1, wherein the cooling unit circulates the fluid through the heat exchanger at a temperature of from about −10° C. to about 5° C.

13. The cooling cap assembly of claim 1, wherein the cooling cap assembly further comprises an inflatable member releasably coupled to the heat exchanger, and an outer shell coupled to the inflatable member.

14. The cooling cap assembly of claim 1, wherein the cooling unit comprises a user interface configured to receive patient input to control the cooling unit.

15. A method of controlling cooling of a scalp of a head of a chemotherapy patient comprising:
applying a cooling cap assembly to the head, wherein the cooling cap assembly comprises a flexible heat exchanger;
circulating a fluid through the heat exchanger using a cooling unit fluidly coupled to the heat exchanger, wherein the cooling unit comprises a plurality of active operation states;
determining a power source of the cooling unit, wherein the determined power source is one of an auxiliary power source, a battery of the cooling unit, and an AC power source; and
selecting a first active operation state of the cooling unit when the determined power source is the auxiliary power source;
selecting a second active operation state of the cooling unit different from the first active operation state when the determined power source is the battery;
selecting a third active operation state of the cooling unit different from the first and second active operation states when the determined power source is the AC power source;
and restricting a maximum power level of a compressor of the cooling unit based on the determined power source being among the auxiliary power source and the battery.

16. The method of claim 15, wherein the cooling unit comprises the compressor and a pump.

17. The method of claim 16, wherein the active operation state is one of a full power state, a partial power state, and a battery power state.

18. The method of claim 17,
wherein the pump and the compressor are active in the full power state, the pump is active and the compressor is restricted to a reduced power state in the partial power state based on the determined power source being the auxiliary power source, and the pump is active and the compressor is restricted to inactive in the battery power state based on the determined power source being the battery.

19. The method of claim 18, wherein the reduced power state of the compressor is restricted to between about 50% to about 80% of the full power state of the compressor independent of temperature.

20. The method of claim 19, further comprising recharging the battery of the cooling unit in the full power state.

21. The method of claim 17, wherein the battery power state comprises control loop monitoring only and the partial power state comprises active closed-loop control.

22. The method of claim 15, further comprising releasably coupling an inflatable member to the heat exchanger, and releasably coupling an outer shell to the inflatable member.

* * * * *